(12) United States Patent
Nayudu et al.

(10) Patent No.: US 7,087,424 B1
(45) Date of Patent: Aug. 8, 2006

(54) METHOD OF CONTROLLING FUNGAL PATHOGENS, AND AGENTS USEFUL FOR SAME

(75) Inventors: Murali Nayudu, Canberra (AU); Rajvinder Kaur, Canberra (AU)

(73) Assignee: Australian National University, Australian Capital Territory (AT)

( * ) Notice: Subject to any disclaimer, the term of this patent is extended or adjusted under 35 U.S.C. 154(b) by 0 days.

(21) Appl. No.: 09/890,306

(22) PCT Filed: Jan. 28, 2000

(86) PCT No.: PCT/AU00/00046

§ 371 (c)(1),
(2), (4) Date: Oct. 25, 2001

(87) PCT Pub. No.: WO00/44230

PCT Pub. Date: Aug. 3, 2000

(30) Foreign Application Priority Data

Jan. 29, 1999 (AU) ...................................... PP8394

(51) Int. Cl.
*A01N 63/00* (2006.01)
*C12N 1/20* (2006.01)

(52) U.S. Cl. ................ 435/253.3; 435/874; 424/93.47; 504/117

(58) Field of Classification Search ............. 424/93.47; 435/874, 253.3; 504/117
See application file for complete search history.

(56) References Cited

U.S. PATENT DOCUMENTS

| | | | |
|---|---|---|---|
| 4,456,684 A * | 6/1984 | Weller et al. ................. | 435/34 |
| 4,817,333 A | 4/1989 | Szepessy et al. .............. | 47/58 |
| 5,691,378 A | 11/1997 | Yu et al. ...................... | 514/557 |
| 5,719,172 A | 2/1998 | Oppong et al. ............. | 514/367 |
| 5,759,558 A | 6/1998 | Epstein et al. .............. | 424/401 |
| 5,811,090 A | 9/1998 | Tahvonen et al. .......... | 424/93.5 |
| 5,856,357 A | 1/1999 | Yu et al. ...................... | 514/557 |

FOREIGN PATENT DOCUMENTS

| | | |
|---|---|---|
| DE | 2651947 A1 | 5/1978 |
| DE | 3338689 A1 | 5/1985 |
| DE | 3443985 A1 | 6/1986 |
| EP | 0 713 645 A1 | 5/1996 |
| JP | 62-190103 | 8/1987 |
| WO | WO 91/13552 | 9/1991 |
| WO | WO 94/07365 | 4/1994 |
| WO | WO 94/28883 | 12/1994 |

OTHER PUBLICATIONS

Dahiya et al. Bot. Bull. Academia Sinica (1988), 29: 135-142.*
XP002220176, Database WPI, Section Ch. Week 198118, Derwent Publications Ltd., London, GB.
XP002220177, Database WPI, Section Ch. Week 198121, Derwent Publications Ltd., London, GB.
XP002220178, Database WPI, Section Ch. Week 199729, Derwent Publications Ltd., London, GB.
Elzainy et al., "Occurrence of the non-phosphorylative Pathway for Gluconate Degradation in Different Fungi", Biochemical Systematics 1:127-128, 1973.
Meulenberg et al., "Nucleotide Sequence and Structure of the *Klebsiella penumoniae* pqq Operon", Mol. Gen Genet 232:284-294, 1992.
Nayudu et al., "The Genetic Nature of Biological Control of the Take-all Fungal Pathogen by *Pseudomonas*", Improving plant productivity with Rhizosphere bacteria, International workshop on plant growth promoting Rhizobacteria (1994) Adelaide, South Australia, Editors Bowen GD et al., p. 122-124.
Schnider et al., "Tn5-Directed Cloning of pqq Genes from *Pseudomonas fluorescens* CHAO: Mutational Inactivation of the Genes Results in Overproduction of the Antibiotic Pyoluteorin", Applied and Environmental Microbiology 61:3856-3864, 1995.
Sponholz et al., "Uber Die Herkunft von Gluconsaure, 2-und 5-Oxo-Gluconsaure Sowie Glucuron-und Galacturonsaure in Mosten und Weinen", Vitus 24:51-58, 1985.

* cited by examiner

*Primary Examiner*—Vera Afremova
(74) *Attorney, Agent, or Firm*—Fish & Richardson P.C.

(57) ABSTRACT

A method of preventing or treating infection by a range of fungal pathogens in an animal or plant or stored plant product comprising administering an effective amount of a sugar acid, in particular mannonic acid, gluconic acid or galacturonic. The sugar acid can be delivered by a biocontrol that can manufacture the sugar acid. An exemplified biocontrol is *Pseudomonas* strain AN5, which is characterized by the capacity to convert aldose to sugar acid. Also disclosed are nucleotide sequences from enzymes in the *Pseudomonas* PQQ enzyme pathway which may be used to transform microorganisms and plants so that they produce sugar acids at levels sufficient to control the growth or viability of pathogens.

27 Claims, 23 Drawing Sheets

(a)     (b)

(a)      (b)

METHOD OF CONTROLLING FUNGAL PATHOGENS, AND AGENTS USEFUL FOR SAME

FIELD OF THE INVENTION

The present invention relates generally to the use of a sugar acid to inhibit, retard or otherwise control the growth and/or viability of plant pathogens, such as, for example, those prokaryotic and eukaryotic organisms which infect or otherwise infest plants or parts of plants. In particular, the present invention relates to the use of a sugar acid selected from the group consisting of gluconic acid, mannonic acid, malic acid, ascorbic acid, glucaric acid, glutaric acid, glucuronic acid, galacturonic acid and galactonic acid to inhibit, retard or otherwise control the growth and/or viability of a plant pathogen, in particular a fungal pathogen. The invention further extends to the use of a sugar acid in the manufacture of a phytoprotective agent for the treatment of fungal infestations of plants. As disclosed herein, the sugar acid may be applied to a plant or plant part in crude or pure form, and, as a consequence, the invention further extends to a microorganism which is capable of producing a sugar acid when provided with an appropriate substrate, such as, for example, a species or sub-species of the genus *Pseudomonas* which is capable of metabolizing D-glucose and other carbon sources to a corresponding sugar acid. The present invention further provides nucleotide sequences of *Pseudomonas* sp. which encode and/or otherwise facilitate the synthesis of sugar acids in prokaryotic and eukaryotic organisms, in particular bacteria and/or plants. The present invention further contemplates transgenic plants and microorganisms which have been genetically engineered to produce sugar acids at levels sufficient to control the growth and/or viability of one or more plant pathogens.

General

This specification contains nucleotide sequence information prepared using the programme Patentin Version 2.0, presented herein after the claims. Each nucleotide sequence is identified in the sequence listing by the numeric indicator <210 followed by the sequence identifier (e.g. <210>1, <210>2, etc). The length, type of sequence (DNA, protein (PRT), etc) and source organism for each nucleotide sequence are indicated by information provided in the numeric indicator fields <211>, <212> and <213>, respectively. Nucleotide sequences referred to in the specification are defined by the term "SEQ ID NO:", followed by the sequence identifier (eg. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

Bibliographic details of the publications referred to in this specification are collected at the end of the description.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only. Functionally-equivalent products, compositions and methods are clearly within the scope of the invention, as described herein.

BACKGROUND OF THE INVENTION

Pathogenic infections, in particular fungal infections, of animals (including humans and agricultural and domestic animals), and plants, (in particular, agriculturally-significant plants) produce significant losses in productive capacity worldwide.

True fungal pathogens may be classified into at least three major classes, the Phycomycetes, the Ascomycetes, and the Basidiomycetes.

With particular regard to fungal pathogens which infect humans and other mammals, over 40 species are known which attack epithelial tissues (eg. hair, skin, and nails), causing diseases and discomforts of an annoying nature, such as, for example, tinea pedis (athlete's foot), tinea cruris, tinea corporis (ringworm) due to infection by the dermatophytes *Trichophyton rubrum, T. mentagrophytes, Epidermophyton floccosum*, and *Microsporum canis*; candidiasis due to *Candida albicans*, including cutaneous candidiasis (thrush), onychia, paronychia, external genital candidiasis, candidal balanitis; pityriasis versicolor due to *Pityrosporum orbiculare* (*Malassezia furfur*); and jockey-strap itch. Additionally, certain species of fungi infect sub-cutaneous tissues, including those of major internal organs, to produce serious systemic diseases, including blastomycosis, coccidiomycosis, histoplasmosis, and sporotrichosis. These more serious fungal infections are generally soil-borne, easily aerosolized, spread by air currents, and, as a consequence, contracted by inhalation. The fungal pathogens are mostly dimorphic, occurring as a mycelium in the non-pathogenic state, which bears infectious spores.

Many more fungal pathogens produce a variety of diseases in plants, wherein different species of fungi tend invade particular species, and particular tissues, of plants. Crop damage from fungal infection accounts for many millions of dollars in lost profits annually. The Basidiomycetes are of particular importance in agriculture, and include the rust fungi, such as, for example, *Puccinia* spp., *Cronartium ribicola*, and *Gymnosporangium juniperi-virginianae*; the smut fungi, such as, for example, *Ustilago* spp., which infect corn and oats, amongst others, causing up to 30% losses annually. Additionally, take-all disease, which is caused by infection of wheat plants by the fungal pathogen *Gaeumannomyces graminis* var *tritici* (or commonly known as the "take-all" fungus) is the most significant root disease of wheat around the world and currently leads to 10% loss of the annual wheat crop in Australia (Murray and Brown, 1987). Other important fungal diseases in plants include crown wart of alfalfa disease, which is caused by *Physoderma alfalfae*; bitter rot of apple disease, caused by *Glomerella cingulata*; apple rust, caused by *Gymnosporangium juniperi-virginianae*; apple scab, caused by *Venturia inaequalis*; banana wilt, caused by *Fusarium oxysporum* f. *cubense*; loose smut of barley, caused by *Ustilago nuda* Rostr.; early and late blight in celery, caused by *Septoria apiicola; Fusarium* yellow in celery, caused by *Fusarium oxysporum* f. *apii* Snyder Hansen; ergot in grain crops, and grasses, caused by *Claviceps purpurea*; stem rusts, caused by *Puccinia* spp., in particular *P. graminis*; late blight in potato, caused by *Phytopthera infestans*; and citrus root rot diseases caused by *Armillaria mellae*. However, this list is not exhaustive.

Methods for the prophylactic and/or therapeutic treatment of fungal and bacterial infections in animals and plants generally involve the application of anti-fungal and anti-bacterial chemicals; the use of biocontrol agents; and, more recently, and particularly in the case of plants, the genetic engineering of crops to express disease tolerance or disease-resistance genes therein.

Funcidal and Fungistatic Chemical Compounds:

Anti-fungal chemicals are varied in composition and designed to either eradicate the fungal pathogen, such as, for example, by acting against the fungal spores, or alternatively, to prevent the germination of fungal spores once they have infected their host. However, most chemicals do not fall exclusively into a single category. For example, elemental sulfur has been used to protect apple crops against apple scab, however the same chemical is eradicative when used against a rust fungus.

A wide variety of pyridine compounds and derivatives thereof having varying, and often multiple, action, are used in agrochemicals and pharmaceuticals against fungal pathogens, such as, for example, 3-(2-methylpiperidino) propyl-3,4-dichlorobenzoate; cephalosporin C; cephapirin sodium; pyrithione zinc (i.e. 2-mercaptopyridine N-oxide); and 2-sulfanylamidopyridine.

Many of the compounds used commonly to treat fungal infections in humans interfere with fungal sterol biosynthesis. For example, the imidazoles (including bifonazole [i.e. 1-(α-biphenyl-4-ylbenzyl)-imidazole], clotrimazole, econazole nitrate, and miconazole nitrate [i.e. 1-[2,4-dichloro-β-(2,4-dichlorobenzyloxy)phenethyl]imidazole nitrate]), which have broad spectrum antifungal activity against dermatophytes and yeasts alter fungal cell membranes by interfering with ergosterol production. The allylamines, such as, for example, terbafine hydrochloride ($C_{21}H_{25}$ N. HCl), are also of use in the treatment of infections by dermatophytes, also interfere with ergosterol production. Terbafine also results in the accumulation of squalene in the fungus, resulting in fungal cell death. Amorolfine hydrochloride (cis-4-[(RS)-3-[4-(1,1-dimethylpropyl)phenyl]-2-methyl propyl]-2,6-dimethyl morpholine hydrochloride) is in a relatively new class of compounds active against a wide range of yeasts, dermatophytes, moulds, and dimorphic fungi. The fungicidal/fungistatic effect of amorolfine hydrochloride is based upon modification to the fungal cell membranewhich is produced by reducing the ergosterol content and increasing the levels of sterically-nonplanar sterols in the fungal cell membrane.

Agricultural fungicides and their modes of application are reviewed in detail by Gennaro et al. (1990), and Kirk-Othmer (1980). These compounds are generally of the class of polysulfides; heavy-metal fungicides; and the organic fungicides, such as, for example, the quinones (in particular, chlroanil and dichlone), organic sulfur-containing compounds (in particular, the dithiocarbamates), imidazolines and guanines (in particular heptadecyl-2-imidozolinium acetate; and dodecylguanidium acetate), trichloromethylthiocarboximides [in particular, N-trichloromethylthio)$_4$-cyclohexene-1,2-dicarboximide (captan); and N-(trichloromethylthio) phthalimide (folpet)], the chlorinated and/or nitrated benzene derivatives [in particular, 2,3,5,6-tetrachloronitrobenzene; pentachloronitrobenzene (PCNB); 1,3,5-trichloro-2,4,6-trinitrobenzene; 1,2,4-trichloro-3,5-dinitrobenzene; hexachlorobenzene; 2,6-dichloro-4-nitroaniline (dichloran); 1,4-dichloro-2,5-dimethoxybenzene; and tetrachloroisophthalonitrile (chlorothalonil)]. Various other compounds having systemic anti-fungal activity in agricultural applications (i.e. systemic fungicides) include the oxathiins (in particular, carboxin); benzimidazoles [in particular, methyl-2-benzimidazolylcarbamate (MBC)]; pyrimidines [in particular, 5-butyl-2-dimethylamino-6-methyl-4(1H)-pyrimidinone (dimethirimol); the 2-ethylamino analogue, ethirimol; and α-(2,4-dichlorophenyl)-α-phenyl-5-pyrimidinemethanol (triarimol)]. The antibiotics, including cycloheximide, bastocidin S, kasugamycin, and the polyoxins, are also used extensively.

In most cases the mode of action of known agricultural anti-fungal compounds remains elusive, and, as with anti-fungal compounds that are effective against fungal pathogens of humans, many compounds alter fungal cell membrane metabolism. For example, triarimol and related compounds inhibit steps in sterol biosynthesis. However, carboxin is known to block mitochondrial respiration by inhibiting succinate dehydrogenase, whilst the benzimidazoles disrupt cell structures, such as those required for mitosis.

Anti-fungal Biocontrol Agents:

Biological control protection refers to the introduction of living organisms, such as, for example, bacteria, fungi, and insects, to control plant pathogens. Three properties make biocontrol agents a desirable option in plant protection against fungal pathogens. First, biocontrol agents are generally natural products and, as such, are less likely to have a detrimental effect on the environment than synthetic chemicals. Secondly, biocontrol agents are relatively inexpensive compared to synthetic chemicals. Third, biocontrol agents represent an inexhaustible source of protectant, because microorganisms can be maintained in culture, and expanded rapidly and inexpensively.

Biocontrol agents either act by occupying the site of infection of a pathogen, and competing with the pathogen for nutrients derived from the plant, or alternatively, the biocontrol agent produces fungicidal and/or fungistatic compounds that specifically attack the fungal pathogen. Significant factors important in biological control (such as colonization, antibiosis, siderophore production etc.) have been identified, however the influence of these factors varies with environmental conditions so it is difficult to assign a universal mechanism of action to biocontrol agents (Weller, 1988).

The universal feature of all biocontrol agents is their capacity to rapidly multiply in the cells and tissues that are infected by the pathogenic agent and to form an association therewith, a process which has been termed "colonization" (Suslow, 1982). In fact, Weller (1988) identified three factors as being responsible for the suppressive nature of various bacteria against fungi: colonization of the root; the production of fungicides and/or fungistatic compounds, including antibiotics, HCN (Fravel, 1988), or hydrogen peroxide (Wu et al, 1995; U.S. Pat. No. 5,516,671), amongst others; and the production of fluorescent siderophores, or high-affinity iron-transport agents. In this regard, the different colonization host range shown by biocontrol bacteria (Weller, 1988) suggests there is some host specificity in colonization, and that a number of factors are involved. As will be known to those skilled in the art, there is also host-specificity in the action of fungicides, and this might explain why some strains are ineffective against certain pathogens (Schroth and Hancock, 1981). Additionally, not all biocontrol agents act by producing fungicides or fungistatic compounds (Kraus and Loper, 1992).

There are a large number of systems in which biocontrol is effective (Weller, 1988). In general, biocontrol agents have been shown to have a beneficial effect to the plant under controlled conditions in the glasshouse and in a large number of cases in the field (Baker and Cook, 1974). There are currently numerous biocontrol agents used by farmers for disease control (Schroth and Hancock, 1981), showing that it is effective and viable as a method to control plant diseases in the field.

For example, Sclerotinia rot, caused by the fungi Sclerotinia sclerotiorum, Sclerotinia minor, and Sclerotinia trifoliorum, is one of the most destructive diseases of plants, affecting over 380 ornamentals (e.g. aster, begonia, calendula, chrysanthemum, fuchsia, gerbera, lupin, pelargonium, and petunia), field crops (e.g. alfalfa, canola, dry bean, hemp, lentil, oilseed rape, peanut, potato, red clover, safflower, soybean, sunflower, sweetclover, and tobacco), vegetables and fruits (e.g. artichoke, asparagus, avocado, bean, broccoli, cabbage, carrot, celery, chickpea, chicory, cucumber, eggplant, endive, fennel, kiwi fruit, leek, lettuce, parsley, pea, pepper (chilli, red or sweet), snap bean, tomato, watermelon, garlic and onion) and herbs (e.g. coriander, chives, dill, fennel, and wintercress). A biological plant-protection agent, containing as an active ingredient contains viable spores of the soil fungus Coniothyrium minitans, has been developed recently which has specific antagonistic action against the survival structures (sclerotia) of these fungal pathogenic agents. Once applied and incorporated into the soil, C. minitans germinates and attacks the sclerotia (resting survival structures) of the pathogens within the soil, thereby reducing recurrences of the disease in the soil.

In the case of take-all disease in wheat, Pseudomonas sp., have been identified which produce a low molecular weight siderophore, sometimes fluorescent, capable of complexing and actively-transporting iron inside the cell, to produce an iron deficiency in the soil (Buyer and Leong, 1986; Leong, 1986), thereby effectively starving the fungal pathogen of soil-derived iron necessary for germination and growth. However, siderophore production is now thought only to be important in the biocontrol of take-all disease in alkaline soils which have low iron concentration, wherein iron may be a limiting nutrient for the fungus (Kloepper et al., 1980). Moreover, Fravel, (1988); Hamdan et al. (1991); and Thomashow et al., (1990), have suggested that the dominant important factor in disease suppression is the production of fungicides and/or fungistatic compounds by Pseudomonas Sp., in particular phenazine-1-carboxylic acid (Thomashow et al., 1993); and 2,4-diacetylphloroglucinol, a normal intermediary in a pathway in bacteria which inhibits a range of fungal pathogens, and is found in a wide range of Pseudomonads (Keel et al., 1992; 1996). Phenazine has been extensively characterised in take-all biological control protection, however the effectiveness of 2,4-diacetylphloroglucinol against take-all has only been partially characterised (Raaijmakers and Weller, 1998). Pseudomonas fluorescens strain CHA0 has been also extensively studied and shown to produce an effective amount of 2,4-diacetylphloroglucinol for the suppression of black rot disease of tobacco and take-all disease of wheat (Laville et al., 1992).

Additionally, the isolated Pseudomonas strain AN5, has been shown to have a wide host range in so far as it is able to colonize the roots of a number of plant species, and is an effective biocontrol agent against take-all disease in agar plate assays, pot experiments, and in field trials (Nayudu et al. 1994b). Those authors concurred with Thomashow et al., (1993) in concluding that the dominant effects of this bacterium appeared to reside in the production of fungicides and/or fungistatic compounds, rather than in the production of siderophores.

Although other biocontrol agents have been tested for their ability to control take-all disease, such as, for example, non-pathogenic strains of G. graminis var. graminis (Wong et al., 1996), they are not a feasible method for large scale control of take-all as there is no current technology available to grow such fungi on a large scale. The cost of producing such a fungal agent and to apply same in the field is prohibitively high compared to bacterial biocontrol agents.

Genetically-manipulated Plants Expressing Disease Resistance or Tolerance:

In certain instances of disease in plants, genes which encode particular enzymes that are involved in the production of anti-fungal (i.e. fungicidal and/or fungistatic) compounds have been identified and expressed in plants to introduce tolerance or resistance thereto. In such cases, there is a requirement for the plant to be capable of expressing the introduced gene(s) and to produce the anti-fungal product from either endogenous plant metabolites, or alternatively or in addition, from exogenous substrates. As will be known to those skilled in the art, once synthesized, the anti-fungal compound must be capable of diffusion to an appropriate site of action, or actively transported, to exert its action against the invading pathogen.

One example of such protection is the expression of a gene encoding the Aspergillus niger or Talaromyces flavus glucose oxidase enzymes (EC 1.1.3.4) to control Phytopthera infestans, or Veticillium dahliae (Murray et al., 1997; Stosz et al., 1996; Wu et al., 1995; U.S. Pat. No. 5,516,671) in plants. The efficacy of this approach was based upon the involvement of hydrogen peroxide in plant defense responses in incompatible plant-pathogen interactions, wherein it may activate the production of phytoalexins and other cellular protectants, such as, for example, salicylic acid and glutathione-5-transferases; induces cross-linking of hydroxyproline-rich glycoproteins (HPGP); and is involved in triggering hypersensitive cell death in response to pathogen invasion. Additionally, hydrogen peroxide is a product of the enzymic action of glucose oxidase, which catalyzes the oxidation of glucose to δ-gluconolactone and hydrogen peroxide, and, as a consequence, the expression of glucose oxidase in plants was considered a suitable means for producing hydrogen peroxide as an anti-fungal agent. The attractiveness of this approach arose, in part, from the knowledge that the glucose oxidase gene of *Penecillium dangearii*, is involved in the effective biocontrol of *V. dahliae* by this organism (Kim et al., 1988, 1990; U.S. Pat. No. 5,516,671).

Plants expressing a range of leucine-rich repeat proteins that comprise nucleotide binding sites have also been described as providing improved protection against various diseases in plants, including rust fungi (see, for example, International Patent Application No. PCT/AU95/00240).

SUMMARY OF THE INVENTION

In work leading up to the present invention, the present inventors sought to identify an environmentally-acceptable means for the treatment of a wide range of fungal pathogens in plants and animals. The inventors identified the antifungal component produced by *Pseudomonas* strain AN5 as a sugar acid, and have determined the 110 biochemical and genetic pathway for its production. The identification of this particular antifungal agent, and the cloning of the genetic sequences required for the biosynthesis of the antifungal agent enables the development of strategies for the control of a wide range of fungal pathogens in plants and animals.

Accordingly, one aspect of the present invention is directed to a method of prophylactic or therapeutic treatment of infection by a fungal pathogen in an animal or plant comprising administering an effective amount of a sugar acid thereto for a time and under conditions sufficient to inhibit or prevent fungal growth or reproduction. In an alternative embodiment of the invention, a biocontrol agent which is capable of producing an anti-fungal effective amount of a sugar acid in the presence of an aldose substrate is administered tot the plant of animal to inhibit or prevent fungal growth or reproduction.

A second aspect of the invention provides a method of increasing the post-harvest storage of a plant product comprising applying thereto an effective amount of a sugar acid thereto for a time and under conditions sufficient to inhibit or prevent fungal growth or reproduction. In an alternative embodiment of the invention, a biocontrol agent which is capable of producing an anti-fungal effective amount of a sugar acid in the presence of an aldose substrate is applied to the plant product to inhibit or prevent fungal growth or reproduction. This aspect of the invention applies to any plant product, in particular those edible products intended for human or animal consumption, which are susceptible to rapid degradation due to fungal infection, such as, for example, fruit and vegetables, including tomatoes, apples, pears, citrus fruits, grapes, and berries, amongst others.

A third aspect of the invention provides a biocontrol agent for the treatment of a fungal infection in a plant or animal, wherein said agent comprises an isolated bacterial cell which is capable of producing a sugar acid when cultured in the presence of a carbon source comprising an aldose, and wherein said biocontrol agent is further capable of colonising the infection site. In a particularly preferred embodiment, the biocontrol agent consists of an isolate of *Pseudomonas* sp. having the characteristics of *Pseudomonas* strain AN5 rif (AGAL Accession No. NM 00/09624).

A fourth aspect of the invention provides a phytoprotective composition for the treatment of a fungal infection of a plant comprising an effective amount of a sugar acid in combination with a phytopathologically-acceptable diluent or wetting agent. The phytoprotective composition may also include a biocontrol agent which produces the sugar acid in the presence of an appropriate aldose substrate by virtue of the expression of a PQQ-dependent sugar oxidase enzyme therein.

A fifth aspect of the invention provides a composition for the treatment of a fungal infection in a human or other mammal comprising an effective amount of a sugar acid in combination with one or more pharmaceutically-acceptable carriers or diluents. As with other compositions described herein, those compositions for animal use may comprise a biocontrol agent which expresses a PQQ-dependent sugar oxidase enzyme.

The active sugar acid and/or biocontrol agent, and compositions comprising same, as described herein, can be produced by any means known to those skilled in the art. Additionally, certain sugar acids, including gluconic acid, are readily available to the public from any one of a number of sources. However, in one embodiment, the present invention clearly extends to a method of producing a sugar acid comprising introducing an isolated nucleic acid molecule which encodes a PQQ-dependent sugar acid biosynthetic enzyme to an organism and culturing said organism in the presence of an aldose substrate for a time and under conditions sufficient to produce a sugar acid. Preferably, the sugar acid is subsequently extracted from the organism. More preferably, the sugar acid is partially or substantially purified from the organism or an extract thereof.

Still another aspect of the present invention provides an isolated nucleic acid molecule comprising a nucleotide sequence which encodes one or more enzymes involved in the biosynthesis of a sugar acid or is complementary to said nucleotide sequence. Preferably, the nucleotide sequence of the invention encodes a sugar oxidase enzyme.

It will be evident from the foregoing discussion that not all cells produce PQQ as a cofactor, and, as a consequence, to produce a sugar acid in accordance with the inventive concept, it may be necessary in certain circumstances to express the enzymes required for PQQ biosynthesis, in addition to those gene(s) encoding the sugar oxidase enzyme. The present inventors have identified the PQQ operon of *Pseudomonas* strain AN5, comprising the genes the pqqA, pqqB, pqqC, pqqD, pqqE, and pqqF, which are involved in the production of PQQ. Accordingly, the present invention further provides an isolated nucleic acid molecule which comprises a nucleotide sequence encoding one or more polypeptides involved in the biosynthesis of PQQ.

A still further aspect of the invention provides a method of enhancing the tolerance of a plant to infection by a fungal pathogen comprising expressing therein a first isolated nucleic acid molecule encoding a sugar oxidase, and optionally a second isolated nucleic acid molecule encoding one or more PQQ-biosynthesis enzymes for a time and under conditions sufficient for a sugar acid to be produced by said plant, or by a cell, tissue or organ of said plant.

DETAILED DESCRIPTION OF THE PREFERRED EMBODIMENTS

Figure 1:
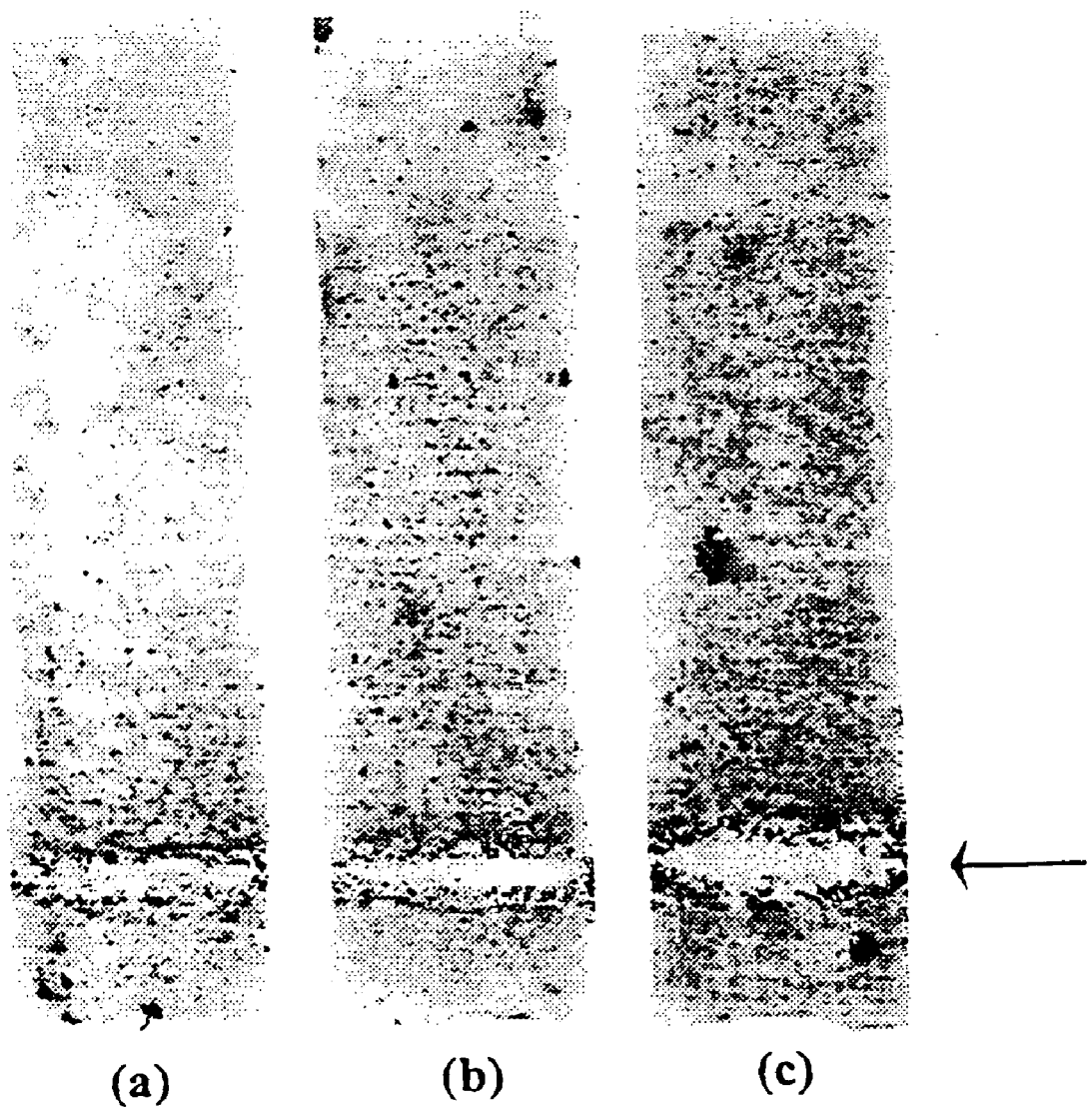
FIG. 1 is a copy of a photographic representation of a thin layer chromatogram (TLC) of an agar overlay assay showing the biological activity of the anti-take-all compound from crude extract of *Pseudomonas* strain AN5. Panel A shows a TLC performed using a solvent comprising 10% (w/v) methanol in Chloroform. Panel B shows a TLC performed using a solvent comprising 30% (w/v) methanol in chloroform. Panel C shows a TLC performed using a solvent comprising 50% (w/v) methanol in chloroform. The take-all fungus was inoculated onto the top of the TLC plate in a potato dextrose overlay agar and has the ability to grow well. An inhibition zone, indicated by the arrow, corresponds to the location of an anti-fungal agent of *Pseudomonas* strain AN5 against take-all. This anti-fungal agent is at the origin and does not migrate in the presence of any of the solvents tested.

The present invention is directed to a method of prophylactic or therapeutic treatment of infection by a fungal pathogen in an animal or plant or a cell, tissue or organ thereof, comprising administering an effective amount of a sugar acid thereto for a time and under conditions sufficient to inhibit or prevent fungal growth or reproduction.

By "fungal pathogen" is meant any fungus or yeast which is capable of infecting a plant or animal, including a human, in a manner so as to reduce productivity or health of said plant or animal, or to cause disease, morbidity or mortality therein. In the present context, the term "fungal pathogen" further includes any of the true fungi or yeasts which infect plants or animals.

The present invention is further useful in the delay or prevention of food spoilage due to infection of fungal pathogens, particularly in the case of plant products (i.e. fruits, and vegetables), in which case, the sugar acid or composition comprising same may be sprayed directly onto the produce to partially or completely inhibit fungal growth under standard storage conditions, thereby increasing the post-harvest life of produce.

In a preferred embodiment, the present invention is directed to the prophylactic or therapeutic treatment of infection by a fungal pathogen selected from the group consisting of: *Alternaria* spp.; *Armillaria mellae*; *Arthrobotrys oligosporus*; *Boletus granulatus*; *Botritis cinerea*; *Botrytis fabae*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; and *Verticillium dahliae*.

More preferably, the present invention is directed to the prophylactic or therapeutic treatment of infection by a fungal pathogen of plants, even more preferably a fungal pathogen of plants selected from the group consisting of *Alternaria* spp.; *A. mellae*; *A. oligosporus*; *B. granulatus*; *B. cinerea*; *B. fabae*; *C. purpurea*; *C. ribicola*; *E. purpurescens*; *F. annosus*; *F. oxysporum*; *G. graminis* var. *tritici*; *G. cingulata*; *G. juniperi-virginianae*; *M. fructicola*; *P. alfalfae*; *P. infestans*; *P. sulphureus*; *Puccinia* spp.; *S. apiicola*; *Ustilago* spp.; *V. inaequalis*; and *V. dahliae*; and still more preferably, a fungal pathogen of monocotyledonous plants selected from the group consisting of *C. purpurea*; *G. graminis* var *tritici*; *Puccinia* spp.; and *Ustilago* spp.

In a particularly preferred embodiment, the present invention provides a method of treatment of infection of a plant by the fungal pathogen *Gaeumannomyces graminis* var *tritici*, comprising administering an effective amount of a sugar acid thereto for a time and under conditions sufficient to inhibit or prevent-fungal growth or reproduction. The plant to which this embodiment of the invention is directed may be any of the natural hosts of *G. graminis*, and preferably, a wheat plant or a close relative or progenitor species of wheat, such as, for example, *Triticum aestivum*, *T. tauschii*, or *Hordeum vulgare*, amongst others.

As used herein, the term "sugar acid" shall be taken to refer to the carboxylic acid derivative of any monosaccharide, disaccharide or polysaccharide, whether or not said carboxylic acid derivative is in the anionic form, or a salt, or contains other substituent groups added thereto, such as, for example, one or more phosphorous atoms or phosphorous-containing moieties. The term "sugar acid" further encompass any mono-carboxylic acid, dicarboxylic acid or tricarboxylic acid derivatives of an aldose.

Preferably, but not necessarily exclusively, the sugar acid is not a keto-acid. Additionally, whilst acceptable, it is particularly preferred that the sugar acid used in the performance of the invention is not in the lactone form. Accordingly, notwithstanding that the lactone form may be present in any composition comprising the sugar acid, the invention preferably extends to the use of the sugar acid and not the lactone in the inventive method described herein.

Preferably, the sugar acids contemplated for use in accordance with the present invention are aldonic, aldaric, or uronic acids. Those skilled in the art are aware that aldonic acids can be produced naturally or synthetically by the oxidation of an aldose at the aldehydic carbon atom, either using weak oxidizing agents, such as, for example, sodium hypoiodate, or alternatively, specific enzymes. In contrast, the aldaric acids are produced using stronger oxidising agents which act at both the aldehydic carbon atom and the carbon atom bearing the primary hydroxyl group, whereas in the uronic acids only the carbon atom bearing the primary hydroxyl group is oxidised. Preferably, the sugar acid used in the performance of the present invention is a derivative of D-glucose, in particular the aldonic acid gluconic acid; and/or the aldaric acid, glucaric acid; and/or the uronic acid glucuronic acid. The use of sugar acid derivatives of D-galactose, in particular galactonic acid and/or galactaric acid, and/or galacturonic acid, is also contemplated by the present invention. The use of sugar acid derivatives of D-mannose, in particular mannonic acid and/or mannonaric acid, and/or mannonuronic acid, is also contemplated by the present invention. Alternatively, the present invention also contemplates the use of a sugar acid selected from the group consisting of malic acid, and ascorbic acid, in the performance of the present invention.

In a particularly preferred embodiment, the present invention is directed to the use of gluconic acid and/or mannonic acid and/or galacturonic acid, and, more particularly, to the use of gluconic acid.

By "effective amount" of a sugar acid is meant an amount which is effective in preventing the growth and/or reproduction of the fungal pathogen, or alternatively, killing the fungal pathogen, without significant adverse effects on the health or viability of the plant of animal to which the sugar acid is administered. The effective amount of sugar acid administered will vary depending upon the nature of the fungal pathogen, the sugar acid being administered, and the mode in which the sugar acid is provided (i.e. in the form of a biocontrol agent or purified sugar acid, amongst others). Persons skilled in the art will be capable of determining an effective amount of any sugar acid to be administered, by standard empirical means, the only requirement being the availability of a suitable bioassay for the fungal pathogen. Such methods will be well-known to those skilled in the art, or are described herein. In general, it is not essential to the performance of a bioassay which tests the growth and/or viability of a fungal pathogen to include host cells which the fungus normally infects, provided that appropriate in vitro culture conditions have been established which permit the growth of the fungal pathogen. If no such assay is available, then bioassays may be conducted using appropriate animal or plant hosts, or isolated cells or tissues, as a source of nutrient for the fungal pathogen. In the particular case of human subjects, bioassays, other than those used in human trials, may be conducted using appropriate animal models, in particular a mammalian host of a fungal pathogen of humans, such as, for example, mice, rats, or rabbits, or isolated mammalian cells, in particular cultured fibroblast cells.

In this regard, the present inventors have found the agar plug assay described by Poplawsky et al. (1988) to be particularly useful for determining the growth and/or viability of a wide range of fungal pathogens of plants, including *Alternaria* spp.; *A. mellae*; *A. oligosporus*; *B. granulatus*; *B. cinerea*; *E. purpurescens*; *F. annosus*; *G. graminis* var *tritici*; *M. fructicola*; *P. sulphureus*; and *V. dahliae*.

To determine the efficacy of any particular sugar acid in controlling a fungal pathogen, various dosages of the sugar acid are tested for their ability to slow or inhibit fungal growth, or alternatively, to kill the fungal pathogen, compared to the effectiveness of one or more negative and/or positive control compounds. Suitable negative controls include the use of a suitable growth medium comprising, as a substitute for the sugar acid being tested, the corresponding aldose sugar, or corresponding lactone, or alternatively, the absence of the test compounds from the growth medium. A suitable positive control includes the use of a suitable growth medium comprising gluconic acid at a concentration which is known to inhibit the growth of the fungal pathogen being tested, or which is known to kill the fungal pathogen being tested.

Once the parameters have been established within which a particular sugar acid will inhibit fungal growth and/or reproduction, it is preferred for the sugar acid to be tested further to ensure that it does not produce adverse effects or severe contraindications on the host when used within those parameters.

The purified sugar or biocontrol agent is generally administered, in the case of therapeutic treatments, to the site of infection. Alternatively, in the case prophylactic treatments, the purified sugar acid or biocontrol agent will generally be administered to a probable infection site, or at least in a form suitable for transport to a probable infection site.

Various modes of administration of the sugar acid to a plant or animal will be known to those skilled in the art, and the present invention is not to be limited by the nature of the formulation used. Because non-modified sugar acids are soluble hydrophilic molecules, sprays, solutions, lotions and topical ointments for administration are readily formulated without the need for chemical solvent-based solubilising agents, which may be detrimental to the plant or animal cells.

Conveniently, the sugar acid is administered to a plant or plant cell in the form of an aqueous solution, in particular a spray, applied to the infection site and/or the soil or other growth medium. The application of sugar acids in solid or powdered form is not to be excluded. Optionally, a wetting agent, such as, for example, a non-ionic detergent, may be included to facilitate access of the sugar acid to the fungal pathogen. Wetting agents comprising ionic detergents which are alkaline in nature are less desirable, because they may have a pH-neutralising effect, or even an alkalating effect, on the sugar acid. As will be known to those skilled in the art, the hyphae of fungal pathogens may penetrate the epidermal layers of the plant tissues, and, as a consequence, the wetting agent may further assist in the penetration of the sugar acid to underlying cells of the root, stem, or leaf. Additionally, the epidermal cells of many plant tissues are covered with a waxy layer, which may be penetrated using various wetting agents. Accordingly, the wetting agent may assist the sugar acid in reaching those cells of the plant which are to be treated.

In the treatment of infections by fungal pathogens of animals and humans, the present invention is primarily directed to the treatment of those infections of epidermal cells and keratinised tissues, including the skin, genitalia, and nails. Accordingly, the administration of topical lotions, ointments, and powders is to be preferred for such infections. Those skilled in the art will readily be in a position to produce such formulations, which may include various additional pharmaceutical carriers and/or excipients which are of use in the formulation of skin products.

In addition to being provided in the form of a purified sugar acid, the active ingredient (i.e. the sugar acid) may be administered to the plant or animal in the form of a biocontrol agent which produces the sugar acid when cultured in the presence of a carbon source comprising an aldose. Such biocontrol agents may be isolated from natural sources, or consist of any one or more mutants or derivatives of a naturally-occurring organism, or a genetically-engineered organism, the only requirements being that the biocontrol agent is capable of colonising the tissues or cells which are normally infected by the fungal pathogen, and is capable of producing an anti-fungal effective amount of a sugar acid. Preferably, the biocontrol agent is further limited in respect of the cell types which it is capable of colonising in the host, such as, for example, a non-pathogenic form of the pathogen in question.

In a preferred embodiment, the biocontrol agent consists of a non-pathogenic bacterium.

Wherein the sugar acid is for treatment of an infection of animals and/or humans, it is particularly preferred that the biocontrol agent consists of a non-pathogenic strain of 110 bacterium selected from the group consisting of *Streptococcus* sp., *Staphylococcus* sp., *Escherichia coli*, *Acidophilius* sp. and *Lactobacillus* sp. For the treatment of urethral, intra vaginal and anal infections, non-pathogenic strains of *Escherichia coli*, *Acidophilius* sp. and *Lactobacillus* sp. are preferred.

For the treatment of plants, it is preferred that the biocontrol agent consists of a non-pathogenic strain of bacterium selected from the group consisting of *Agrobacterium tumefaciens*, *Agrobacterium rhizogenes*, *Agrobacterium radiobacter*, *Frankia* sp., and *Pseudomonas* sp. In the case of *Agrobacterium* sp., the strain should optimally be one which does not cause adverse crown gall disease, or produce phytohormones, such as, for example, auxins, gibberellins, or cytokinins, at levels which are capable of inducing atypical developmental patterns in the plant. Strains suitable for use in the performance of the present invention include, for example, derivatives of *A. tumefaciens* strain LBA4404; derivatives of *A. tumefaciens* strain AGL1; and *Pseudomonas* strain AN5 and derivatives thereof.

In a particularly preferred embodiment, the biocontrol agent consists of an isolate of *Pseudomonas*, exemplified by *Pseudomonas* strain AN5 (Nayudu et. al, 1994b) or a mutant or derivative thereof. These strains have been shown by the present inventors to have particular utility in the protection of plants against the take-all fungus, *G. graminis* var. *tritici*, by virtue of their ability to colonize the root rhizosphere of a wheat plant or other host of *G. graminis* var. *tritici*, and to produce a sugar acid when cultured in the presence of an aldose substrate.

As applied to a biocontrol agent which produces a sugar acid in its native state, such as, for example, a mutant or derivative of *Pseudomonas* strain AN5, reference herein to "mutants" and "derivatives" shall be taken to mean those mutants with increased colonizing ability and/or increased sugar acid biosynthetic capacity and/or increased sugar acid secretion, compared to the naturally-occurring isolate, including any auxotrophic mutants, replication mutants and recombinant strains that have been produced by the insertion of additional genetic material, such as, for example, extra-chromosomal plasmids or integrated DNA, or transposable genetic elements. As used herein, the term "secretion" shall be taken to include both active transport and diffusion processes which result in the extracellular localisation of a sugar acid which is produced by a cell.

As applied to bacteria which do not have the capacity to produce and/or secrete sugar acids in their native state, such as, for example *A. tumefaciens*, the terms "mutant" and "derivative" shall be taken to mean that the natural isolate has been subjected to mutagenesis, and/or genetically-engineered, to produce and/or secrete the sugar acid when grown on an appropriate aldose substrate. This may be achieved, for example, by genetically-engineering or mutating an organism to express a pyrroloquinoline-quinone-dependent (PQQ-dependent) sugar oxidase enzyme.

As applied to bacteria which do not have the capacity to colonise the same cells as the fungal pathogen, the terms "mutant" and "derivative" shall be taken to mean that the natural isolate has been subjected to mutagenesis, and/or genetically-engineered, to have the capacity to colonize the same cells or tissues as those which the fungal pathogen infects.

Particularly useful mutants and derivatives further include those organisms having altered cell membrane or cell wall components. According to this embodiment, the present invention provides a rifampicin-resistant derivative of *Pseudomonas* strain AN5, designated hereinafter as "*Pseudomonas* strain AN5 rif" (AGAL Accession No. NM 00/09624), which exhibits higher anti-fungal activity against *G. graminis* var. *tritici* than the naturally-occurring isolate *Pseudomonas* strain AN5.

*Pseudomonas* strain AN5 rif has been deposited with the National Measurements Institute (NMI) formerly Australian Government Analytical Laboratories (AGAL), at 1 Suakin street Pymble 2073, New South Wales, Australia, on 28 Jan. 2000, under the provisions of the Budapest Treaty on the International Recognition of the Deposit of Microorganisms for the Purposes of Patent Procedure, and assigned AGAL Accession No. NM 00/09624. This deposit of *Pseudomonas* strain AN5 rif is not to be construed as any admission that such a deposit is required to satisfy the requirements of 35 U.S.C. § 112. In compliance with the 37 C.F.R. § 1.808, the applicants assure that: (1) access to the deposit will be available during pendency of the patent application making reference to the deposit to a person skilled in the art and determined by the Director to be entitled under § 1.14 and 35 U.S.C. § 122 to a sample of the deposit; and (2) all restrictions imposed by the depositor on the availability to the public of the deposited material will be irrevocably removed upon the granting of the patent.

In a further preferred embodiment of the invention, *Pseudomonas* strain AN5 or *Pseudomonas* strain AN5 rif are further improved for use as a biocontrol agent in performing the present invention, by the introduction of additional copies of the genetic sequences which, when expressed, enable the organism to produce sugar acids. Such improvements may be produced by means of standard transformation/transfection procedures for bacteria, or transposon mutagenesis, amongst other procedures known to those skilled in the art.

Means for producing mutants will be well-known to those skilled in the art, and include the use of chemical and physical mutagens, and transposon mutagenesis, amongst others. Particularly preferred chemical mutagens include EMS and methanesulfonic acid ethyl ester. As will be known to those skilled in the art, EMS generally introduces point mutations into the genome of a cell in a random non-targeted manner, such that the number of point mutations introduced into any one genome is proportional to the concentration of the mutagen used. Accordingly, in order to identify a particular mutation, large populations of cells are generally treated with EMS and the effect of the mutation is then screened in the mutated cells or, more usually, the progeny cells thereof. Methods for the application and use of chemical mutagens such as EMS are well-known to those skilled in the art.

Preferred physical mutagens include the irradiation of cells, in particular ultraviolet and gamma irradiation of cells, to introduce point mutations into one or more genes present in the genome of the cell, or alternatively, to create chromosomal deletions in the genome. Methods for the application and use of such mutagens are well-known to those skilled in the art.

Insertional mutagenesis may be achieved by introducing a DNA molecule which encodes genes for the biosynthesis of sugar acids, into one or more genes present in the genome of the cell in an expressible format, such that the ability of the cell to convert aldose to sugar acid is enhanced. Alternatively, a nucleic acid molecule which is capable of inactivating a negative regulator of a gene required for the biosynthesis of a sugar acid may be introduced into the cell.

Preferred DNA molecules for introducing genes into cells, in particular bacterial or plant cells, include transposon molecules, and T-DNA molecules. The use of transposons carries the advantage of providing a marker for the cloning of genetic material capable of encoding molecules required to catalyse or otherwise facilitate the conversion of a carbon source to a corresponding sugar acid. Many transposons are known for use in bacterial and plant systems, including Tn10 (bacterial), Tn5 (bacterial), Spm (plant), Ac/Ds (plant), and DSG (plant), and their use is well-documented.

Methods for the production of appropriate biocontrol agents using are described herein.

The biocontrol agents, including mutant and derivatives, described herein are of utility in the preparation of compositions for the treatment of fungal infections in plants and animals, and the present invention clearly extends to any and all such uses. For example, the organisms may be used in fermentation or other culture conditions, to produce the sugar acid, which may be then be extracted from the cells using conventional extraction and/or purification procedures, or alternatively, secreted into the growth medium.

The present invention further provides a phytoprotective composition for the treatment of a fungal infection of a plant comprising an effective amount of a sugar acid in combination with a phytopathologically-acceptable diluent or wetting agent.

The wetting agent may be any compound which is capable of permeating the epidermal layer and/or the waxy layer of a plant tissue, such as, but not limited to, a non-ionic detergent.

The concentration of the sugar acid in such compositions will vary depending upon the fungal pathogen, the progression of the disease, the tolerance of the plant to mild acidification, and the soil type. For plants which are less tolerant to acidification, a weaker acid, such as, for example, gluconic acid, may be preferred, in which case, a higher concentration of the sugar acid may be required to alleviate symptoms on the plant. Stronger acids, such as glucuronic acid and glutaric acid, may be used at lower concentrations than gluconic acid, however the suitability of any particular sugar acid for a particular fungal infection should be determined empirically in trials prior to large-scale applications. Such trials are well within the ken of those skilled in the art.

Preferably, the concentration of sugar acid in the phytoprotective compositions of the invention is in the range of about 0.001% (w/v) to about 1% (w/v) sugar acid, more preferably in the range of about 0.01% (w/v) to about 1% (w/v) sugar acid, and more preferably in the range of about 0.01% (w/v) to about 0.5% (w/v) sugar acid, and even more preferably in the range of about 0.01% (w/v) to about 0.1% (w/v) sugar acid.

In an alternative embodiment, the phytoprotective composition comprises a biocontrol agent which produces the sugar acid in the presence of an appropriate aldose substrate by virtue of the expression of a PQQ-dependent sugar oxidase enzyme therein. Additionally, the phytoprotective composition may be in the form of a spray, emulsion, or dry powder.

The present invention further provides a composition for the treatment of a fungal infection in a human or other mammal comprising an effective amount of a sugar acid in combination with one or more pharmaceutically-acceptable carriers or diluents. As with other compositions described herein, those compositions for animal use may comprise a biocontrol agent which expresses a PQQ-dependent sugar oxidase enzyme. The composition of the present invention is particularly directed to the treatment of conditions associated with epidermal and sub-cutaneous infections, such as, for example, those conditions caused by the dermatophytes *T. rubrum*, *T. mentagrophytes*, *E. floccosum*, *M. canis*, *C. albicans*, and *P. orbiculare* (*M. furfur*). Accordingly, it is preferred that the composition of the invention be formulated for topical application, including intra vaginal, intra-anal, intra-nasal, and intra-oral uses. Emulsions, lacquers, spray powders, and dry powders are also contemplated by the invention. Except insofar as any conventional media or agent is incompatible with an active ingredient, use thereof in the therapeutic compositions is contemplated. Supplementary active ingredients can also be incorporated into the compositions.

In light of the nature of the active ingredient and the intended application, it is preferred that compositions for topical application are formulated so as to have a pH in the range of about 2.0 to about 7.0, more preferably in the range of about 2.0 to about 5.0, and more preferably in the range of about 2.5 to about 4.0.

Creams, lotions, ointments, and tinctures comprising the sugar acid of the invention, which are intended for topical or intra-vaginal or intra-anal or intra-aural use, can be prepared in a base comprising any standard lotion or ointment for dermatological use, such as, for example, vanishing cream, sorbolene, glycerol and fatty acid esters thereof, liquid polyethylene glycols including polyoxyethylglycol, ethylene glycol, butylated hydroxanisole, liquid paraffin, dimethicone, sorbitan, cetyl palmitate or other fatty acid, polysorbate, and mixtures thereof.

In such topical compositions, alcohols and other organic solvents are not generally required to maintain solubility of the sugar acid, which is hydrophilic. However, as the present invention includes modified sugar acids which have altered hydrophilicity compared to their non-modified counterparts, and because such compositions may include less-soluble components, the invention also encompasses the use of non-aqueous base compositions.

Powders are generally prepared using a base of zinc oxide, talc, or other homogeneous powder base.

Lacquers for nail applications are generally prepared in a lacquer base comprising, for example, methacrylic acid copolymer, glycerol triacetate, butyl acetate, ethyl acetate, and ethanol.

Spray powders are prepared using a powdered or aqueous base, such as, for example, talc, sorbitan, or a fatty acid; and will also generally comprise a propellant, such as, for example, ethanol, propane, or butane.

Under ordinary conditions of storage and use, these preparations will further contain a preservative to prevent the growth of microorganisms. In any event, it must be stable under the conditions of manufacture and storage and should be preserved against the contaminating action of microorganisms, at least until point-of-sale. This may be achieved, for example, by using various known anti-bacterial and anti-fungal agents, including parabens, chlorobutanol, phenol, sorbic acid, thimerosal, benzoic acid, phenethyl alcohol, and benzyl alcohol, amongst others. The use of antibiotics, such as, for example, tetracycline, rifampicin, ampicillin, penicillin, and streptomycin, or a derivative thereof, is also encompassed by the present invention.

The compositions of the invention may further include another anti-fungal compound to provide broad cross-protection against several different pathogens. Such other anti-fungal compounds include, for example, bifonazole, clotrimazole, econazole nitrate, miconazole nitrate, terbafine hydrochloride, and amorolfine hydrochloride, amongst others.

Preferably, the formulations are prepared by incorporating the active sugar acid compounds, or a biocontrol agent producing same, in the required effective amount, in an appropriate base with various of the other ingredients enumerated above, as required, preferably followed by filter-sterilization.

The active sugar acid and/or biocontrol agent, and compositions comprising same, as described herein, can be produced by any means known to those skilled in the art. Additionally, certain sugar acids, including gluconic acid, are readily available to the public from any one of a number of sources. Alternatively, the sugar acid may be purified partially or completely using any one of a number of procedures known to those skilled in the art, including chromatographic procedures, such as, for example, separations based on charge, size, hydrophobicity, or affinity. Phase separation techniques, thin layer chromatography, and separations using silica gel are particularly contemplated by the invention. Column chromatographic procedures may be carried out conveniently under conditions of high pressure (e.g. HPLC).

In one embodiment, the sugar acid is produced by introducing an isolated nucleic acid molecule which encodes a PQQ-dependent sugar acid biosynthetic enzyme to an organism and culturing said organism in the presence of an aldose substrate for a time and under conditions sufficient to produce a sugar acid. Preferably, the sugar acid is subsequently extracted from the organism or the culture medium. More preferably, the sugar acid is partially or substantially purified from the culture medium, the organism or an extract thereof.

The nucleotide sequence which encodes one or more enzymes involved in the biosynthesis of a sugar acid or is complementary to said nucleotide sequence is preferably derived from *Pseudomonas* sp.

Preferably, the nucleotide sequence of the invention encodes a sugar oxidase enzyme.

As used herein, the term "sugar oxidase" shall be taken to refer to a PQQ-dependent enzyme, or a PQQ-dependent enzyme complex, or a number of different enzymes which act in the same biochemical pathway wherein at least one of said enzymes is PQQ-dependent, to convert an aldose to a sugar acid. For example, the term "sugar oxidase" includes the action of an oxidase enzyme, with or without a lactonase enzyme, to convert glucose or galactose to any one or more of their corresponding aldonic, aldaric, or uronic acids (i.e. gluconic acid; glucaric acid; glucaronic acid; and galactonic acid). As will also be known to those skilled in the art, the glucose oxidase enzyme solus is capable of converting glucose to δ-gluconolactone, which may subsequently be oxidised non-enzymatically to a sugar acid. Notwithstanding that the velocity of such a non-enzymatic oxidation reaction is slow compared to the enzyme-catalysed reaction, the activity of glucose oxidase combined with such non-enzymatic oxidation of a lactone to a sugar acid clearly falls within the scope of the term "sugar acid", subject to the requirement that a sugar acid is actually produced as the active anti-fungal compound. The term "sugar oxidase" further encompasses the action of a dehydrogenase enzyme with or without a lactonase enzyme, to convert D-glucose to any one or more of the corresponding sugar acids, gluconic acid and/or glucaric acid and/or glucaronic acid.

By "PQQ-dependent" is meant that the sugar oxidase requires PQQ as a cofactor for optimum enzyme activity. As will be known to those skilled in the art, PQQ is a metal-dependent enzyme cofactor produced primarily by bacteria, wherein the metal is generally calcium, or copper. The advantage of using a PQQ-dependent sugar oxidase in the performance of the invention is that the production of PQQ is not linked to glycolysis, and, as a consequence, there is less glycolytic load on a transgenic cell expressing such a sugar oxidase, compared to the expression of an FAD- or NAD-dependent enzyme.

Preferably, the isolated nucleic acid molecule of the invention comprises sequence of nucleotides set forth in SEQ ID NO: 1 or the nucleotide sequence of the sugar oxidase gene present in cosmid pMN M53 (AGAL Accession No. NM 00/09622).

For the purposes of nomenclature, cosmid pMN M53 comprises the nucleotide sequence of a sugar oxidase-encoding gene derived from *Pseudomonas* strain AN5. To produce cosmid pMN M53, a mutant strain of *Pseudomonas* strain AN5 was produced by Tn5: uidA insertional mutagenesis of *Pseudomonas* strain AN5, and screening for bacterial cells which had lost activity against *G. graminis* var. *tritici* and did not produce anti-fungal effective amounts of sugar acid when cultured in the presence of aldose substrate. A sub-genomic fragment of the mutant strain was obtained and sub-cloned into the cosmid pLAF R3, which includes a gene conferring tetracycline-resistance to cells containing the cosmid. The resulting cosmid clone, 110 designated pMN M53, contains sufficient structural gene information of *Pseudomonas* sp. to confer on any prokaryotic cell harboring this cosmid, or a derivative nucleic acid molecule thereof having the sugar oxidase-encoding region thereof, the ability to synthesise sugar acids from aldose. Cosmid clone pMN M53 has been deposited with the Australian Government Analytical Laboratories (AGAL), at 1 Suakin street Pymble 2073, New South Wales, Australia, on 27 Jan. 2000, under the provisions of the Budapest Treaty on the International Recognition of the Deposit of Microorganisms for the Purposes of Patent Procedure, and assigned AGAL Accession No. NM 00/09622.

The nucleotide sequence set forth in SEQ ID NO: 1 relates to the terminal 757 bp of a sugar oxidase-encoding gene contained in cosmid clone pMN M53. To obtain the nucleotide sequence set forth in SEQ ID NO: 1, a sequencing primer was used which annealed to the end of the Tn5: uidA insertion in cosmid clone pMN M53. The nucleotide sequence set forth in SEQ ID NO: 1 has less than 50% nucleotide sequence identity overall to any known genes, as determined by BLAST search analysis. However, BLAST search analysis revealed that a fragment of 23 nucleotides in length derived from SEQ ID NO: 1, comprising nucleotides 553 to 575 of this sequence, has absolute identity to the glucose dehydrogenase-encoding genes of *E. coli*, or *Pantoea citrea*. These limited homologies indicate that the nucleotide sequence present in cosmid clone pMN M53 is unlikely to comprise a glucose dehydrogenase-encoding gene, however is most likely involved in glucose metabolism. Moreover, functional expression data indicate that there is sufficient structural gene sequence in cosmid clone pMN M53 to confer on any prokaryotic cell harboring this cosmid, or a derivative nucleic acid molecule thereof having the sugar oxidase-encoding region thereof, the ability to convert glucose to gluconic acid. Clearly, the bacterial sugar oxidase gene is not highly conserved with any other known sugar oxidase, such as, for example, the glucose oxidase genes of *Talaromyces flavus* or *Aspergillus niger*.

Accordingly, the present invention clearly extends to homologues, analogues and derivatives of the *Pseudomonas* sp. nucleotide sequence present in the deposited cosmid designated pMN M53, or the nucleotide sequence present in SEQ ID NO: 1. The full-length nucleotide sequence of the *Pseudomonas* sp. nucleotide sequence present in cosmid pMN M53 is particularly contemplated by the present invention.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence identity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

Particularly preferred homologues, analogues or derivatives include any one or more isolated nucleic acid molecules selected from the following:

(i) an isolated nucleic acid molecule which comprises a nucleotide sequence which is at least about 50% identical to at least about 30 contiguous nucleotides of SEQ ID NO: 1 or a complementary sequence thereto;

(ii) an isolated nucleic acid molecule which comprises a nucleotide sequence which is at least about 50% identical to at least about 30 contiguous nucleotides of the *Pseudomonas* gene sequence contained in the cosmid clone pMN M53 (AGAL Accession No. NM 00/09622);

(iii) an isolated nucleic acid molecule which is capable of hybridising under at least low stringency conditions to at least about 30 contiguous nucleotides of SEQ ID NO: 1 or a complementary sequence thereto;

(vi) an isolated nucleic acid molecule which is capable of hybridising under at least low stringency conditions to at least about 30 contiguous nucleotides of the *Pseudomonas* gene sequence contained in the cosmid clone pMN M53 (AGAL Accession No. NM 00/09622); and (vii) an isolated nucleic acid molecule which comprises a nucleotide sequence which is degenerate to SEQ ID NO: 1 or the *Pseudomonas* gene sequence contained in the cosmid clone pMN M53 (AGAL Accession No. NM 00/09622). Preferably, such homologues will be of a sufficient length and sequence identity to the exemplified sequence and deposited clone to encode a polypeptide having sugar oxidase activity. Preferably, because the nucleic acid molecule of the invention encodes a PQQ-dependent enzyme, and this cofactor is prevalent in bacterial cells, the homologue, analogue or derivative thereof is obtained from a bacterial source, more preferably a *Pseudomonas* sp.

However, the present invention clearly contemplates shorter molecules than those which are full-length, which are at least useful in identifying further sugar oxidase-encoding nucleotide sequences falling within the scope of the invention described herein. Preferably, the homologue, analogue or derivative is at least about 100 nucleotides in length, more preferably at least about 500 nucleotides in length, and even more preferably, comprises at least about 1–10 kb of nucleotides in length.

Preferably, the percentage identity to the nucleotide sequence of SEQ ID NO: 1 or the deposited clone, is at least about 60%, more preferably at least about 70%, even more preferably at least about 80%, and more preferably at least about 90%, or 95%, or 99%. In determining whether or not two nucleotide sequences fall within a particular percentage identity limitation recited herein, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, 1984).

The homologues, analogues and derivatives may be obtained by any standard procedure known to those skilled in the art, such as by nucleic acid hybridization (Ausubel et al, 1987), polymerase chain reaction (McPherson et al, 1991) screening of expression libraries using antibody probes (Huynh et al, 1985) or by functional assays.

In nucleic acid hybridizations, genomic DNA, mRNA or cDNA or a part of fragment thereof, in isolated form or contained within a suitable cloning vector such as a plasmid or bacteriophage or cosmid molecule, is contacted with a hybridization-effective amount of a nucleic acid probe derived from SEQ ID NO: 1 or the deposited clone, for a time and under conditions sufficient for hybridization to occur and the hybridized nucleic acid is then detected using a detecting means. Detection is performed preferably by labelling the probe with a reporter molecule capable of producing an identifiable signal, prior to hybridization. Preferred reporter molecules include radioactively-labelled nucleotide triphosphates and biotinylated molecules.

Preferably, variants of the genes exemplified herein, including genomic equivalents, are isolated by hybridisation under medium or more preferably, under high stringency conditions, to the probe.

For the purposes of defining the level of stringency, a low stringency is defined herein as being a hybridisation and/or a wash carried out in 6×SSC buffer, 0.1% (w/v) SDS at 28° C. or alternatively, as exemplified herein. Generally, the stringency is increased by reducing the concentration of SSC buffer, and/or increasing the concentration of SDS and/or increasing the temperature of the hybridisation and/or wash. A medium stringency comprises a hybridisation and/or a wash carried out in 0.2×SSC–2×SSC buffer, 0.1% (w/v) SDS at 42° C. to 65° C., while a high stringency comprises a hybridisation and/or a wash carried out in 0.1×SSC–0.2× SSC buffer, 0.1% (w/v) SDS at a temperature of at least 55° C. Conditions for hybridisations and washes are well understood by one normally skilled in the art. For the purposes of further clarification only, reference to the parameters affecting hybridisation between nucleic acid molecules is found in Ausubel et al. (1992), which is herein incorporated by reference.

In the polymerase chain reaction (PCR), a nucleic acid primer molecule comprising at least about 20 nucleotides in length, and more preferably at least 30 nucleotides in length, derived from SEQ ID NO: 1 or the deposited clone, is hybridized to a nucleic acid template molecule and specific nucleic acid molecule copies of the template are amplified enzymatically as described in McPherson et al, (1991), which is incorporated herein by reference.

In expression screening of cDNA libraries or genomic libraries, protein- or peptide-encoding regions are placed operably under the control of a suitable promoter sequence in the sense orientation, expressed in a prokaryotic cell or eukaryotic cell in which said promoter is operable to produce a peptide or polypeptide, screened with a monoclonal or polyclonal antibody molecule or a derivative thereof against one or more epitopes of a sugar oxidase polypeptide and the bound antibody is then detected using a detecting means, essentially as described by Huynh et al (1985) which is incorporated herein by reference. Suitable detecting means according to this embodiment include $^{125}$I-labelled antibodies or enzyme-labelled antibodies capable of binding to the first-mentioned antibody, amongst others.

It will be evident from the foregoing discussion that the bacterial sugar oxidase of the invention is a PQQ-dependent enzyme. However, because not all cells produce PQQ as a cofactor, in order to produce a sugar acid in accordance with the inventive concept, it may be necessary in certain circumstances to also express the enzymes required for PQQ biosynthesis, in addition to those gene(s) encoding the sugar oxidase enzyme. The present inventors have identified the PQQ operon of *Pseudomonas* strain AN5, comprising the genes the pqqA, pqqB, pqqC, pqqD, pqqE, and pqqF, which are involved in the production of PQQ.

To produce a functional PQQ cofactor in a cell, it is necessary to ensure that a sufficient number of PQQ-biosynthetic genes are expressed therein to convert one or more of the precursors of PQQ, in the PQQ biosynthetic pathway, to PQQ, and to insert an appropriate metal ion, such as, for example, Cu(II) or $Ca^{2+}$, therein. The appropriate substrate, and metal ion, must be either endogenous to the cell, or alternatively, provided exogenously to the cell. In this regard, certain cells may be deficient in only one or two or three or four of the PQQ-biosynthetic genes described herein, and, as a consequence, the present invention clearly encompasses the use of only a subset of the five genes exemplified herein. Additionally, if a precursor of PQQ which is later in the biosynthetic pathway is provided to the cell, then the genes which encode enzymes acting earlier in the pathway may not be required. For example, the immediate precursor of PQQ may be provided to a cell which expresses only the pqqE gene, and a functional PQQ cofactor may still be produced therefrom. Such modifications will be readily apparent to those skilled in the art.

Accordingly, the present invention further provides an isolated nucleic acid molecule which comprises a nucleotide sequence encoding one or more polypeptides involved in the biosynthesis of PQQ. Preferably, but not necessarily, such sequences are derived from a bacterial cell, such as, for example, *Pseudomonas* sp. Several bacterial PQQ-biosynthesis genes have been described and are readily available from public sources.

In a particularly preferred embodiment, the present invention provides a novel isolated nucleic acid molecule comprising one or more of the pqqA, pqqB, pqqC, pqqD, pqqE, and pqqF genes of *Pseudomonas* strain AN5.

Preferably, the isolated nucleic acid molecule of the invention comprises sequence of nucleotides set forth in any one of SEQ ID NOs: 2 to 6, or the nucleotide sequence of the sugar oxidase gene present in cosmid pMN-L2 (AGAL Accession No. NM 00/09621).

For the purposes of nomenclature, cosmid pMN-L2 comprises the nucleotide sequence of the pqqA, pqqB, pqqC, pqqD, pqqE, and pqqF genes derived from 30 *Pseudomonas* strain AN5. To produce cosmid pMN-L2, a mutant strain of *Pseudomonas* strain AN5 was produced by Tn5: uidA insertional mutagenesis of *Pseudomonas* strain AN5, and screening for bacterial cells which had lost activity against *G. graminis* var. *tritici*. A sub-genomic fragment of the mutant strain was obtained and sub-cloned into the cosmid pLAF R3, which includes a gene conferring tetracycline-resistance to cells containing the cosmid. The resulting cosmid contains sufficient structural gene information of *Pseudomonas* sp. to produce PQQ from its natural substrate in a bacterial cell, to confer on any prokaryotic cell harboring this cosmid, or a derivative nucleic acid molecule thereof having these genes therein, the ability to produce PQQ. Cosmid clone pMN-L2 has been deposited with the Australian Government Analytical Laboratories (AGAL), at 1 Suakin street Pymble 2073, New South Wales, Australia, on 27 Jan. 2000, under the provisions of the Budapest Treaty on the International Recognition of the Deposit of Microorganisms for the Purposes of Patent Procedure, and assigned AGAL Accession No. NM 00/09621.

The nucleotide sequence set forth in SEQ ID NOs: 2 to 6 relate to the pqqA, pqqB, pqqC, pqqD, pqqE, and pqqF genes contained in cosmid clone pMN-L2. In particular, SEQ ID NO: 2 consists of the full-length pqqA gene and a fragment of the pqqB gene of *Pseudomonas* strain AN5, obtained using a sequencing primer derived from a conserved region in bacterial pqqB genes. The nucleotide sequence set forth in SEQ ID NO: 3 consists of a fragment of the pqqC gene of *Pseudomonas* strain AN5, obtained using a sequencing primer derived from a conserved region in bacterial pqqC genes. The nucleotide sequence set forth in SEQ ID NO: 4 consists of a fragment of the pqqD gene of *Pseudomonas* strain AN5, obtained using a sequencing primer derived from a conserved region in bacterial pqqE genes. The nucleotide sequence set forth in SEQ ID NO: 5 consists of a fragment of the pqqE gene of *Pseudomonas* strain AN5, obtained using a sequencing primer which annealed to the end of the Tn5: uidA insertion in cosmid clone pMN-L2. The nucleotide sequence set forth in SEQ ID NO: 6 consists of a fragment of the pqqF gene of *Pseudomonas* strain AN5, and the intergenic region between pqqA and pqqF, and was obtained using a sequencing primer derived from a conserved region in bacterial pqqB genes.

The nucleotide sequence set forth in any one of SEQ ID NOs: 2, 3, 5, and 6 have less than 90% nucleotide sequence identity overall to any known PQQ-biosynthesis genes, whilst there is no significant nucleotide sequence identity to SEQ ID NO:4 overall, as determined by BLAST search analysis. However, BLAST search analysis revealed that smaller fragments, of less than 42 contiguous nucleotides in length derived from any one of SEQ ID NOs: 2 to 6, have greater identities to prior PQQ-biosynthesis genes.

Accordingly, the present invention clearly extends to homologues, analogues and derivatives of the *Pseudomonas* sp. nucleotide sequence present in the deposited cosmid designated pMN-L2 (AGAL Accession No. NM 00/09621), or the nucleotide sequence present in any one of SEQ ID NOs: 2 to 6. The full-length nucleotide sequence of the *Pseudomonas* sp. pqqA, pqqB, pqqC, pqqD, pqqE, and pqqF genes derived from cosmid pMN-L2 is particularly contemplated by the present invention.

Particularly preferred homologues, analogues or derivatives include any one or more isolated nucleic acid molecules selected from the following:

(i) an isolated nucleic acid molecule which comprises a nucleotide sequence which is at least about 90% identical to at least about 50 contiguous nucleotides of any one of SEQ ID NOs: 2 to 6 or a complementary sequence thereto;

(ii) an isolated nucleic acid molecule which comprises a nucleotide sequence which is at least about 90% identical to at least about 50 contiguous nucleotides of the *Pseudomonas* gene sequence contained in the cosmid clone pMN-L2 (AGAL Accession No. NM 00/09621);

(iii) an isolated nucleic acid molecule which is capable of hybridising under at least low stringency conditions to at least about 50 contiguous nucleotides of any one of SEQ ID NOs: 2 to 6 or a complementary sequence thereto;

(iv) an isolated nucleic acid molecule which is capable of hybridising under at least low stringency conditions to at least about 50 contiguous nucleotides of the *Pseudomonas* gene sequence contained in the cosmid clone pMN-L2 (AGAL Accession No. NM 00/09621); and (v) an isolated nucleic acid molecule which comprises a nucleotide sequence which is degenerate to any one of SEQ ID NOs: 2 to 6 or the *Pseudomonas* gene sequence contained in the cosmid clone pMN-L2 (AGAL Accession No. NM 00/09621).

Preferably, such homologues will be of a sufficient length and sequence identity to the exemplified sequence and deposited clone to encode functional PQQ-biosynthesis enzymes. However, the present invention clearly contemplates shorter molecules than those which are full-length, which are at least useful in identifying further PQQ-biosynthesis genes falling within the scope of the invention described herein. Preferably, the homologue, analogue or derivative is at least about 100 nucleotides in length, more preferably at least about 500 nucleotides in length, and even more preferably, comprises at least about 1–10 kb of nucleotides in length.

Preferably, the percentage identity to the nucleotide sequence of SEQ ID NO: 1 or the deposited clone, is at least about 90%, more preferably at least about 95%, even more preferably at least about 97%, and more preferably at least about 99%, as determined using standard nucleotide sequence analysis software.

Preferably, the hybridization stringency is at least moderate stringency, and more preferably a high stringency hybridization is employed to identify new sequences.

As with homologues, or the sugar oxidase-encoding genes of the invention described herein, homologues, analogues and derivatives of a PQQ biosynthesis gene may be obtained by any standard procedure known to those skilled in the art, such as by nucleic acid hybridization (Ausubel et al, 1987), polymerase chain reaction (McPherson et al, 1991) screening of expression libraries using antibody probes (Huynh et al, 1985) or by functional assays.

Although not intending to limit the present invention to any one theory or mode of action, it is proposed that *Pseudomonas* strain AN5 or a derivative thereof, in particular *Pseudomonas* strain AN5 rif (AGAL Accession No. NM 00/09624), or another organism carrying the sugar oxidase-encoding nucleotide sequences described herein (optionally with the PQQ-biosynthesis gene nucleotide sequences hereinbefore described), oxidizes an aldose such as D-glucose at the aldehydic carbon atom to form the corresponding sugar acid, wherein the first step in this conversion is catalysed by the glucose oxidase (GOD) activity of the PQQ-dependent sugar oxidase, involving the formation a lactone, and wherein the second step in this conversion is catalysed by the lactonase activity of the PQQ-dependent sugar oxidase.

Accordingly, in those embodiments of the invention which do not employ an organism in which the genes of the invention are known to be expressed, it is necessary to introduce those genes to the organism in an expressible format. Because the genes of the invention are bacterially-derived, the sugar oxidase-encoding genes present in cosmid pMN M53, and the PQQ operon of cosmid pMN-L2 contain the requisite regulatory sequences for expression in most bacterial cells, in particular *Pseudomonas* sp.

The present invention further provides for the configuration of the inventive genes described herein in an expressible format in both prokaryotic and eukaryotic cells. In most cases, this requires positioning the structural protein-encoding regions of the genes described herein in operable connection with one or more regulatory sequences required for expression in a particular cell type, or under a particular set of environmental conditions.

For expression in eukaryotic cells, the structural gene sequences of the invention may be further modified by the inclusion of intron sequences from known eukaryotic genes to improve the stability of mRNA encoded by said structural genes, or otherwise increase expression. For example, to improve expression in plant cells, the intron sequences of the first intron of the rice actin gene, or the maize Adh1 gene, or the *Arabidopsis thaliana* Adh1 gene are particularly useful.

It is also within the scope of the invention to include modifications of the exemplified nucleotide sequences, or modifications of the genes present in the microorganism deposits, which have been made for the purposes of adapting the codon usage of the bacterial gene to that which is optimum in the organism into which the gene is to be expressed. Such codon usage modifications are well known in the art and may be readily carried out by a skilled person. Accordingly, degenerate sequences to the exemplified sequences are particularly contemplated by the present invention.

Accordingly, the present invention clearly extends to the use of gene constructs designed to facilitate the introduction and/or expression of the nucleic acid molecule of the invention.

To express the nucleic acid molecule in a prokaryotic cell, such as a bacterial cell, or a eukaryotic cell, such as an insect cell, mammalian cell, plant cell or yeast cell, it is preferred that the structural protein-encoding region be placed operably under the control of a strong universal promoter, or a promoter sequence which is capable of regulating expression in response to various external stimuli. Persons skilled in the art will be in a position to select appropriate promoter sequences for expression of the nucleic acid molecule without undue experimentation.

Reference herein to a "promoter" is to be taken in its broadest context and includes the transcriptional regulatory sequences of a classical eukaryotic genomic gene, including the TATA box which is required for accurate transcription initiation, with or without a CCMT box sequence and additional regulatory elements (i.e. upstream activating sequences, enhancers and silencers) which alter gene expression in response to developmental and/or external stimuli, or in a tissue-specific manner. In the context of the present invention, the term "promoter" also includes the transcriptional regulatory sequences of a classical prokaryotic gene, in which case it may include a −35 box sequence and/or a −10 box transcriptional regulatory sequences.

In the present context, the term "promoter" is also used to describe a synthetic or fusion molecule, or derivative which confers, activates or enhances expression of said sense molecule in a cell. Preferred promoters may contain additional copies of one or more specific regulatory elements, to further enhance expression and/or to alter the spatial expression and/or temporal expression of a nucleic acid molecule to which it is operably connected. For example, copper-responsive regulatory elements may be placed adjacent to a heterologous promoter sequence driving expression of a nucleic acid molecule to confer copper inducible expression thereon.

Placing a nucleic acid molecule under the regulatory control of a promoter sequence means positioning said molecule such that expression is controlled by the promoter sequence. A promoter is usually, but not necessarily, positioned upstream or 5' of a nucleic acid molecule which it regulates. Furthermore, the regulatory elements comprising a promoter are usually positioned within 2 kb of the start site of transcription of the structural protein-encoding nucleotide sequences, or a chimeric gene comprising same. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Promoters suitable for use in gene constructs of the present invention include those promoters derived from the genes of viruses, yeasts, moulds, bacteria, insects, birds, mammals and plants which are capable of functioning in isolated cells derived from bacteria, yeasts, fungi, animals, or plants, including monocotyledonous and/or dicotyledonous plants, and/or cells, tissues and organs derived from the isolated cells. The promoter may regulate gene expression constitutively, or differentially with respect to the tissue in which expression occurs or, with respect to the developmental stage at which expression occurs, or in response to external stimuli such as physiological stresses, pathogens, or metal ions, amongst others.

Examples of promoters useful in performing this embodiment include the CaMV 35S promoter, NOS promoter, octopine synthase (OCS) promoter, *Arabidopsis thaliana* SSU gene promoter, napin seed-specific promoter, $P_{32}$ promoter, BK5-T imm promoter, lac promoter, tac promoter, phage lambda $\lambda_L$ or $\lambda_R$ promoters, CMV promoter (U.S. Pat. No. 5,168,062), lacUV5 promoter, SV40 early promoter (U.S. Pat. No. 5,118,627), SV40 late promoter (U.S. Pat. No. 5,118,627), adenovirus promoter, baculovirus P10 promoter, or polyhedrin promoter (U.S. Pat. Nos. 5,243,041, 5,242, 687, 5,266,317, 4,745,051 and 5,169,784), bacteriophage T7 promoter, bacteriophage T3 promoter, SP6 promoter, SV40 early promoter, RSV-LTR promoter, SCSV promoter, SCBV promoter and the like. In addition to the specific promoters identified herein, cellular promoters for so-called housekeeping genes, including the actin promoters, or promoters of histone-encoding genes, are useful.

Numerous vectors having suitable promoter sequences for expression in bacteria have been described, such as for example, pKC30 (λL: Shimatake and Rosenberg, 1981), pKK173-3 (tac: Amann and Brosius, 1985), pET-3 (T7: Studier and Moffat, 1986) or the pQE series of expression vectors (Qiagen, CA), amongst others.

In a particularly preferred embodiment, the promoter is derived from a *Pseudomonas* strain AN5 gene present in cosmid clones pMN M53 (AGAL Accession No. NM 00/09622) or pMN-L2 (AGAL Accession No. NM 00/09621).

The gene construct may further comprise a terminator sequence and be introduced into a suitable host cell where it is capable of being expressed.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the nopaline synthase (NOS) gene terminator of *Agrobacterium tumefaciens*, the terminator of the Cauliflower mosaic virus (CaMV) $^{35}$S gene, the zein gene terminator from *Zea mays*, the Rubisco small subunit (SSU) gene terminator sequences and subclover stunt virus (SCSV) gene sequence terminators, amongst others. Those skilled in the art will be aware of additional promoter sequences and terminator sequences which may be suitable for use in performing the invention. Such sequences may readily be used without any undue experimentation.

The gene constructs of the invention may further include an origin of replication sequence which is required for replication in a specific cell type, for example a bacterial cell, when said gene construct is required to be maintained as an episomal genetic element (eg. plasmid or cosmid molecule) in said cell. Preferred origins of replication include, but are not limited to, the f1-ori and co/E1 origins of replication.

The gene construct may further comprise a selectable marker gene or genes that are functional in a cell into which said gene construct is introduced.

As used herein, the term "selectable marker gene" includes any gene which confers a phenotype on a cell in which it is expressed to facilitate the identification and/or selection of cells which are transfected or transformed with a gene construct of the invention or a derivative thereof.

Suitable selectable marker genes contemplated herein include the ampicillin resistance (Amp'), tetracycline resistance gene (Tc'), bacterial kanamycin resistance gene (Kan'), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

Numerous expression vectors suitable for the present purpose have been described and are readily available.

In a preferred embodiment, the subject method comprises the additional first step of transforming the cell, tissue, organ or organism with a nucleic acid molecule of the invention, in particular the sugar oxidase-encoding sequences with or without additional PQQ-biosynthesis genes, or one or more gene constructs comprising same. As discussed supra this nucleic acid molecule may be contained within a gene construct. The nucleic acid molecule or a gene construct comprising same may be introduced into a cell using any known method for the transfection or transformation of said cell. In the case of eukaryotic organisms, a whole organism may be regenerated from a single transformed cell, using any method known to those skilled in the art.

By "transfect" is meant that the introduced nucleic acid molecule is introduced into said cell without integration into the cell's genome.

By "transform" is meant that the introduced nucleic acid molecule or gene construct comprising same or a fragment thereof is stably integrated into the genome of the cell.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al., 1984), PEG-mediated uptake to protoplasts (Armstrong et al., 1990) microparticle bombardment, electroporation (Fromm et al., 1985), microinjection of DNA (Crossway et al., 1986), microparticle bombardment of tissue explants or cells (Christou et al., 1988; Sanford, 1988), vacuum-infiltration of tissue with nucleic acid, or in the case of plants, T-DNA-mediated transfer from *Agrobacterium* to the plant tissue as described essentially by An et al. (1985), Herrera-Estrella et al. (1983a, 1983b, 1985).

For microparticle bombardment of cells, a microparticle is propelled into a cell to produce a transformed cell. Any suitable biolistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using biolistic transformation procedures, the gene construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

Alternatively, wherein the cell is derived from a multicellular organism and where relevant technology is available, a whole organism may be regenerated from the transformed cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centres.

The term "embryogenesis", as used herein, means a process by which shoots and roots develop together in a concerted fashion (not sequentially), whether from somatic cells or gametes.

The regenerated transformed plants may be propagated by a variety of means, such as by clonal propagation or classical breeding techniques. For example, a first generation (or T1) transformed plant may be selfed or crossed to another T1 plant and homozygous second generation (or T2) transformants selected. In the case of woody crops, such as citrus and grapes and other plants, which are not readily selfed to make homozygous plants, clonal derivatives of primary transformants will need to be crossed to each other to produce homozygous T2 plants. The T2 plant may then be further propagated through classical breeding techniques.

The regenerated transformed organisms contemplated herein may take a variety of forms. For example, they may be chimeras of transformed cells and non-transformed cells; clonal transformants (e.g., all cells transformed to contain the expression cassette); and grafts of transformed and untransformed tissues (e.g., in plants, a transformed root stock grafted to an untransformed scion).

It will be apparent from the preceding discussion that the transformed organisms have a variety of applications by virtue of their ability to express a PQQ-dependent sugar oxidase. In fact, such transformed organisms have applications in any field where treatment of a fungal infection is required, as discussed supra. In the case of transformed plants, these may themselves exhibit enhanced resistance or tolerance to a fungal pathogen.

Accordingly, the present invention clearly provides a method of enhancing the tolerance of a plant to fungal infection comprising expressing in said plant, or a cell, tissue or organ thereof, an isolated nucleic acid molecule which encodes a PQQ-dependent sugar oxidase according to any embodiment described herein. Preferably, nucleotide sequences comprising one or more PQQ-biosynthesis genes are also expressed in the plant and, optionally if required, an appropriate substrate for the activity of the expressed PQQ-biosynthetic protein is provided to the transformed plant to ensure that a functional cofactor is formed.

Preferably, the method further comprises the first step of introducing nucleic acid encoding the sugar oxidase and PQQ-biosynthesis genes to the plant cell.

Preferably, the inventive method further comprises the step of regenerating a whole plant from the transformed cell.

By "enhanced tolerance" is meant that the plant is less susceptible to a sustained infection by the fungal pathogen, and/or is less likely to develop disease following an initial infection by the fungus, because the fungal pathogen is unable to grow uninhibited on the transformed plant.

This aspect of the invention clearly extends to those progeny of the transformed plants which also express the introduced nucleic acid molecules.

The present invention is further described with reference to the accompanying Examples and drawings.

EXAMPLE 1

Use of *Pseudomonas* Strain AN5 as a Biocontrol Agent Against *G. graminis* var *tritici* (Take-all)

In small scale field trials, the inventors were able to consistently increase wheat yield at different dry-land trial sites in New South Wales, Australia, from between 12% to 36% (P<0.05), by application of *Pseudomonas* strain AN5 (Table 1).

TABLE 1

Summary of wheat yields (Kg/plot)

| Trial Δ | AN5 | Ba$_1$ | Ba$_2$ | Ba$_3$ | Pf5 | Control |
|---|---|---|---|---|---|---|
| Goolgowi | 10.23 | 11.00* | n.t | n.t | 8.86^ | 9.07 |
| Forbes | n 10.76 | 10.28 | 11.28* | 10.95* | 9.70^ | 9.12 |
| West Wyalong | 5.70* | 5.88* | 5.17 | 5.41 | 4.65^ | 4.32 | nt, not tested;
^ not significant;
*significant at p < 0.01.

Subsequently, the Harden District Rural Services (HRS) group has established large scale trials using *Pseudomonas* strain AN5 in acre plots at a trial site at Harden, New South Wales, Australia. Prior to the commencement of the trial, there was significant take-all disease at this site. Following biocontrol treatment using *Pseudomonas* strain AN5, the treated plot monitored through the wheat growing season exhibited 30% to 40% suppression of disease, as determined by the level of white head formation and visual scoring of symptoms on the roots. Additionally, determination of wheat crop yield using a bio-informatic satellite-based global positioning system (GPS) to accurately determine the location of the harvested crop, and an NIH image analyser, indicated that there was 20% increase in wheat yield due to biocontrol protection conferred by *Pseudomonas* strain AN5.

In biocontrol protocols, the survival of *Pseudomonas* strain AN5 bacteria on the roots of plants, and in the soil, is one of the most crucial factors in effective biological control protection. A typical survival pattern of *Pseudomonas* strain AN5 bacteria on the roots of wheat over a season is that they decrease in numbers. The rate of decrease of *Pseudomonas* strain AN5 is related to the moisture content of the soil. In different soil types, and at different field sites, the numbers of *Pseudomonas* strain AN5 present in the soil decreases over a number of seasons. High numbers of the bacteria build up at the start of the season (approximately $10^6$–$10^7$ per gram of wheat root), with the numbers dropping off towards the drier end of the season. In very dry years, a much more dramatic fall in the numbers of bacteria is observed on the wheat root and this correlates well with loss of biological control protection.

EXAMPLE 2

Biocontrol of *Botrytis fabae* (Chocolate Spot Fungus) Using *Pseudomonas* Strain AN5

Chocolate spot (causative agent *Botrytis fabae*) is a significant disease of faba beans. Currently, fungicides are applied a number of times during the growing season.

We have shown that *Pseudomonas* strain AN5 is effective against the chocolate spot disease of faba bean, and is able to suppress the growth of *B. fabae*, in bioassays carried out in vitro.

In the glasshouse, the present inventors were able to induce chocolate spot by spraying *B. fabae* fungus onto the plant. Symptoms of the disease were observable within a few days of spraying. A scale was devised to score the severity of disease symptoms, and, using this scale, plants sprayed with biocontrol bacteria comprising *Pseudomonas* strain AN5, either before or after inoculation with *B. fabae*, were shown to have reduced symptoms by up to 90%, compared to untreated plants. The present inventors have further shown that up to 95% protection against chocolate spot disease can be obtained by inoculation with *Pseudomonas* strain AN5.

Furthermore, we have shown that sugar acids, such as gluconic acid, suppress the growth and/or reproduction of *B. fabae* fungus in bioassays carried out in-vitro. Accordingly, it is within the scope of the present invention to produce transgenic faba bean plants which produce sugar acids, using the methods described herein, to enhance tolerance of faba beans to *B. fabae*.

EXAMPLE 3

Identification of an Anti-Fungal Compound in *Pseudomonas* sp. Which is Active Against *G. graminis* var *tritici* (Take-all)

Microbiological and Molecular Biological Methods

Standard methods were employed as described by Nayudu and Holloway, (1981), Nayudu and Rolfe (1987), Nayudu et. al., (1994a) and Nayudu et al., (1994b).

Bacterial Strains

*Pseudomonas* strains designated AN5, Pf5, and AN5 rif, possess anti-fungal activity against take-all, and were used in all experiments, unless otherwise stated. The mutant strains AN5-MN1 and AN5-MN2 do not possess significant anti-fungal activity and were used as negative controls unless otherwise stated.

Bioassay Procedure

A modification of the agar plug assay (Poplawsky et al., 1988) was used to assay for bioactivity of extracts of *Pseudomonas* strain AN5, or derivative strains thereof, against take-all fungus, wherein an agar overlay assay was used to test activity of specific fractions. This assay involves macerating the take-all fungus grown in Potato Dextrose (PD) broth and seeding it to a Potato Dextrose Agar (PDA) overlay. This PDA overlay was poured onto thick PDA plates. Fractions to be tested for activity were spotted on top of the overlay, and the plates were dried and incubated at 16° C. for 3–5 days.

Extraction and Analysis of the Anti-Fungal Compound

*Pseudomonas* sp. strain AN5 bacteria were cultured in 250 ml flasks, at 25° C., for two days, using potato dextrose broth as the growth medium. Following this culture period, 150 ml isopropanol was added to 90 ml of cell culture, and the solution mixed by shaking for 15 minutes, after which time cells were collected by centrifugation for 10 minutes at 5,000 rpm. The supernatant was removed and evaporated using a rotavapor at 40° C. The crude evaporate was dissolved in 100 ml of ethanol (30 ml three times). To the ethanol insoluble triturate, 50 ml water was added, followed by 50 ml acetone, to precipitate proteinaceous material.

The resulting suspension was centrifuged and a total of 0.02 ml, drawn from the supernatant as well as from ethanolic solution, was applied by a micropipette (Gilson Pipette) to a silica gel G F254 TLC plate (Aszalos et al., 1968). Thin layer chromatography was performed on the crude extract, using several different solvent systems:

1. methanol;
2. methanol:chloroform [1:9 (v/v)];
3. chloroform;
4. pyridine: water [1:1 (v/v)];
5. pyridine: water: ethanol [1:1:1 (v/v/v)];
6. pyridine: water: ethanol [1:1:3 (v/v/v)];
7. 2-propanol: water [17:3 (v/v)];
8. 2-propanol: water [4:1 (v/v)];
9. 2-propanol: water [7:3 (v/v)];
10. acetone: water [9:1 (v/v)];
11. acetone:n-butanol:acetic acid:water [8:0.5:0.5:1 (v/v/v/v)];
12. n-propanol: water [7:1 (v/v)];
13. n-propanol: water [7:1.5 (v/v)];
14. n-propanol: ethyl acetate: water [5:1:4 (v/v/v)];
15. n-propanol: ethyl acetate: water [5:2:3 (v/v/v)];
16. n-propanol: ethyl acetate: water [5.5:2:2.5 (v/v/v)];
17. methyl acetate: 2-propanol: water [18:1:1 (v/v/v)];
18. 2-propanol: ethyl acetate: water [1:1:2 (v/v/v)]; and
19. 2-propanol: ethyl acetate: water [6:1:3 (v/v/v)].

This large number of solvent systems was used in attempts to improve the resolution of the active anti-fungal compound of *Pseudomonas* sp. strain AN5 on silica TLC plates.

To determine whether any particular compound in TLC plates possessed anti-fungal activity, the bioassay described supra was modified such that the PDA overlay, seeded with take-all fungus, was poured onto the TLC plates and incubated for a week at 16° C. Active fractions were identified by the appearance of a clearance zone in the plates, within an opaque background of cultured fungus.

Using this bioassay, the compound having anti-fungal activity in *Pseudomonas* strain AN5 against take-all fungus did not migrate from the origin using the solvent systems comprising methanol; methanol:chloroform [1:9 (v/v)]; or chloroform. The biological activity was tested on TLC plates as well as after scratching bands and extracting the compounds from plates on PDA plates. In particular, there was a clearance zone at the origins of these TLC plates, as well as on PDA plates having the same active fraction (FIG. 1).

Using TLC in conjunction with this bioassay, the bioactive anti-fungal compound of *Pseudomonas* strain AN5 was shown to have an Rf value of about 0.7, when a solvent system comprising pyridine: water: ethanol [1:1:1 (v/v/v)], or pyridine: water: ethanol [1:1:3 (v/v/v)] was used, however resolution of the compound was poor in this system also.

Silica Gel Reverse Phase Thin Layer Chromatography (SGRPTLC) using a solvent system comprising acetonitrile:methanol:water was unable to produce better resolution than these TLC solvent systems.

We subsequently tested solvent systems usually applied to the separation of carbohydrates, in particular organic solvents of binary or ternary composition. Water is an indispensable component of such solvent systems, because water-free solvents, or solvents having low water content, produce diffuse spots, as were obtained for crude extracts of AN5 and mutants thereof (Ghebregzabher et al., 1976).

Figure 2A:
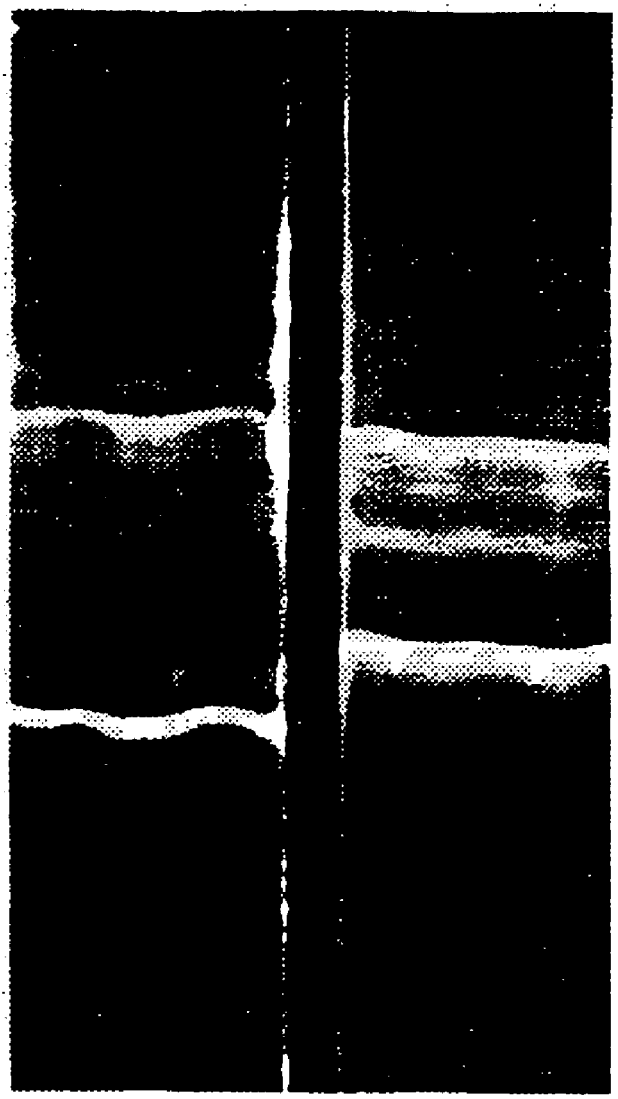
FIG. 2A is a copy of a photographic representation of silica gel 60 $F_{254}$ TLC plates using a solvent system comprising n-propanol:ethyl acetate:water [5:2:3 (v/v)], showing the separation of compounds in crude extracts of *Pseudomonas* strain AN5 (panel a) and the mutant strain AN5-MN1 (panel b). The data indicate differences in the simple sugars produced by the mutant strain AN5-MN1, compared to *Pseudomonas* strain AN5.
Figure 2B:
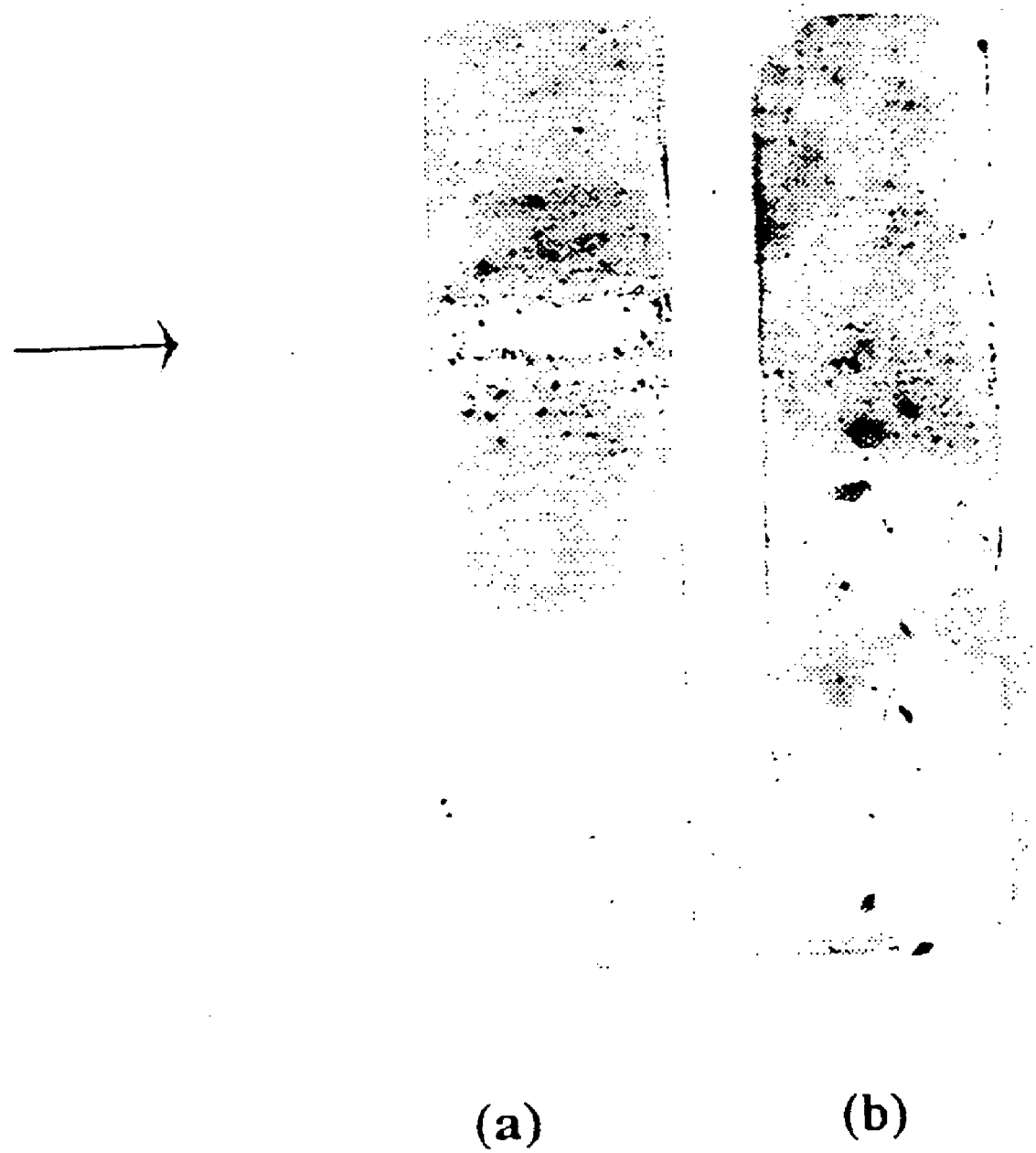
FIG. 2B is a copy of a photographic representation of the TLC plates of FIG. 2A in an agar overlay assay, showing the biological activity of a compound produced by *Pseudomonas* strain AN5 (panel a), but not the mutant strain AN5-MN1 (panel b), against the take-all fungus, as evidenced by the arrow (inhibition zone). The sovent conditions are the same as shown in FIG. 2A.

From the large number of solvent systems listed supra, only one system, n-propanol: ethyl acetate: water has been successful in resolving the anti-fungal component of *Pseudomonas* strain AN5 in TLC procedures, wherein optimum results were obtained using n-propanol: ethyl acetate: water [5:2:3 v/v/v]. Data are shown in FIG. 2. This solvent system is normally used for separating hexoseamines (Ghebregzabher et al., 1976; Gal, 1968). Accordingly, these data suggested that the anti-fungal compound of *Pseudomonas* strain AN5 might be a carbohydrate-like molecule.

EXAMPLE 4

Purification of an Anti-Fungal Compound in *Pseudomonas* sp. Which is Active Against *G. graminis* var *tritici* (Take-all)

Adsorption chromatography on columns or on TLC plates is a useful method for separation and purification of simple sugars, sugar derivatives and oligosaccharides. However, this technique is time consuming and frequently results in poor resolution due to band tailing. Therefore, the inventors followed the substantially faster technique of "flash chromatography" to purify the compound (Still et al., 1978). Flash chromatography is basically an air pressure driven hybrid of medium pressure and short column chromatography.

Biologically-active extracts of *Pseudomonas* strain AN5, or the mutants AN5-MN1 or AN5-MN2, were separated on silica columns, using SGRPTLC with the n-propanol: ethyl acetate: water [5:2:3 v/v/v] solvent system, essentially as described by Still et al. (1978).

Partially-purified extracts (i.e. column fractions) of *Pseudomonas* strain AN5, or the mutants AN5-MN1 or AN5-MN2, were separated on TLC plates using the standardised solvent system (i.e. n-propanol: ethyl acetate: water [5:2:3 v/v/v]) and different bands were scratched and extracted. The extracted compounds of *Pseudomonas* strain AN5 were tested for their anti-fungal activity on PDA plates, using the bioassay described in the preceding Example. The bioassay was also performed using the modified procedure on TLC plates to confirm the activity of the band of interest. The active fractions, which have similar active band on TLC plates, were pooled for further analysis.

Figure 3A:
FIG. 3A is a copy of a photographic representation of a silica gel 60 $F_{254}$ TLC plate using a solvent system comprising n-propanol:ethyl acetate:water [5:2:3 (v/v)], showing silica column fractions of *Pseudomonas* strain AN5. Numbering at the bottom of each lane indicates the fraction number collected from the silica column; and C indicates a crude extract of *Pseudomonas* strain AN5, which was used as starting material for the silica column.
Figure 3B:
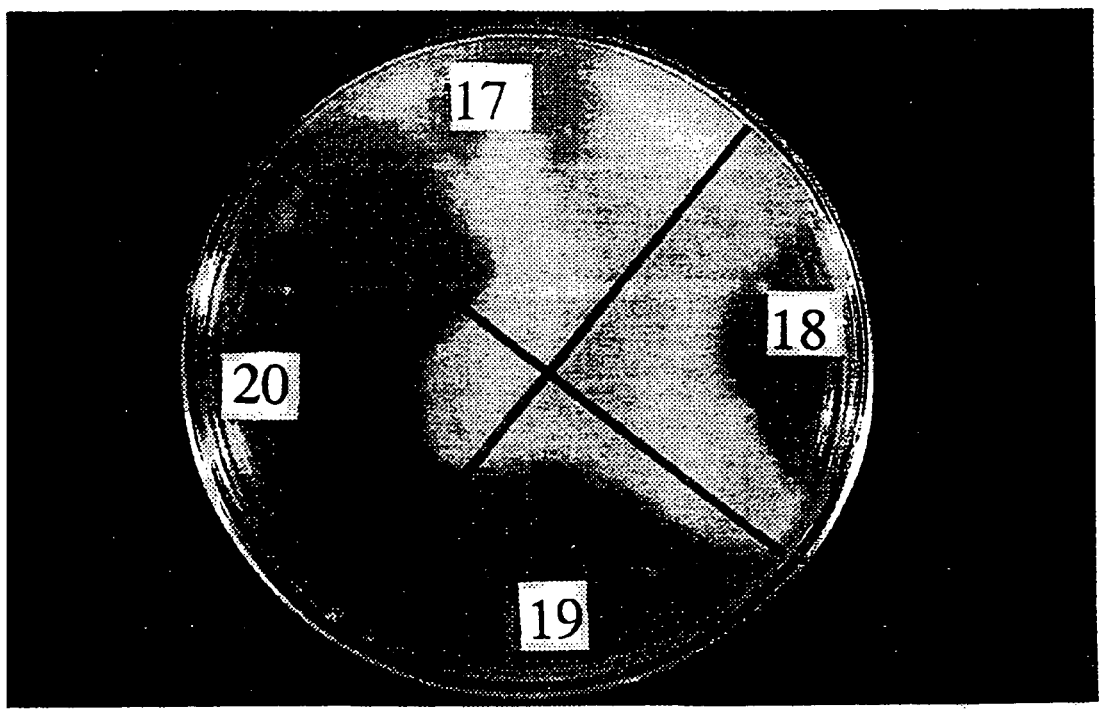
FIG. 3B is a copy of a photographic representation of a PDA plate inoculated with take-all fungus, showing the biological activity of silica column fractions 17 to 20 shown in FIG. 3A against the take-all fungus. Numbering corresponds to the silica column fraction number. The zone of clearing indicates inhibition of fungal growth, compared to the white patches where the fungus grows. Data indicate that fractions 17 to 20 are active against take-all fungus, and that fractions 19 and 20 contain the highest activity.

As shown in FIG. 3A, bioactive column fractions of *Pseudomonas* strain AN5 were also shown to possess bioactivity using TLC, wherein they migrated to a point corresponding to an Rf value of about 0.75 on TLC. In contrast, the identical silica gel fractions, extracted from the biologically-inactive mutants AN5-MN1 or AN5-MN2, were inactive in the bioassay conducted on TLC plates with a PDA overlay, suggesting that the active fraction of *Pseudomonas* strain AN5 extracts was acting specifically.

However, the silica gel column fractions obtained from extracts of *Pseudomonas* strain AN5 were not considered to comprise pure compounds, because many bands were observed on TLC plates containing these fractions (FIG. 3A).

Figure 4:
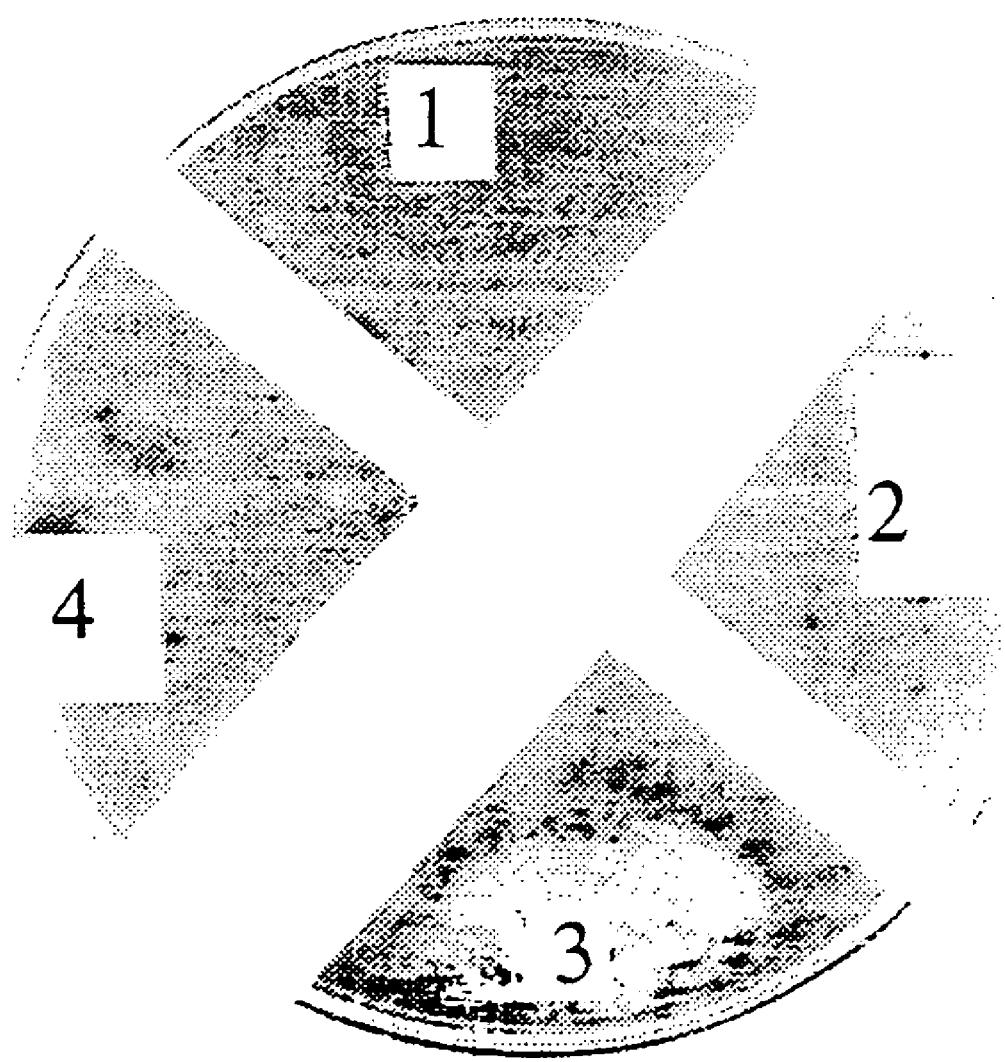
FIG. 4 is a copy of a photographic representation of a PDA plate in an agar overlay bioassay, showing the activity against take-all fungus of silica column fractions 17 to 20 of *Pseudomonas* strain AN5, following their re-chromatography on TLC as described in the legend to FIG. 3A. The active fractions were eluted in four samples (based on Rf value), numbered 14. Only fraction 3 (Rf value 0.75) was active against take-all fungus, as evidenced by the inhibition zone.

The bioactive compound was further purified by separating pooled active fractions of *Pseudomonas* strain AN5 on TLC and excising the bands of interest. The compounds in these excised bands were tested for activity against take-all on PDA plates, and shown to possess bioactivity (FIG. 4).

EXAMPLE 5

Chemical Characterisation of an Anti-Fungal Compound in *Pseudomonas* sp. Which is Active Against *G. graminis* var *tritici* (Take-all) as a Sugar Acid The active anti-fungal fractions from *Pseudomonas* strain AN5 were further analysed by $^1$H NMR, $^{13}$C NMR, and the mass spectra of compounds determined, to determine the structure of the biologically-active compound.

Figure 5A:
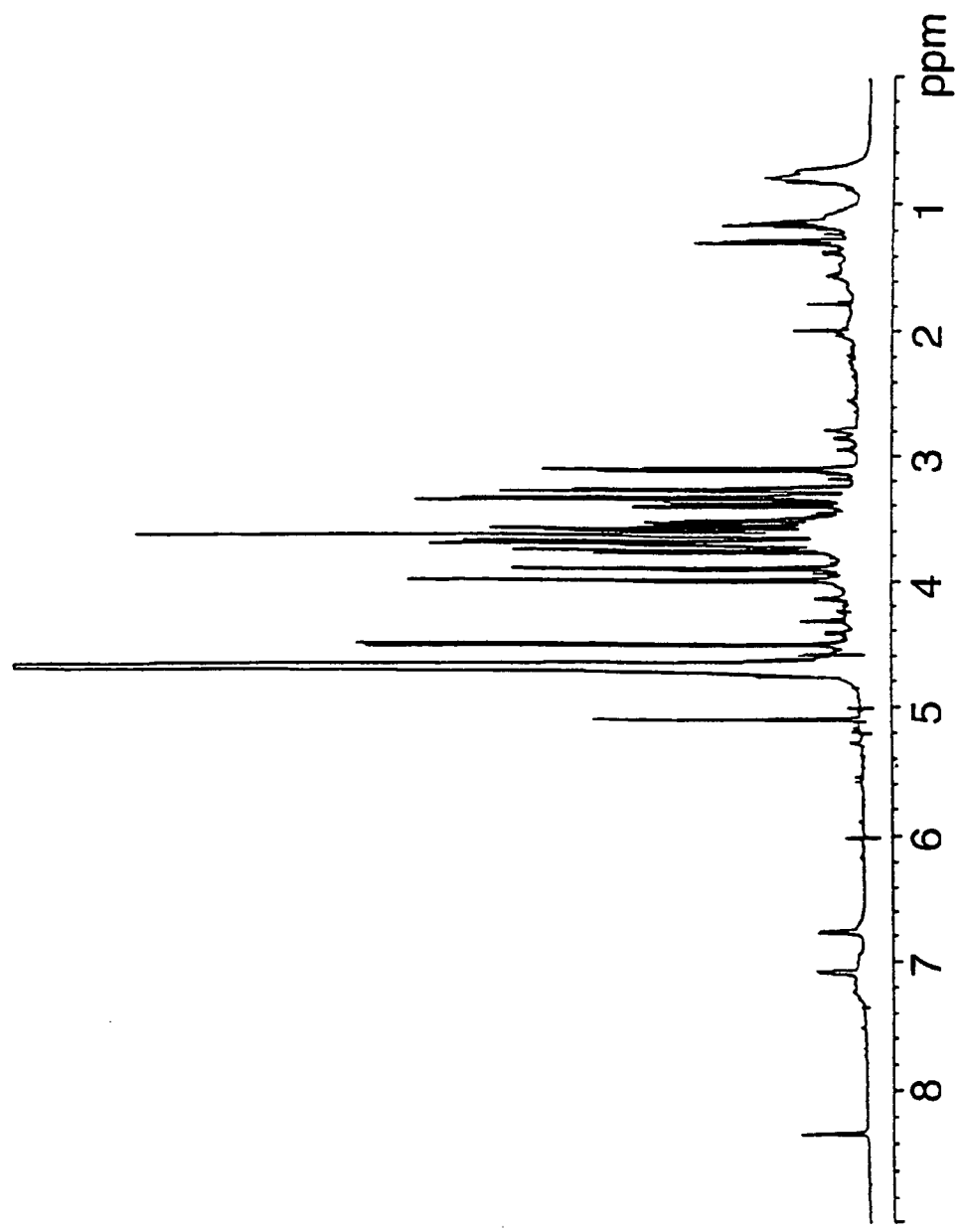
FIG. 5A is a copy of a graphical representation of a $^1H$ NMR spectrum of the active fraction purified by silica column and TLC as indicated in the legends to FIGS. 3A and 4. Numbering on the x-axis indicates ppm.

As shown in FIG. 5A, $^1$H NMR of the active fraction purified using silica gel and TLC as described in the preceding Example, produced peaks having resonances at 5.09, 3.57, 3.69, 3.39, 3.26, 3.69 and 3.63, which resonances correspond to protons attached to carbon atoms C1, C2, C3, C4, C5, and C6, suggesting that the active compound was a carbon-containing compound. Peaks characteristic of C2 to C6 of gluconic acid were also observed at 3.99, 3.89, 3.62, 3.62, 3.68 and 3.52.

Figure 5B:
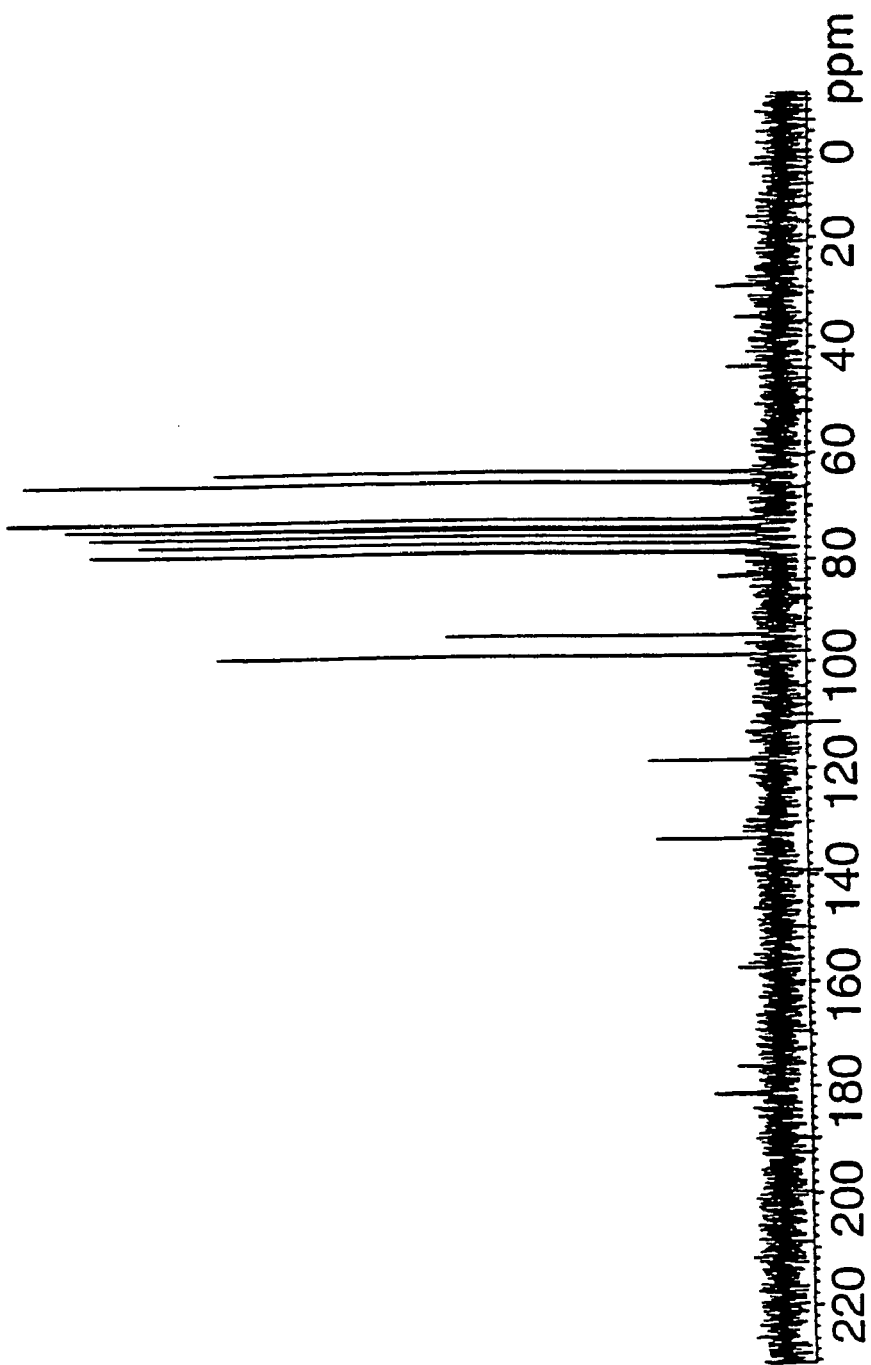
FIG. 5B is a copy of a graphical representation of a $^{13}C$ NMR spectrum of the active fraction purified by silica column and TLC as indicated in the legends to FIGS. 3A and 4. Numbering on the x-axis indicates ppm.

As shown in FIG. 5B, $^{13}$C NMR of the active fraction purified using silica gel and TLC as described in the preceding Example, produced peaks having resonances at 94.67, 75.35, 74.07, 74.02, 72.23 and 63.16, characteristic of carbons C1 to C6 of α-D-glucose; and peaks having resonances at 98.49, 78.53, 78.34, 76.71, 72.19, and 63.32, characteristic of C1 to C6 of β-D-glucose; and peaks having resonances at 181.2, 76.67, 73.54, 75.16, 73.76 and 65.2, which are characteristic of C1 to C6 of gluconic acid.

Figure 5C:
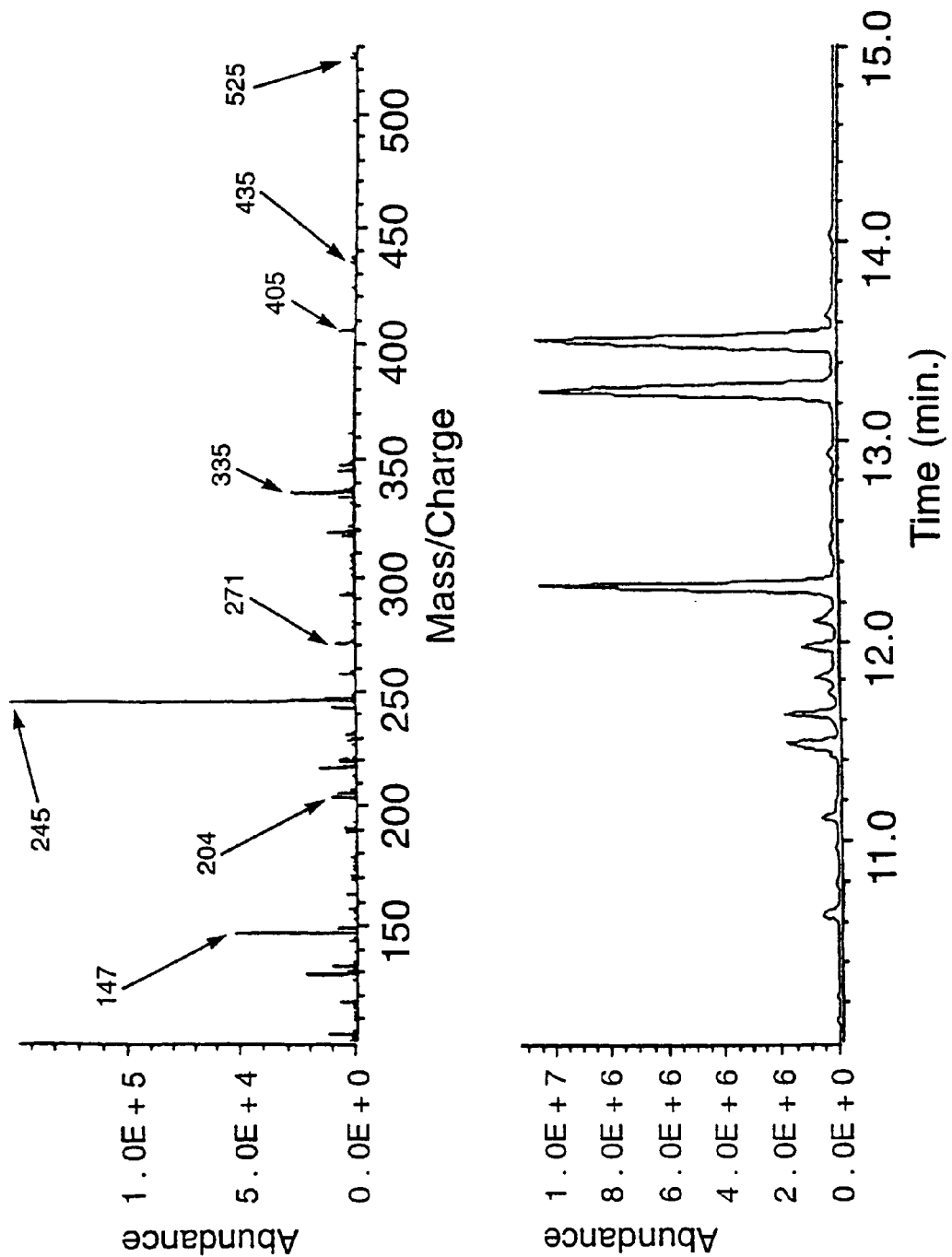
FIG. 5C is a copy of a graphical representation of mass spectrum data of the active fraction of *Pseudomonas* strain AN5 against take-all fungus which was purified by silica column as indicated in the legends to FIG. 3A and FIG. 4. *Pseudomonas* strain AN5 was cultured with glucose as the sole carbon source. Top panel: data show abundance of each fragment as a function of mass/charge. Lower panel: data show abundance of each fragment as a function of elution time (min). The arrow indicates the position of gluconolactone.

As shown in FIG. 5C, mass spectral analysis of the active fractions derived from silica gel and TLC as described in the preceding Example, also suggested that D-glucose and gluconic acid were present in the active fraction.

Figure 6A:
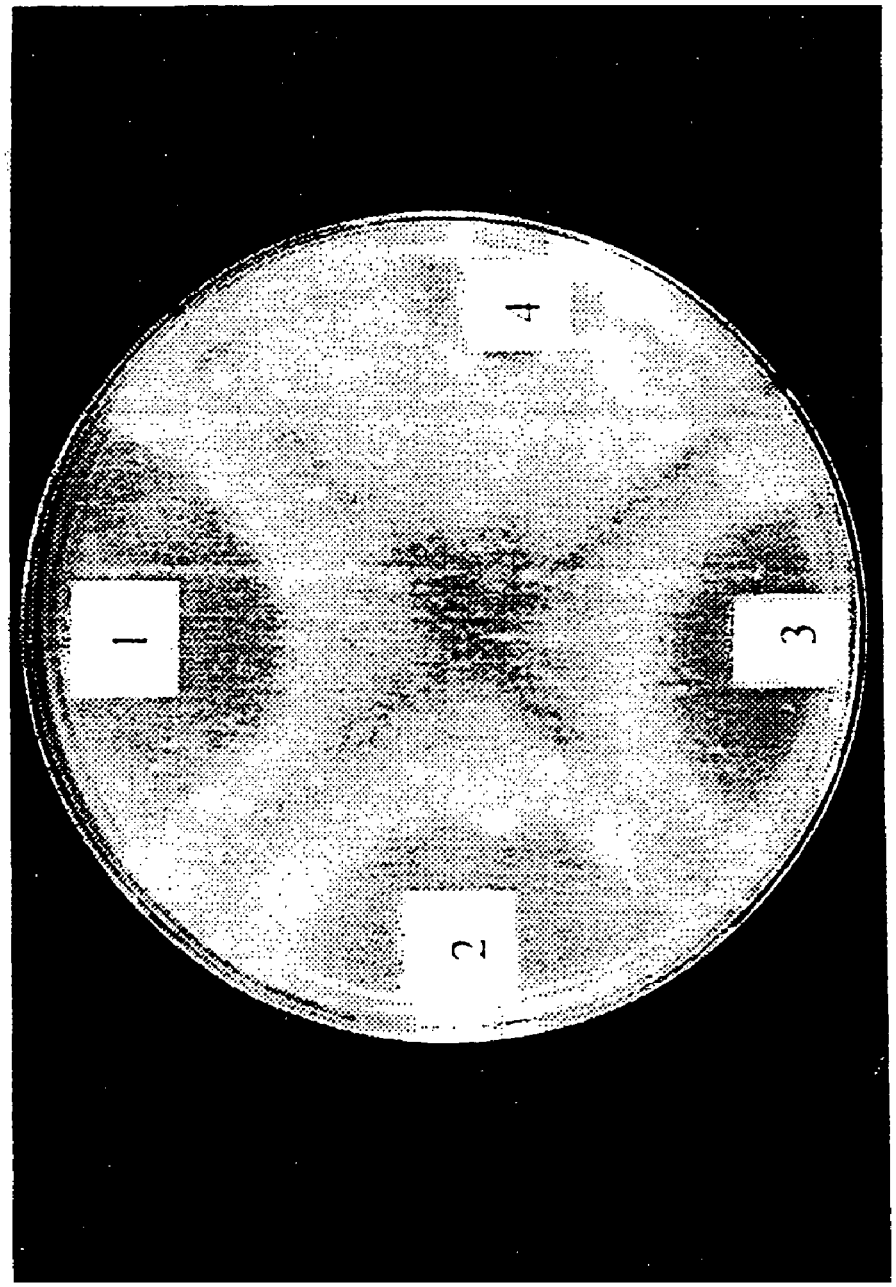
FIG. 6A is a copy of a photographic representation of a PDA plate inoculated with *Pseudomonas* strain AN5, showing the biological activity of different amounts of pure gluconic acid (Sigma Chemical Company Pty. Ltd.) against take-all using an agar overlay bioassay. Numbering indicates the amount of sugar acid used, as follows: (1) 25 mg; (2) 15 mg; (3) 12.5 mg; and (4) 7.5 mg. Data indicate that there is a positive correlation between the amount of gluconic acid used and the size of the inhibition zone (cleared region), which inhibition zone is indicative of activity against take-all fungus.
Figure 6B:
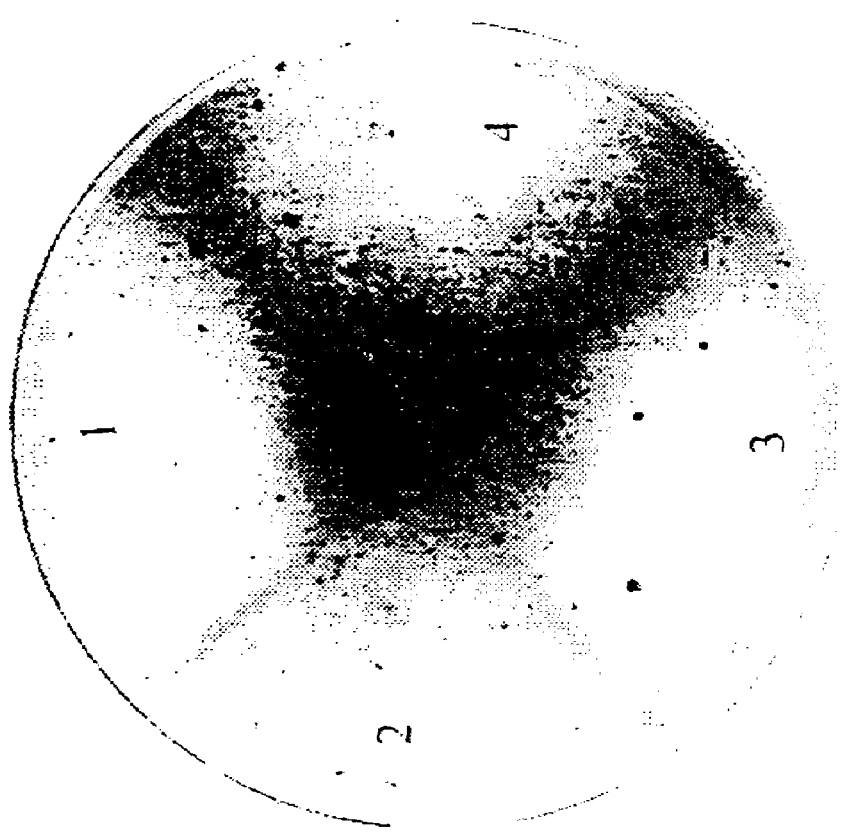
FIG. 6B is a copy of a photographic representation of a PDA plate inoculated with *Pseudomonas* strain AN5, showing the biological activities of different purified sugar acids (Sigma Chemical Company Pty. Ltd.) against the take-all fungus, using an agar overlay bioassay. The amount of sugar acid used was 12.5 mg in each case. Numbering indicates the sugar acid used, as follows: (1) malic acid; (2) ascorbic acid; (3) glutaric acid; and (4) glucuronic acid. All four sugar acids produce strong inhibition zones (cleared regions), indicative of activity against the take-all fungus.

Proceeding on the basis that the active compound was a sugar acid, pure gluconic acid and other sugar acids were tested for bioactivity against take-all using the PDA plate bioassay. As shown in FIG. 6A, purified gluconic acid possessed strong biologically activity against take-all. Data presented in FIG. 6B also indicated that purified malic acid, ascorbic acid, glutaric acid, and glucuronic acid possessed activity against take-all fungus at the concentrations tested.

Furthermore, the active compound produced by *Pseudomonas* strain AN5 is different to the anti-fungal compounds produced by other bacterial strains. The two bacterial strains, designated *Pseudomonas* strain AN5, and *Pseudomonas* strain Pf5, which have anti-fungal activity against take-all, were tested for the presence of 2,4-diacetylphloroglucinol according to the procedure of Keel et al. (1996). Extracts of these two bacterial strains were also analysed for the presence of amines, sugars, and carbonyl compounds, using art-recognised ninhydrin, silver nitrate, and dinitrophenylhydrazine tests, respectively. Some of the results indicating these differences are summarized below:

1. Solubility and Pigment Production

Figure 7:
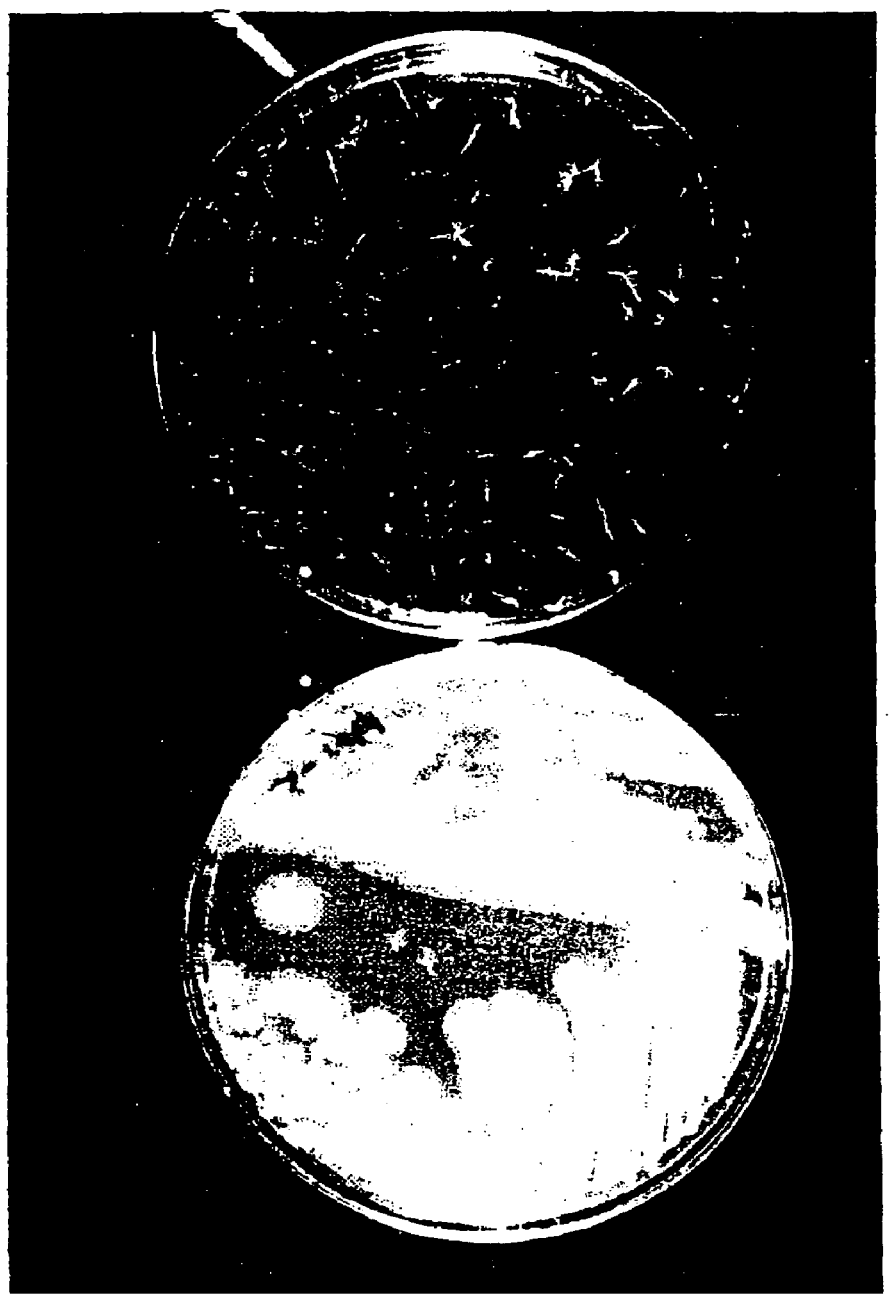
FIG. 7 is a black and white copy of a colour photographic representation of bacterial plates containing King's B media and inoculated with *Pseudomonas* strain AN5 (panel a), or *Pseudomonas fluorescens* Pf-5 (panel b). Data indicate that *Pseudomonas fluorescens* Pf-5 produces 2,4-diacetylphloroglucinol, by virtue of the darker appearance of this plate (which, in the original colour plate, is a red colour), compared to the whitened appearance of the plate in panel a. In contrast, *Pseudomonas* strain AN5 does not produce detectable levels of 2,4-diacetylphloroglucinol in this assay. The original colour photographic representation is available on request.

Phenazine-1-carboxylic acid (PCA) is a pigmented greenish-yellow antibiotic which accumulates in cultures of *P. fluorescens* strain 2-79 (Gurusiddaiah et al, 1986). PCA is highly soluble in chloroform and methylene chloride and insoluble in water, methanol and ethyl acetate. In contrast, the anti-fungal compound produced by *Pseudomonas* strain AN5 is highly-soluble in water. Moreover, *Pseudomonas* strain AN5 does produce coloured pigments while growing in media. Similarly, 2,4-diacetylphloroglucinol-producing strains of *Pseudomonas* sp. produce red pigments when grown on King's B medium (Keel et al, 1996). In contrast, no coloured substances were produced by *Pseudomonas* strain AN5 when grown on King's medium (FIG. 7).

2. Separation on TLC

The TLC profile of the active anti-fungal agent of *Pseudomonas* strain AN5 did not correspond to that observed for known anti-fungal agents. In particular, the sugar acids identified to have anti-fungal activity could not be separated on TLC using the solvents required to resolve previously-identified compounds. For example, on TLC plates of silica gel, using chloroform:methanol [19:1 (v/v)], 2,4-diacetylphloroglucinol has an Rf value of 0.2; and pyoluteorin has an Rf value of 0.5 (Keel et al, 1992). Additionally, using reverse-phase C18 TLC with an acetonitrile: methanol: water [1:1:1(v/v/v)] solvent system, 2,4-diacetylphloroglucinol has an Rf value of 0.88; pyoluteorin has an Rf value of 0.75; and pyronitrine has an Rf value of 0.28 (Rosales et al., 1995 and Pfender et al., 1993). In contrast, the sugar acid compound of the present invention did not migrate from the origin using a chloroform:methanol [19:1 (v/v)] solvent system (FIG. 1), and was only resolved poorly using acetonitrile: methanol: water [1:1:1 (v/v/v)].

3. Proton NMR Spectra

Figure 8:
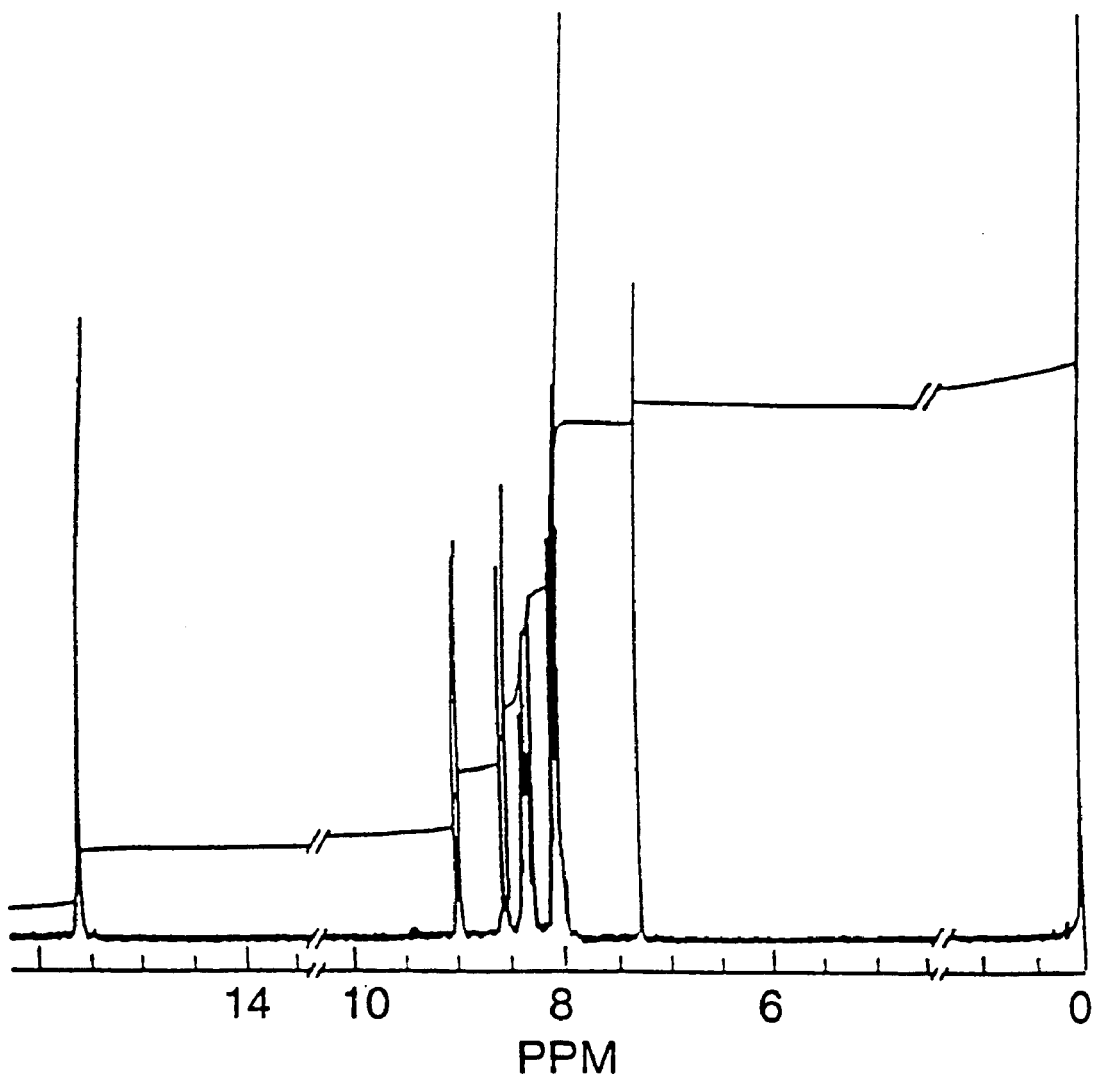
FIG. 8 is a copy of a graphical representation of the $^1H$ NMR spectrum of phenazine-1-carboxylic acid. Numbering on the x-axis indicates ppm.
Figure 9A:
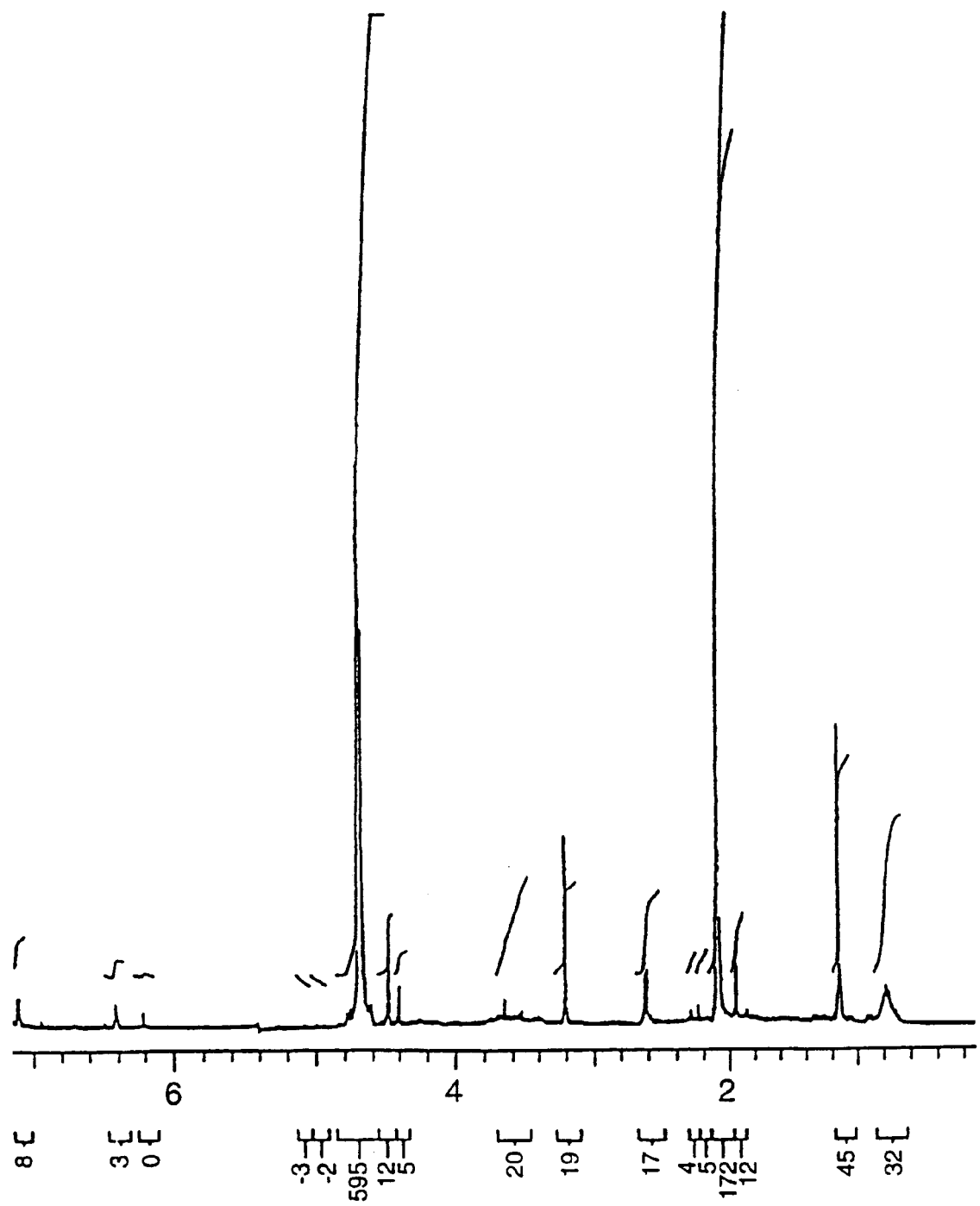
FIG. 9A is a copy of a graphical representation of $^1H$ NMR of a crude extract of *Pseudomonas fluorescens* Pf-5 from malt agar. Numbering on the x-axis indicates ppm.
Figure 9B:
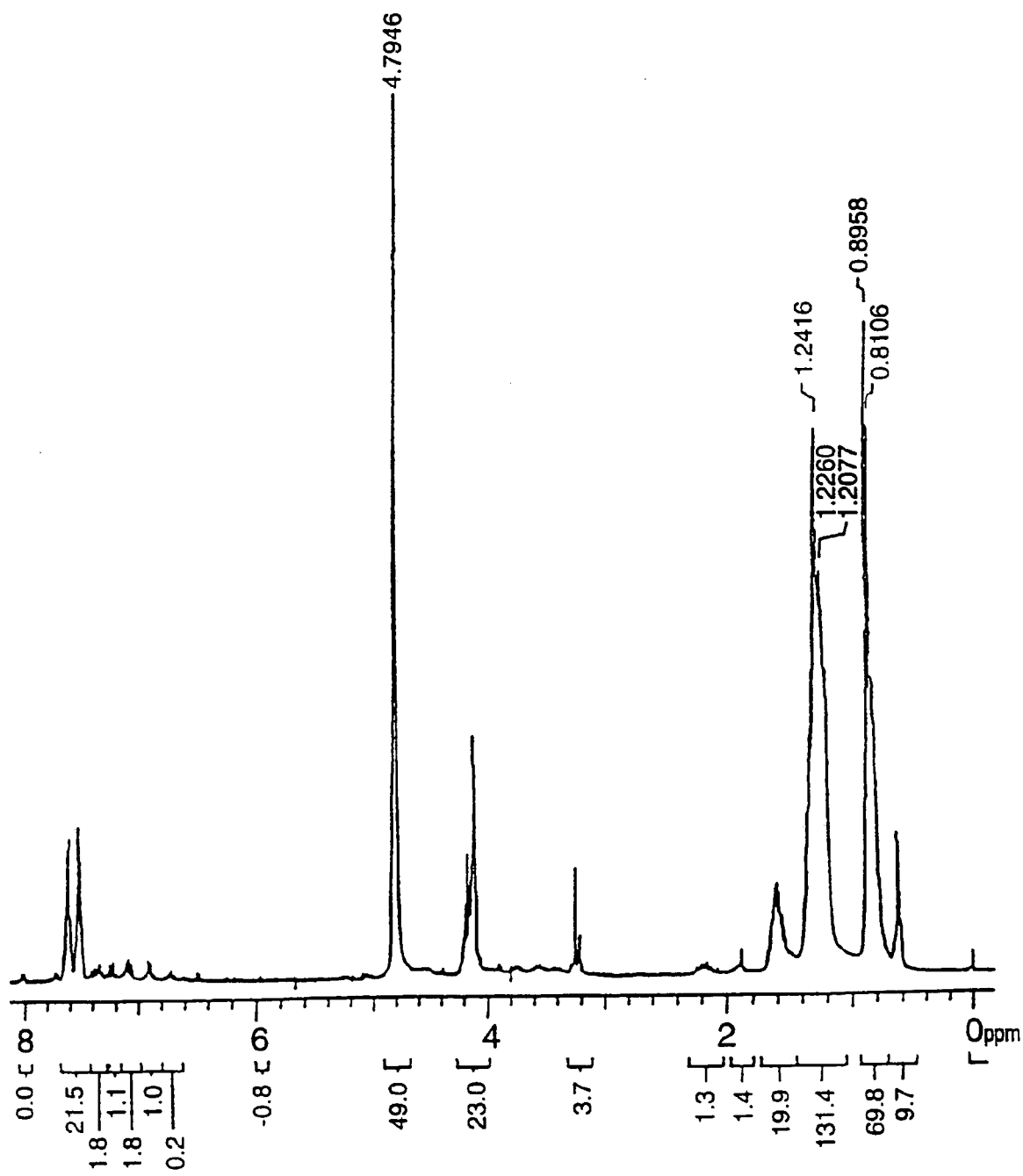
FIG. 9B is a copy of a graphical representation of $^1H$ NMR of a crude extract of *Pseudomonas* strain AN5 from malt agar. Numbering on the x-axis indicates ppm.

In 1H NMR of PCA, proton peaks are only observed above 7 ppm (Gurusiddaiah et al., 1986; FIG. 8), whereas no peaks were observed in this region in spectra of the new compound. In proton NMR of 2,4-diacetylphloroglucinol, two peaks at about 6.00 and 2.5 ppm are characteristic of the attachment of hydrogen to the six carbon protons and the six acetyl protons, respectively (Keel et al, 1992) and this did not match with proton NMR spectra obtained for crude extracts of *Pseudomonas* strain AN5, or *Pseudomonas* strain Pf5 (FIG. 9).

In summary, all of the chemical data obtained indicate that the anti-fungal compound of *Pseudomonas* strain AN5 is a carbohydrate, and, in particular, a sugar acid.

EXAMPLE 6

Sugar acids Produce by *Pseudomonas* sp. Induce a pH Change in Culture Media

Figure 10A:
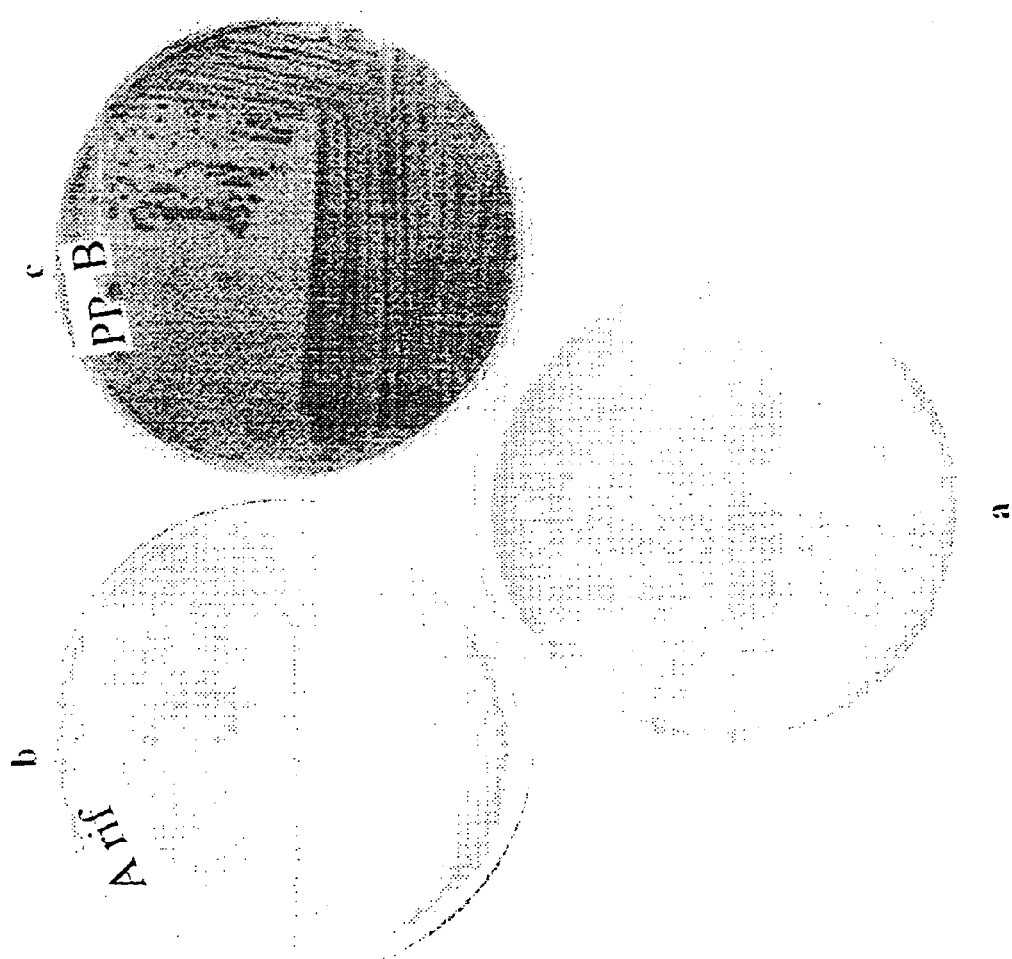
FIG. 10A is a black and white copy of a colour photographic representation of three PDA plates inoculated with *Pseudomonas* strain sp. strain AN5 (panels a and b) or the mutant strain AN5-MN1 (panel c). In panels b and c, the indicator dye bromocresol purple was added to the growth medium, and the yellow colour in panel b of the original photographic representation (darker grey colour over a light grey background in the black and white copy) is indicative of an acidification of the medium by *Pseudomonas* strain AN5. In panel c, the purple colour of the original photographic representation (very dark grey colour over a lighter grey background in the black and white copy) is indicative of an alkalisation of the medium by *Pseudomonas* strain AN5-MN1. The original colour photographic representation is available on request.
Figure 10B:
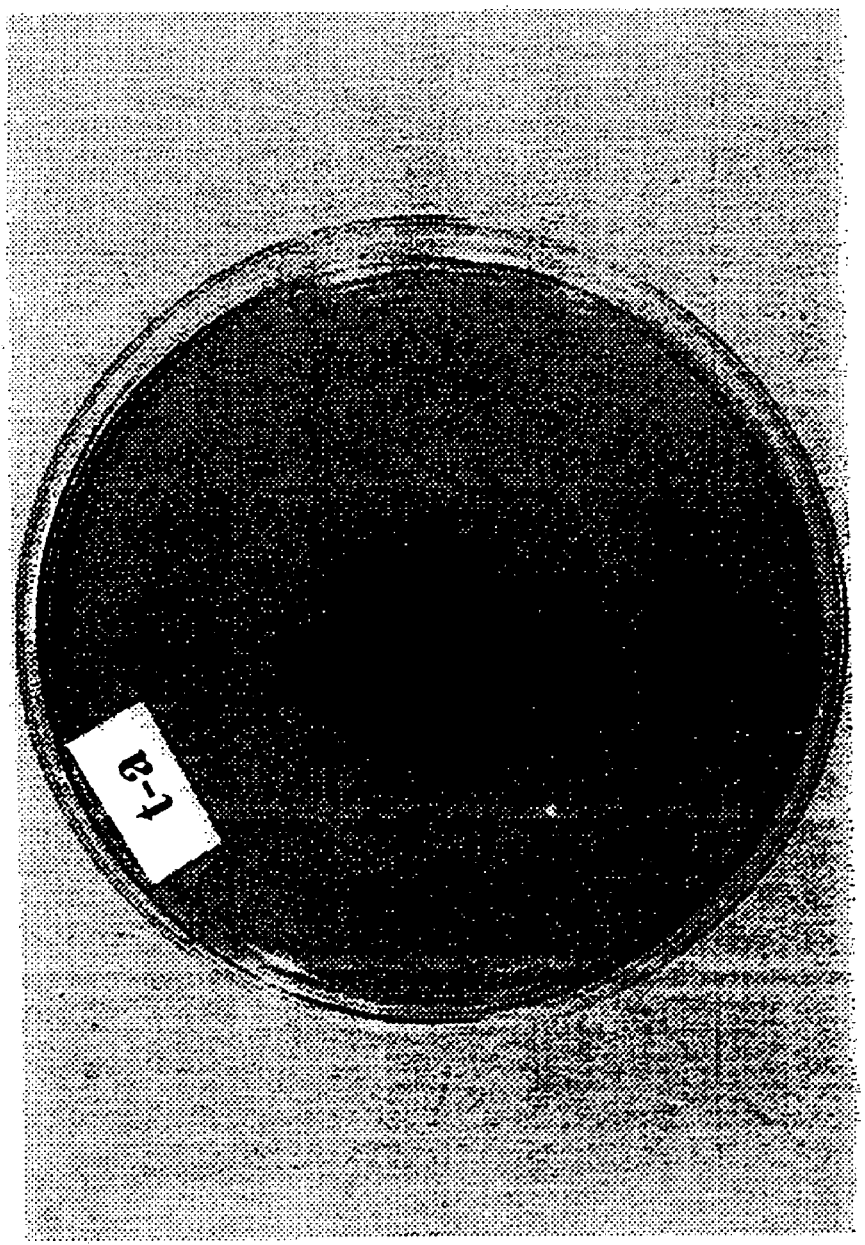
FIG. 10B is a black and white copy of a colour photographic representation of a PDA plate containing the indicator dye bromocresol purple and inoculated with the take-all fungus. In the original photograph, the take-all fungus is shown as a black central zone, surrounded by a yellow zone of growth, and there is a purple zone around the take-all fungus, suggesting it is releasing compounds which increase pH of the media. In the black and white copy, the take-all fungus is shown as a black central zone, surrounded by a light grey zone, and the purple zone around the take-all fungus is represented by a darker grey zone towards the edges of the plate. The original colour photographic representation is available on request.

The take-all fungus was grown on potato dextrose plates with the indicator dye, bromocresol purple (0.015 g/l). After 6–7 days of culture, a purple ring developed around take-all, indicating that the media was alkaline (FIG. 10B). Thus, the take-all fungal hyphae grow and releases compounds into the media which are alkaline in nature.

To determine whether this alkalating effect of take-all is modified by the sugar acid of the invention, the parental strain, *Pseudomonas* strain AN5, and the mutant strains, AN5-MN1, AN5-MN2, and AN5-MN3, were streaked onto PDA supplemented with bromocresol purple (0.015 g/l). Data presented in FIG. 10A indicate that *Pseudomonas* strain AN5 acidifies media supplemented with 2% (w/v) glucose when incubated therein, as detected by a yellow halo on PDA plates in the presence of with bromocresol purple. In contrast, the mutant strain AN5-MN1 was unable to produce this yellow halo after 34 days (FIG. 10A). The plates with the mutants on them went purple, which is an indicator of alkalinity. The absence of this colour change was noted for all mutants. These data indicate that, whereas *Pseudomonas* strain AN5 decreases the pH of the PDA growth medium, the mutants increase the pH of PDA. The correlation of these data with the anti-fungal activity of these bacterial strains further supports the conclusion that the anti-fungal compound produced by *Pseudomonas* strain AN5 is acidic in nature.

The effects of different concentrations of purified acids on the take-all root disease is shown in Table 2. Data presented in Table 2 suggest that acidification of the medium may play an important role in protecting against take-all. In particular, whilst gluconic acid confers protection against take-all, the sodium salt of gluconic acid did not confer significant protection against the fungal pathogen.

EXAMPLE 7

*Pseudomonas* Strain AN5 Produces Different Sugar Acids

*Pseudomonas* strain AN5 grown on nutrient agar, Kings B medium, or Malt agar, without aldose substrate, does not produce significant amounts of sugar acids, as indicated by the pH of the media. Extracts from these media have little or no biological activity against take-all fungus. Additionally, *Pseudomonas* strain AN5 on potato agar (which contains starch as its main carbon source) does not produce sugar acid, and the media is alkaline, and there is no anti-fungal biological control activity of extracts of *Pseudomonas* strain AN5 from potato agar.

In contrast, strong biological activity is detected when *Pseudomonas* strain AN5 is extracted from potato dextrose medium which contains glucose as a carbon source. Furthermore, the pH of this medium turns acidic in nature by virtue of the production of gluconic acid.

We have demonstrated that, if a different carbon source is added to potato agar inoculated with *Pseudomonas* strain AN5, such as galactose or mannose, then sugar acids are produced. The media extracted from such cultures have biological activity against take-all fungus.

Figure 11A:
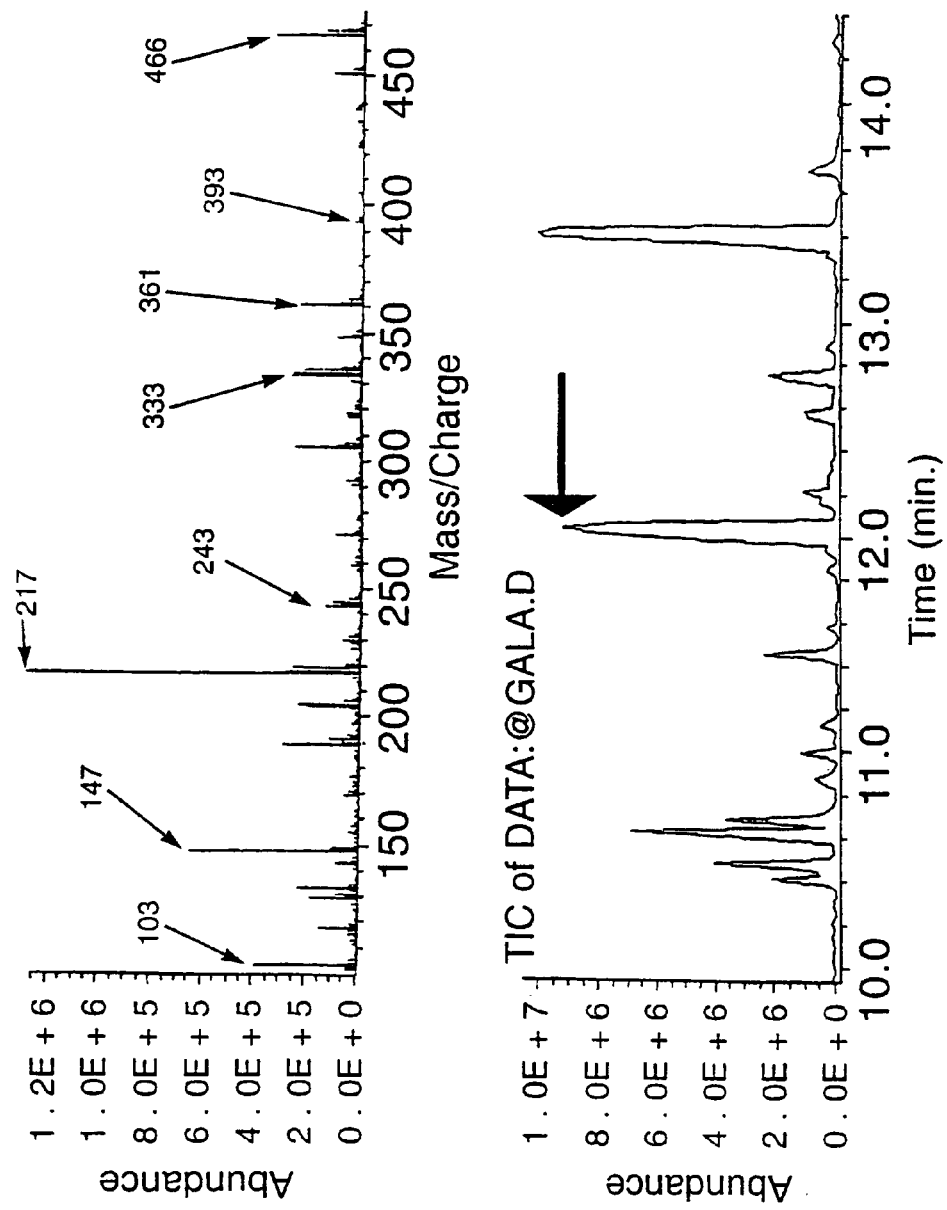
FIG. 11A is a copy of a graphical representation of mass spectrum data of the active fraction of *Pseudomonas* strain AN5 against take-all fungus which was purified by silica column as indicated in the legend to FIG. 3A. *Pseudomonas* strain AN5 was cultured with galactose as the sole carbon source. Top panel: data show abundance of each fragment as a function of mass/charge. Lower panel: data show abundance of each fragment as a function of elution time (min). The arrow indicates the position of galactonolactone.
Figure 11B:
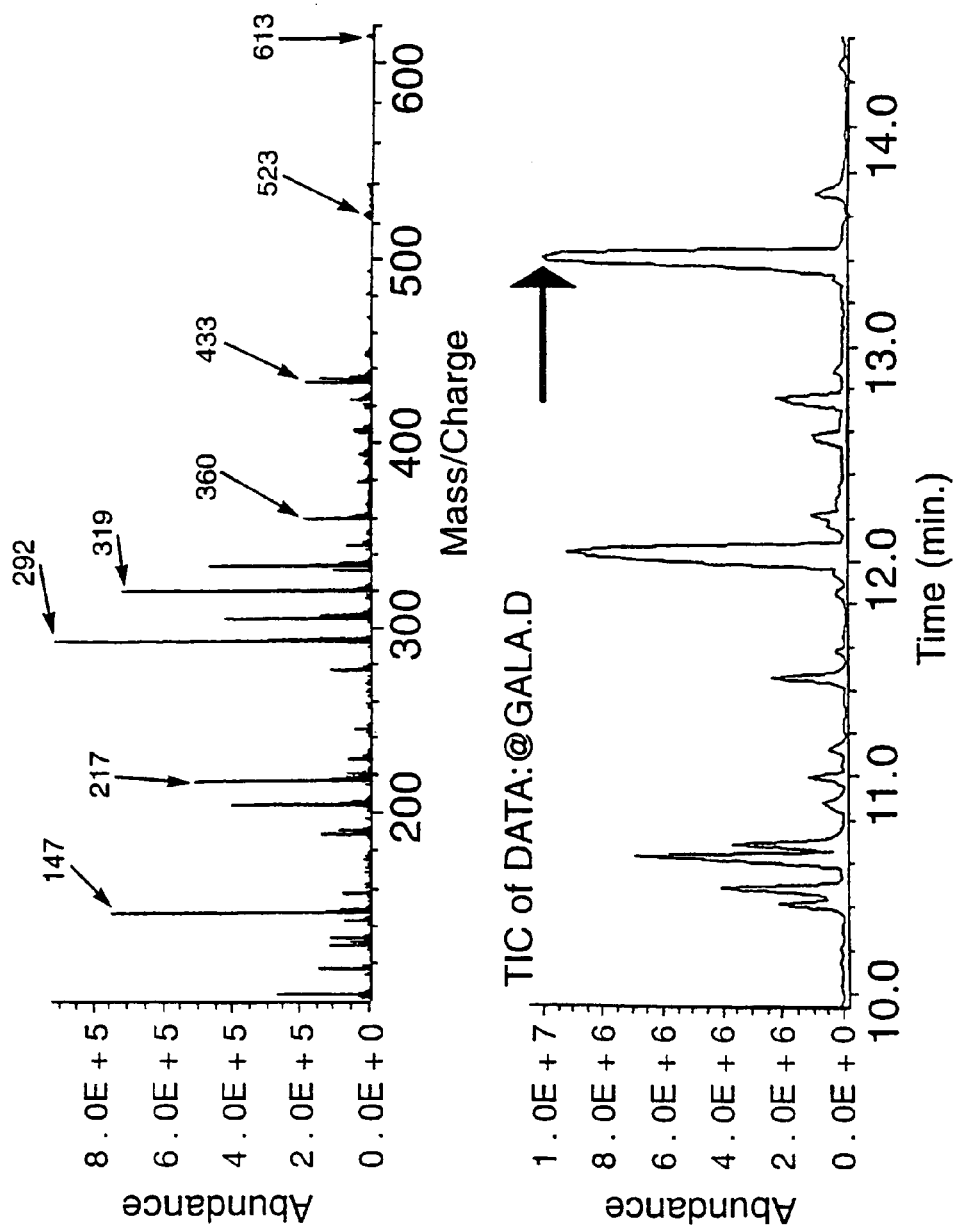
FIG. 11B is a copy of a graphical representation of mass spectrum data of the active fraction of *Pseudomonas* strain AN5 against take-all fungus which was purified by silica column as indicated in the legend to FIG. 3A. *Pseudomonas* strain AN5 was cultured with galactose as the sole carbon source. Top panel: data show abundance of each fragment as a function of mass/charge. Lower panel: data show abundance of each fragment as a function of elution time (min). The arrow indicates the position of galactonic acid.

Data presented in FIGS. 11A and 11B indicate that galacturonic acid is produced from cultures of *Pseudomonas* strain AN5 grown on PD medium supplemented with galactose.

Figure 12A:
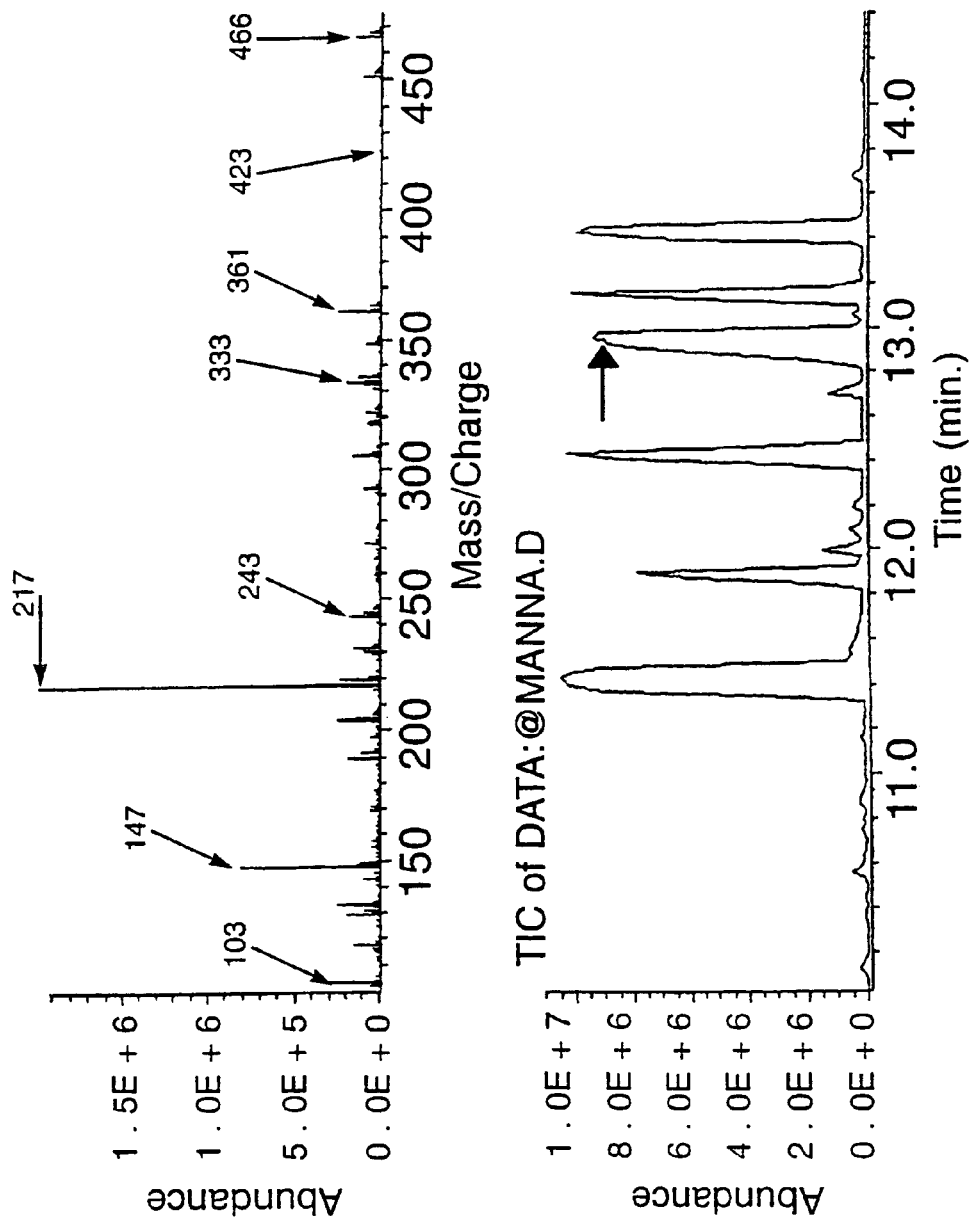
FIG. 12A is a copy of a graphical representation of mass spectrum data of the active fraction of *Pseudomonas* strain AN5 against take-all fungus which was purified by silica column as indicated in the legend to FIG. 3A. *Pseudomonas* strain AN5 was cultured with mannose as the sole carbon source. Top panel: data show abundance of each fragment as a function of mass/charge. Lower panel: data show abundance of each fragment as a function of elution time (min). The arrow indicates the position of mannono-1,4-lactone.
Figure 12B:
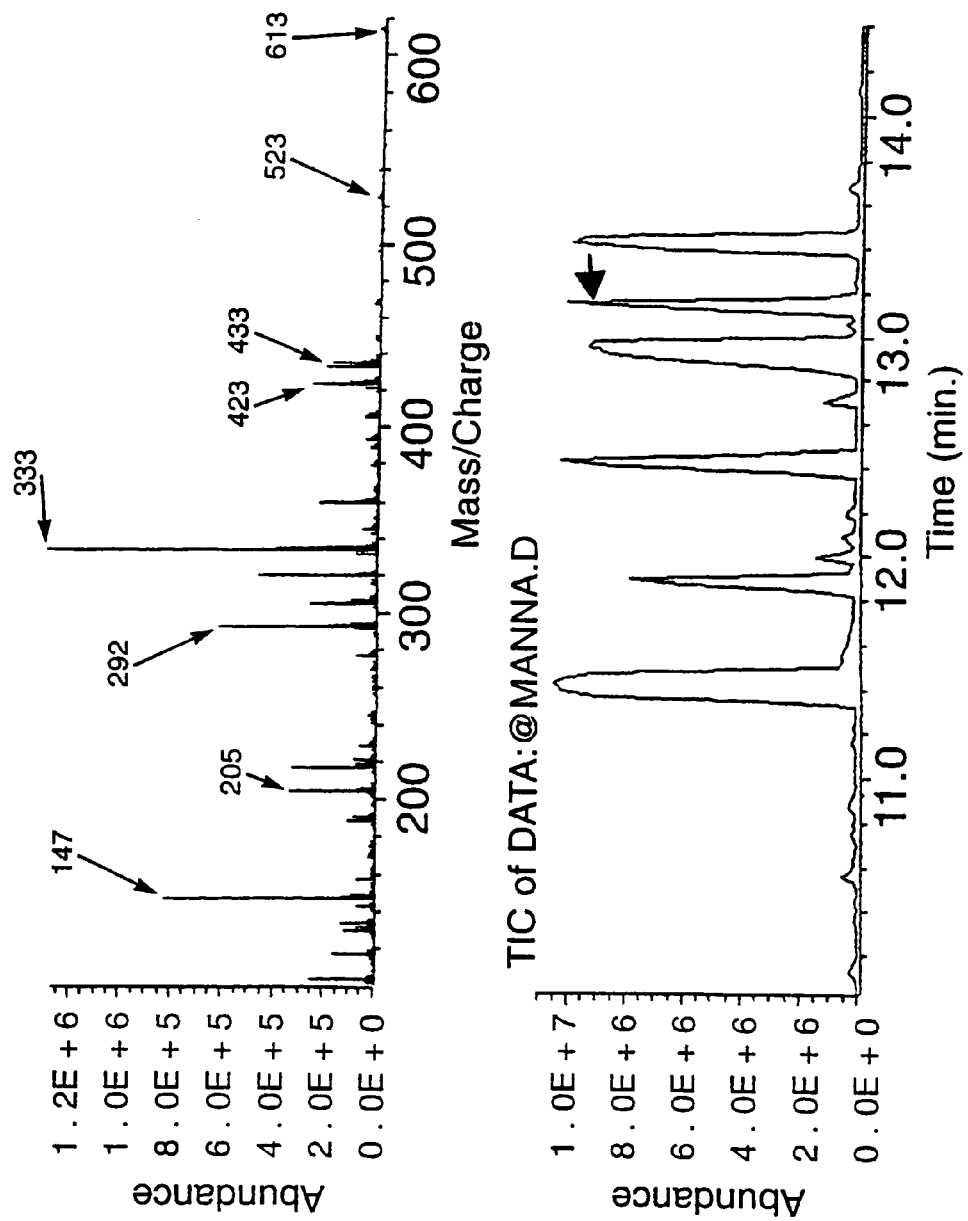
FIG. 12B is a copy of a graphical representation of mass spectrum data of the active fraction of *Pseudomonas* strain AN5 against take-all fungus which was purified by silica column as indicated in the legend to FIG. 3A. *Pseudomonas* strain AN5 was cultured with mannose as the sole carbon source. Top panel: data show abundance of each fragment as a function of mass/charge. Lower panel: data show abundance of each fragment as a function of elution time (min). The arrow indicates the position of mannonic acid.

Additionally, data presented in FIGS. 12A and 12B indicate that mannonic acid is produced from cultures of *Pseudomonas* strain AN5 grown on PD medium supplemented with mannose.

However, the biological activities against take-all of mannonic acid or galacturonic acid are not as strong as gluconic acid. From what is known about the efficiency of conversion of different aldose substrates by *Aspergillus* sp., it is possible that glucose is merely converted more efficiently into sugar acids than mannose or galactose.

EXAMPLE 8

Broad Anti-fungal Activity of Gluconic Acid Produced by *Pseudomonas* Strain AN5

*Pseudomonas* strain AN5 was tested against a range of microorganisms for biological control as listed in Table 3, using the PDA plate bioassay, to determine the efficacy of gluconic acid in controlling growth of these pathogens. The anti-fungal agent produced by *Pseudomonas* strain AN5 showed activity against a broad spectrum of fungi which represent plant pathogens, human pathogens and saprophytes. When tested against bacterial species there were some Gram negative and Gram positive species which were inhibited by the agent produced by *Pseudomonas* strain AN5, however the species-spectrum of protection was not as broad as in the case of fungi. The range of inhibition observed was in the range of total protection to only partial protection.

TABLE 2

| Sugar acid | Amount (mg) | media pH | Clearance zone radii (cm) | pKa |
|---|---|---|---|---|
| Malic acid | 7.5 | | 1.0 | 3.4 |
| | 12.5 | | 2.0 | |
| | 25.0 | 1.5 | 2.5 | |
| Ascorbic acid | 7.5 | | 0.0 | 4.17 |
| | 12.5 | | 0.9 | |
| | 25.0 | 1.9 | 2.0 | |
| Glutaric acid | 7.5 | | 1.5 | 4.31 |
| | 12.5 | | 2.0 | |
| | 25.0 | 2.0 | 2.5 | |
| Glucuronic acid | 7.5 | | 0.0 | |
| | 12.5 | | 1.0 | |
| | 25.0 | 1.7 | 2.0 | |
| Gluconic acid | 7.5 | | 0.7 | 3.6 |
| | 12.5 | | 1.0 | |
| | 25.0 | about 5.0 | 2.0 | |
| Sodium gluconate | 7.5 | | 0.0 | |
| | 12.5 | | 0.0 | |
| | 25.0 | about 7.0 | 0.0 | |
| Galacturonic acid | 7.5 | | 0.7 | 4.76 |
| | 12.5 | | 2.0 | |
| | 25.0 | 1.7 | 2.5 | |
| Acetic acid | 1.05 | | 1.5 | |
| | 2.1 | | 3.0 | |
| | 4.2 to 8.4 | 2.4 | >3.0 | |

EXAMPLE 9

Mutant Strains of *Pseudomonas* sp. Which Have Modified Activity Against *G. graminis* var. *tritici* (Take-all)

The inventors have isolated naturally-occurring mutants of *Pseudomonas* AN5 bacteria, and genetically engineered new strains of *Pseudomonas* AN5 bacteria, which produce different amounts of sugar acids when grown on aldose substrates. This has been achieved, for example, by culturing the parent strain on different antibiotics, by introducing a multi-copy plasmid with additional anti-fungal genes into *Pseudomonas* strain AN5, or by transposon mutagenesis of *Pseudomonas* strain AN5. Strains which produce less EPS, to facilitate the secretion of more sugar acid into the surrounding medium have also been produced. These mutants and derivatives of *Pseudomonas* strain AN5 produce larger clearance zones in agar plate bioassays. These strains have been tested for biological control protection against take-all in controlled environment cabinet trials.

Mutants Having Reduced Anti-fungal Activity

Mutants having reduced anti-fungal activity are particularly useful as negative controls in experiments to identify anti-fungal compounds, or as vectors into which different anti-fungal properties, such as genes encoding sugar oxidases, may be introduced.

One particularly useful mutant, designated *Pseudomonas* strain AN5-M1, is a single transposon mutant strain of AN5 which has lost anti-fungal activity. A Tn5 transposon has been inserted into a gene which is required for activity against take-all in this mutant.

Three transposon mutants, AN5-MN1, AN5-MN2, and AN5-MN3 were isolated which have lost biocontrol activity, do not produce the anti-fungal metabolite and are unable to control the take-all root disease of wheat. These mutants cannot utilise glucose in a similar pathway to the parent strain, *Pseudomonas* strain AN5. These mutants are deficient in an enzyme which converts glucose to sugar acid.

TABLE 3

Host range of protection conferred by *Pseudomonas* strain AN5 cultured in the presence of glucose substrate

| TYPE OF ORGANISM | SPECIES TESTED | MODE OF INFECTION |
| --- | --- | --- |
| Deuteromycetes | E. pupurescens | Saprophytic |
| | Alternaria sp. | Saprophytic |
| | A. oligosporus | Saprophytic |
| | M. fructocola | Pathogenic |
| | B. cinerea | Pathogenic |
| | V. dahliae | Pathogenic/Saprophytic |
| Basidiomycetes | F. annosus | Pathogenic |
| | A. mellea | Pathogenic |
| | B. granulatus | Mycorrhizal |
| | P. suphureus | Saprophytic |
| Yeast | S. cerevisiae | Saprophytic |
| Gram negative bacterium | number of species | Varied |
| Gram positive bacterium | number of species | Varied |

Mutants Having Reduced Anti-fungal Activity

Mutants having reduced anti-fungal activity are particularly useful as negative controls in experiments to identify anti-fungal compounds, or as vectors into which different anti-fungal properties, such as genes encoding sugar oxidases, may be introduced.

One particularly useful mutant, designated *Pseudomonas* strain AN5-M1, is a single transposon mutant strain of AN5 which has lost anti-fungal activity. A Tn5 transposon has been inserted into a gene which is required for activity against take-all in this mutant.

Three transposon mutants, AN5-MN1, AN5-MN2, and AN5-MN3 were isolated which have lost biocontrol activity, do not produce the anti-fungal metabolite and are unable to control the take-all root disease of wheat. These mutants cannot utilise glucose in a similar pathway to the parent strain, *Pseudomonas* strain AN5. These mutants are deficient in an enzyme which converts glucose to sugar acid.

Two additional transposon mutants, carrying the Tn5:uidA transposon, were identified by virtue of their inability to confer biocontrol against take-all fungus. These mutants were designated PQQ and SOX. As shown in Example 13, the PQQ and SOX mutants contained the Tn5 element in the pqqD gene, and sugar oxidase gene, respectively, of the *Pseudomonas* sp. genome.

Mutants Having Increased Anti-fungal Activity

A spectinomycin-resistant strain, designated *Pseudomonas* strain AN5 spec, was isolated as a naturally-occurring mutant of *Pseudomonas* strain AN5, by screening for growth on the antibiotic spectinomycin. *Pseudomonas* strain AN5spec has adequate biocontrol characteristics against take-all fungus.

*Pseudomonas* strain AN5 rif (AGAL Accession No. NM 00/09624) was isolated as a naturally-occurring mutant of *Pseudomonas* strain AN5, by screening for growth on the antibiotic rifampicin. Accordingly, *Pseudomonas* strain AN5rif is rifampicin-resistant. Bioassays using this strain indicate that is has superior biocontrol characteristics against take-all fungus, on both PDA plates and in pot trials, compared to the parent strain of *Pseudomonas* strain AN5spec.

*Pseudomonas* strain AN5-M1 was modified by introducing a cosmid comprising the pLAF3 vector with a wild-type region of *Pseudomonas* strain AN5 genome inserted therein. Cosmid pLAF3 is generally multi-copy in *Pseudomonas* sp., however copy number is relatively low (10–15 copies per chromosome), compared to many bacterial plasmids. Transformants were screened for anti-fungal activity against take-all.

One transformant was identified which protected against take-all as efficiently as the parent strain, *Pseudomonas* strain AN5. However, this modified bacterial strain only poorly colonises the roots of wheat and there are very few numbers of bacteria present on the roots compared to the colonising ability of the parent strain, suggesting that, for the transformant, each individual cell which colonises the roots may provide superior protection compared to an individual cell of the parent strain, presumably by producing greater levels of anti-fungal agent on a cell basis. These data also suggest that, by increasing the capacity of a single cell to produce the anti-fungal compound, a more effective biological control strain may be created.

The inventors have also created a range of genetically-engineered strains which colonize the roots of wheat in a normal manner and show a greater clearance zone in agar plate bioassays.

The inventors have also genetically-engineered a number of novel biocontrol strains that produce higher amounts of anti-fungal agent, either by introducing multi-copy plasmids (eg. *Pseudomonas* strain AN5-M1, and *Pseudomonas* strain AN5-P1) or by obtaining a transposon mutant of this strain (eg. *Pseudomonas* strain AN5-T5).

These enhanced biological control strains were shown to be more potent against take-all in agar plate bioassays by their larger clearance zones. Results with strains *Pseudomonas* strain AN5-P1 and *Pseudomonas* strain AN5-T5 indicated that an increase in biological control protection can be obtained against take-all fungus by increasing the anti-fungal nature of the strain without compromising colonisation ability. Therefore, an increased in anti-fungal activity increases biological control protection ability.

In glasshouse trials, these modified strains were shown to protect significantly better than the parent strain, *Pseudomonas* strain AN5, as determined by the scoring of symptoms on the roots of wheat. In particular, inhibition of growth of *G. graminis* in the presence of these strains was determined following inoculation of pots with the fungus on millet seed. Control samples contained either no added fungus or biocontrol bacterium, or fungus without biocontrol bacteria. Disease score for take-all was determined, using a scale wherein a numeric indicator is assigned to the severity of the disease, as follows: zero=no disease; 1=disease which is barely detectable; and 5=maximum disease on the crown of the plant. At the end of the experiment, the plants were also dried and weighed, and their dry weights expressed as a percentage of the dry weight of control plants. Data presented in Table 4 indicate the mean data obtained over six treatments. Enhanced antibiosis is indicated by the enhanced anti-fungal activities of the genetically-engineered strains, compared to the parental strain.

In such pot trials, where an excess of take-all fungus was artificially added to the potting medium, these improved biocontrol strains provided significant protection against take-all for much longer periods of time than the parent strain. *Pseudomonas* strain AN5-P1, and *Pseudomonas* strain AN5-T5, which produce higher concentrations of sugar acids, have the potential to provide greater protection when they are lower in number on wheat roots. Therefore, these strains should give better protection against take-all when reduced in number on the roots of wheat during drier winter growing seasons.

EXAMPLE 10

Mass Spectrum Analysis of Sugar Acids Produced by *Pseudomonas* Strain AN5 rif

*Pseudomonas* strain AN5 rif (AGAL Accession No. NM 00/09624), was cultured for two days at 25° C. in 100 ml of sterile (autoclaved) pontiac broth (potatoes 400 g/l), comprising either 2% (w/v) glucose, or 4% (w/v) glucose, or 4% (w/v) galactose, or 4% (w/v) mannose as a carbon source. The identities of the sugar acids produced were determined using mass spectrum as described in the preceding Examples.

Figure 5D:
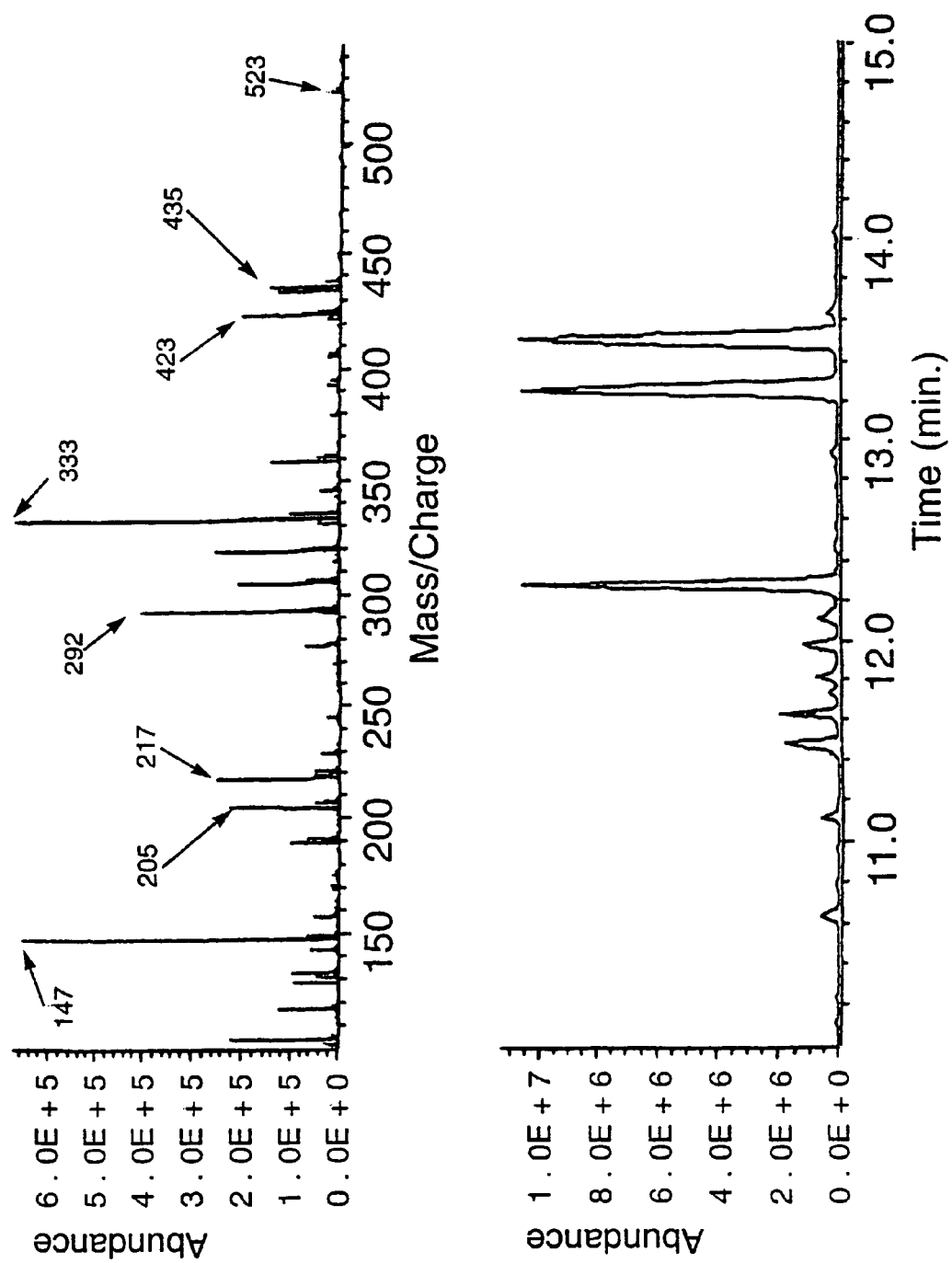
FIG. 5D is a copy of a graphical representation of mass spectrum data of the active fraction of *Pseudomonas* strain AN5 against take-all fungus which was purified by silica column as indicated in the legend to FIG. 4. *Pseudomonas* strain AN5 was cultured with glucose as the sole carbon source. Top panel: data show abundance of each fragment as a function of mass/charge. Lower panel: data show abundance of each fragment as a function of elution time (min). The arrow indicates the position of gluconic acid.

Mass spectrum analysis of active fractions indicated that, in each sample, there is only one sugar acid produced which corresponds to the aldonic acid product of the aldose sugar substrate provided to the bacterial cultures grown under these conditions. In particular, glucose was converted to gluconic acid (i.e. the peak for gluconic acid was as in FIG. 5D), galactose was converted to galactonic acid (the peak for galactonic acid was as in FIG. 11B), and mannose was converted to mannonic acid (the peak for mannonic acid was as in FIG. 12B).

TABLE 4

Comparison of genetically engineered strains

| Bacterial Treatment | Bacteria (cells/gram wheat root) | Take-all disease score | Plant dry weight (% of control plant) |
|---|---|---|---|
| 1. Control (no take-all or bacteria) | 0 | 0 | 100% |
| 2. Take-all treatment (no bacteria) | 0 | 5 | 9% |
| 3. *Pseudomonas* strain AN5 | $8 \times 10^7$ | 2 | 78% |
| 4. *Pseudomonas* strain AN5-MI | $1 \times 10^3$ | 2 | 83% |
| 5. *Pseudomonas* strain AN5-PI | $8 \times 10^5$ | 1 | 93% |
| 6. *Pseudomonas* strain AN5-T5 | $5 \times 10^7$ | 1 | 95% |

EXAMPLE 11

Quantitation of Gluconic Acid Produced by *Pseudomonas* Strain AN5 rif Cultures Using Glucose as the Sole Carbon Source 1. Quantitation of Sugar Acids Produced by *Pseudomonas* sp. Strain AN5 rif

*Pseudomonas* strain AN5 rif (AGAL Accession No. NM 00/09624), was cultured for two days at 25° C. in 100 ml of sterile (autoclaved) pontiac broth (potatoes 400 g/l), comprising either 2% (w/v) glucose, or 4% (w/v) glucose, or 2% (w/v) galactose, or 4% (w/v) galactose. A negative control solution was also prepared which contained no additional aldose substrate. Sugars were added from stock solutions sterilised by the addition of chloroform.

The total numbers of viable cells were determined after two days of culture, using standard procedures. The viable count for cultures containing 2% (w/v) glucose in pontiac broth were, on average $7.325 \times 10^7$ cells/ml, compared to only $6.0 \times 10^4$ cell/ml for cultures grown on pontiac broth without added sugar.

The pH values of the culture supernatants were determined following collection of the bacterial cells after two days of culture, by centrifugation at 6,000 rpm to collect bacterial cells, and titration of an aliquot of each supernatant against 0.001N to 0.01N NaOH. To confirm the titrable pH value obtained for each supernatant, equal volumes of acetone were added to the remaining supernatants, and samples incubated overnight at 4° C. to precipitate any proteinaceous components or bacterial cells. The precipitates were removed by centrifugation at 6,000 rpm and the pH values of the culture supernatants determined by titration as before. Results were as follows:

| | |
|---|---|
| Bacteria cultured with 2% (w/v) glucose: | pH = 8.0 (8.8**); |
| Bacteria cultured with 4% (w/v) glucose: | pH = 7.9 (8.5**); |
| Bacteria cultured with 2% (w/v) galactose: | pH = 8.2 (8.8**); |
| Bacteria cultured with 4% (w/v) galactose: | pH = 7.9 (8.3**); |
| Bacteria cultured without sugar | pH = 9.0 (9.6**); and |
| Pontiac broth alone: | pH = 6.5. |

**pH values in parentheses indicate the pH of supernatants following acetone precipitation.

Pontiac broth comprising 2% (w/v) galactose produced a magenta (dark pink) colour using the indicator dye phenolphthalein, and, as a consequence, that medium was not titratable using sodium hydroxide solution. Other media required small volumes of 0.001N sodium hydroxide to produce the same pink colour as that which was produced for pontiac broth inoculated with *Pseudomonas* strain AN5 rif (AGAL Accession No. NM 00/09624) in the absence of aldose. The average amount of 0.001N NaOH required to neutralize acid sugars produced by each 100 ml culture (n 3), was as follows:

| | |
|---|---|
| Bacteria cultured with 2% (w/v) glucose: | 0.6 ml; |
| Bacteria cultured with 4% (w/v) glucose: | 0.8 ml; |
| Bacteria cultured with 2% (w/v) galactose: | nd**; |
| Bacteria cultured with 4% (w/v) mannose: | 0.45 ml; and |
| Bacteria cultured without sugar: | 0.0 ml. |

**not determined

For solid media, pontiac agar plates were prepared and adjusted to pH values of 6.5, 8.5, 10.5, and 12.5. Bromocresol purple (15 mg/l) was added to each plate. Pontiac agar plates were inoculated by streaking *Pseudomonas* strain AN5 rif (AGAL Accession No. NM 00/09624), and incubated for one day at 25° C. After this period, those plates which were at a pH in the range of pH 6.5 to pH 10.5 began to turn yellow. However, no colour change was apparent for those plates at pH 12.5. Bacterial growth was also affected by the pH of the culture media, and more growth was observed at lower pH values, in the order: 6.5=8.5>10.5>12.5. Growth was very poor at pH 12.5.

In summary, titration of bacterial cultures is not the optimum method for the quantitation of sugar acids, wherein the carbon source is other than glucose, because of the high alkaline pH of the solution which is required for bacterial growth. However, this method is preferred for use in conjunction with solid media. Alternatively, sugars are quantitated using the procedure described in the following citation: Microbiology 143:1595–1603, 1997.

2. Assay of Gluconic Acid Production by *Pseudomonas* Strain AN5 rif

*Pseudomonas* strain AN5 rif (AGAL Accession No. NM 00/09624) was streaked onto nutrient agar containing rifampicin (100 ug/ml) and incubated at 25° C. for two days. From these plates, nutrient broth and pontiac broth were inoculated with a bacterial loop. These broths were also incubated at 25° C. on a shaker for two days. 5 ml of these broths was used to inoculate 100 ml of respective broths. These were grown overnight for about 15–18 hour. Small aliquot's of these were used with a number of dilutions to obtain viable cell counts. These cultures were centrifuged at 600 rpm for 15 minutes to pellet cells. The bacterial pellets were washed twice with distilled autoclaved water to remove any broth, and resuspended in 100 ml 0.01M glucose solution (pH 7 glucose at 1.8 g/l). Bacterial suspensions were incubated on shaker at 25° C. After 3.5 h, these solutions were observed to produce a yellow colour in the presence of bromocresol purple (15 mg/l). Supernatant's were frozen at −30° C. and then lyophilised. An aliquot of the lyophilised material was dissolved in water, and 5 ml of solution was titrated with 0.01N NaOH. Sugar acids were quantitated as described above.

Data indicate that bacteria obtained from pontiac broth as a starter culture and then grown in pure glucose solution are capable of converting 40% of the glucose substrate present to gluconic acid in 3.5 hour under these conditions. In nutrient broth as a starter culture in a similar experiment, 32% of the glucose substrate was converted to gluconic acid in same time. These results suggest that pontiac broth is better medium for starter culture of bacteria for the production of gluconic acid, when glucose is used as a sole carbon source.

EXAMPLE 12

Summary of Sugar Acid Production by Different *Pseudomonas* Strains on Different Carbon Sources The levels of sugar acids produced by *Pseudomonas* strain AN5 rif (AGAL Accession No. NM 00/09624), and the two transposon mutants, PQQ⁻ and SOS⁻, carrying the Tn5:uidA transposon in the pqqD and sugar oxidase genes (Example 9), were determined following growth in pontiac media, with or without 2% (w/v) aldose in the culture medium. Data are presented in Table 5.

TABLE 5

| Bacterial strain | added sugar | Time (hr) | Culture O.D. | media pH | sugar acid (mg/ml) |
|---|---|---|---|---|---|
| PQQ- | none | 17 | 240 | 7.0–8.3 | 0.00 |
|  | glucose | 63 | 410 | 5.95 | 0.117 |
| SOX- | none | 17 | 232 | 7.0–8.3 | 0.00 |
|  | glucose | 63 | 380 | 5.9 | 0.117 |
| AN5 rif | none | 17 | 212 | 6.1–8.6 | 0.00 |
|  | glucose | 47 | 450 | 2.95 | 5.10 |
|  | glucose | 64 | 305 | 3.0 | 5.10 |
|  | none | 23 | 235 | 8.6 | 0.00 |
|  | galactose | 47 | 435 | 3.35 | 1.61 |
|  | galactose | 70 | 390 | 3.1 | 2.24 |
|  | none | 23 | 235 | 6.1–8.6 | 0.00 |
|  | mannose | 70 | 380 | 3.25 | 3.92 |

Data are consistent with glucose being the preferred carbon source for *Pseudomonas* strain AN5 and derivatives thereof to produce sugar acids from aldose substrate.

EXAMPLE 13

Production of Antifungal Effective Amounts of Sugar Acids in situ on Wheat Roots by *Pseudomonas* Strain AN5

Wheat seeds were treated with various biocontrol bacteria and grown in sterile magenta jar assays in vermiculite. We collected the root exudate of wheat roots inoculated with these various biocontrol strains. These included the parent strain (i.e. *Pseudomonas* strain AN5), *Pseudomonas* strain AN5 rif (AGAL Accession No. NM 00/09624), and various mutants, including the PQQ- and SOX- mutants. The exudate were concentrated by freeze drying and then resuspended in water. Only *Pseudomonas* strain AN5. and *Pseudomonas* strain AN5 rif showed strong biological activity in bioassays against the take-all pathogen. The extracts from the remaining mutant strains, or untreated wheat, showed no biological activity. These data suggest that the sugar acid is produced by *Pseudomonas* strain AN5, or *Pseudomonas* strain AN5rif (AGAL Accession No. NM 00/09624), on wheat roots, in suppression of the take-all pathogen on wheat roots.

EXAMPLE 14

Isolation of Nucleotide Sequences of *Pseudomonas* sp. Encoding PQQ-Dependent Sugar Oxidases and PQQ-Biosynthesis Genes To identify the gene region of *Pseudomonas* sp. which encodes genes for the production of sugar acids, mutant lines were produced by transposon mutagenesis using a Tn5:uidA transposon. Two mutant lines were identified which failed to confer protection against take-all fungus in bioassays.

Restriction enzyme fragments (e.g. BamH1, Hind III, EcoR 1) were produced from these mutant lines. Mapping and sequence analyses of the cloned fragments indicated that the transposon was inserted into two non-contiguous regions of the genome, as follows:

1. a first region encoding the enzymes involved in catalysing the conversion of aldose to sugar acid, the partial sequence of which is set forth in SEQ ID NO: 1; and 2. a second region encoding the enzymes required for the synthesis of the cofactor, PQQ, the partial sequence of which is presented in SEQ ID NO: 4.

Limited homology of the nucleotide sequence set forth in SEQ ID NO: 1 to bacterial dehydrogenases suggests that this sequence encodes an enzyme involved in sugar metabolism.

Nucleotide sequence analysis also indicated that the transposon was inserted into the pqqD gene of the second region. In particular, an alignment of the pqqD gene of 10 *Pseudomonas* strain AN5, with the pqqD genes of other bacteria, indicating limited identity (not shown). These data indicated that this tagged region of the *Pseudomonas* sp. genome comprises the PQQ operon.

Southern blot hybridisation mapping analyses indicate that the sugar oxidase gene of 15 *Pseudomonas* strain AN5 is contained on the following DNA fragments: a 3.8 kb BamHI fragment; a 7.6 kb Bgl II fragment; a 6.5 kb PstI fragment; an approximately 18 kb HindIII fragment; and an approximately 22 kb EcoRI fragment.

Southern blot hybridisation mapping analyses indicate that the PQQ operon oxidase gene of *Pseudomonas* strain AN5 is contained on the following DNA fragments: an approximately 20 kb BamHI fragment; an 8.0 kb PstI fragment; an approximately 18 kb HindIII fragment; and an approximately 20 kb EcoRI fragment.

The appropriate genomic regions were isolated from *Pseudomonas* strain AN5, which possesses anti-fungal activity, and cloned into the cosmid vector pLAF3, to produce the following cosmid clones:

1. Cosmid pMN M53 (AGAL Accession No. NM 00/09622), comprising 3040 kb of *Pseudomonas* strain AN5 DNA which comprises nucleotide sequences encoding a sugar oxidase enzyme; and 2. Cosmid pMN-L2 (AGAL Accession No. NM 00/09621), comprising 3040 kb of *Pseudomonas* strain AN5 DNA which comprises nucleotide sequences of the PQQ operon.

Figure 13:
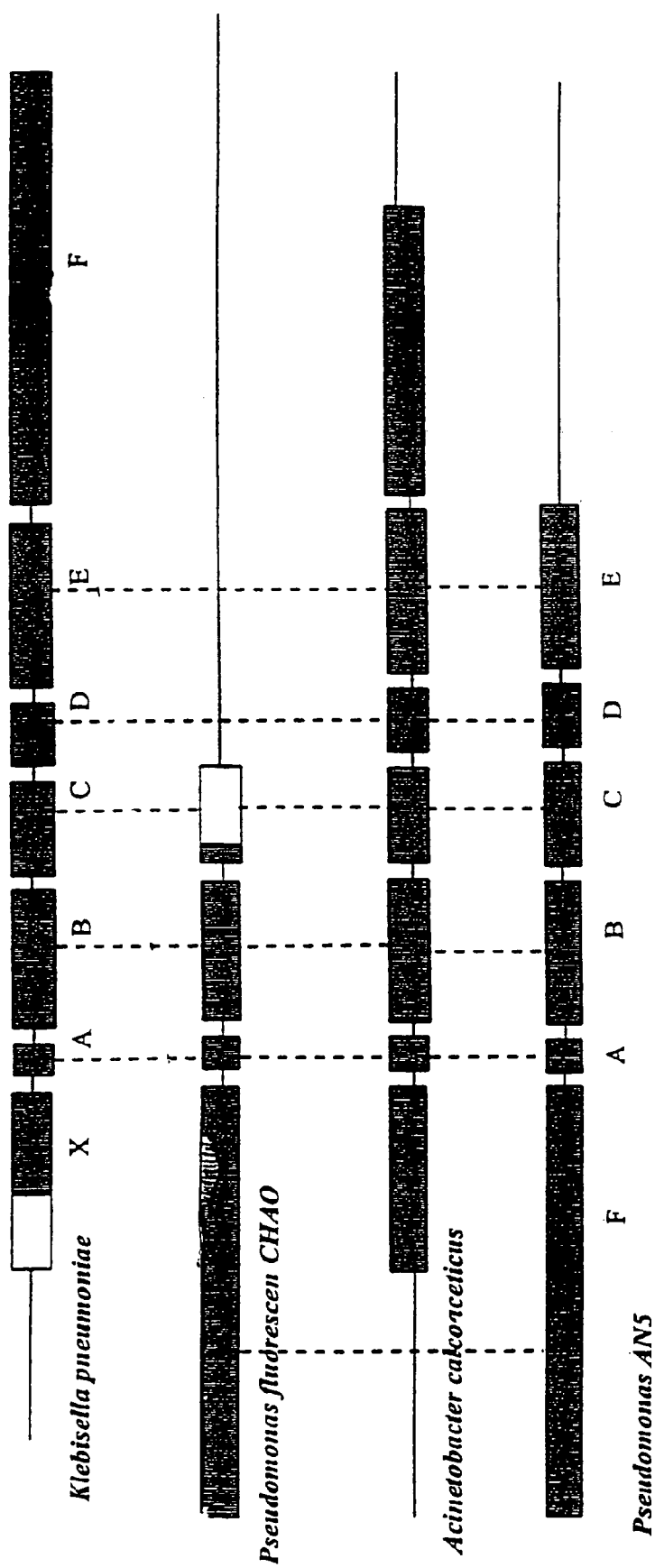
FIG. 13 is a copy of a schematic representation showing the aligned PQQ operons of *Klebsiella pneumoniae*, *Pseudomonas fluorescens* strain CHAO, *Acinetobacter calcoaceticus*, and *Pseudomonas* strain AN5, showing the locations of the pqqA, pqqB, pqqC, pqqD, and pqqE genes within the operon. Each gene is represented by a filled box, with the appropriate gene designation below.

The nucleotide sequences of the various genes of the PQQ operon were determined, and are set forth in SEQ ID NOs: 2 to 6. Mapping data presented in FIG. 13 indicate the relative arrangement of the genes of the PQQ operon of *Pseudomonas* sp. compared to other bacteria.

REFERENCES

1. Amann and Brosius (1985). *Gene* 40:183.
2. An, et al. (1985) *EMBO J.* 4:277–284.
3. Armstrong, et al. (1990) *Plant Cell Rep.* 9: 335–339.
4. Aszalos, A., et al. (1968) *J. Chromatography* 37: 487–498.
5. Ausubel, et al. (1987) In: *Curr. Protocol. Mol. Biol.* Wiley Interscience.
6. Baker, K. F. et al (1974) Biol. control plant pathogens, W.H. Freeman and Co., USA.
7. Buyer, J. S. et al. (1986) *J. Biol. Chem.* 261: 791–794.
8. Christou, et al. (1988) *Plant Physiol.* 87: 671–674.
9. Crossway, et al. (1986) *Mol. Gen. Genet.* 202:179–185.
10. Devereux, J., et al. (1984) *Nucl. Acids Res.* 12: 387–395.
11. Fravel, D. R. (1988) *Ann. Rev. Phytopathol.* 26: 75–91.
12. Gal A. E. (1968) *Anal. Biochem.* 24: 452461.
13. Gennaro, A. R. (1990) In: Remington's Pharmaceutical Sciences, 18th edition, Mack Publishing Company, Easton, Pa. 18042, USA, pp 1266–1268.
14. Ghebregzabher, et al. (1976) *J. Chrom.* 127: 133–162.
15. Gurusiddaiah S., et al. (1986) *Antimicrob. Agent. Chemother.* 29: 488495.
16. Hamdan, H., et al. (1991) *App. Environ. Microbiol.* 57: 3270–3277.
17. Fromm, et al. (1985) *Proc. Natl. Acad. Sci. (USA)* 82: 5824–5828.
19. Herrera-Estella et al. (1983a) *Nature* 303: 209–213.
20. Herrera-Estella et al. (1983b) *EMBO J.* 2: 987–995.
21. Herrera-Estella et al. (1985) In: Plant Genetic Engineering, Cambridge University Press, N.Y., pp 63–93.
22. Huynh et al. (1985) In: DNA Cloning Vol. I: A Practical Approach (ed, D. M. Glover), IRL Press Limited, Oxford. pp49–78.
23. Keel C, et al. (1992) *Mol. Plant-Microb. Interact.* 5: 4–13.
24. Keel C, et al (1996) *App. Environ. Microbiol.* 62: 552–63.
25. Kim et al. (1988) *Phytopathol.* 78: 488–492.
26. Kim et al. (1990) *Can J. Microbiol.* 36: 199–205.
27. Kirk-Othmer, et al. (1980) In: Encyclopedia of Chemical Technology, Third Edition, Vol. 11 (eds: H. F. Mark; D. F. Othmer; C. G. Overberger; G. T. Seaborg; M. Grayson; and D. Eckroth) John Wiley & Sons, New York, pp 490–498.
28. Kloepper, J. W., et al (1980) *Nature* 286: 885–886.
29. Kraus et al (1992) *Phytopathol.* 82: 264–271.
30. Krens, et al. (1982) *Nature* 296: 72–74.
31. Laville, J., et al. (1992) *Proc. Nat Acad. Sci. USA* 89: 1563–1566.
32. Leong, J. (1986). *Ann. Rev. Phytopathol.* 24:187–209.
33. McPherson, M. J., et al. (1991) *PCR A Practical Approach*. IRL Press, Oxford University Press, Oxford, United Kingdom.
34. Murray, G. M., Brown, J. F. (1987) *Aust. Plant Pathol.* 16: 34–37.
35. Murray, F. R. et al. (1997) *Curr. Genet.* 32: 367–375.
36. Nayudu, M., Holloway, B. W. (1981) *Plasmid* 6: 53–66.
37. Nayudu, M., Rolfe, B. G. (1987) *Mol Gen. Genet.* 206: 326–337.
38. Nayudu, M., et al. (1994a) In: Curr. topics Mol. Genet. (ed, S. G. Pandalai, Council of Scientific Integration), pp127–150.
39. Nayudu, M., et al. (1994b) In: Plant Growth Promoting Bacteria. (eds, M. Ryder, P. M. Stephens, and G. D. Bowen) pp 122–124.
40. Needleman and Wunsch (1970) *J. Mol. Biol.* 48:443453.
41. Paszkowski, et al (1984) *EMBO J.* 3: 2717–2722.
42. Pfender W F, et al. (1993) *Phytopathol* 83: 1223–1228.
43. Poplawsky, A. R., et al. (1988) *Phytopathol.* 78: 426–432.
44. Raaijmakers, J. M., et al. (1998) *Mol. Plant Mic. Interact.* 11:144–152.
45. Rosales A M, et al. (1995) *Phytopathol.* 85:1028–1032.
46. Sanford, J. C., et al. (1988) *Part. Sci. Technol.* 5: 27–37.
47. Schroth, M. N. et al. (1981). *Ann. Rev. Microbiol.* 35: 453–476.
48. Shimatake and Rosenberg (1981) *Nature* 292:128.
49. Still W. C., et al. (1978) *J. Org. Chem.* 43: 2923–2925.
50. Stosz et al., (1996) *App. Environ. Microbiol.* 62: 3183–3186.
51. Studier and Moffat (1986) *J. Mol. Biol.* 189: 113.
52. Suslow, T. V. (1982). In: Phytopathogenic Prokaryotes, (eds, M. S. Mount, and G. H. Lacey), Academic Press, London, pp 187–223.
53. Thomashow, L. S., et al. (1990) *Appl. Environ. Biol.* 56: 908–912.
54. Thomashow, L. S., et al. (1993) In: Mol. Genet. Plant Microbe Interact., Kluwer Academic Publishers, pp 535–641.
55. Thompson, et al. (1994) *Nucl. Acids Res.* 22: 46734680.
56. Weller, D. M. (1988) *Ann. Rev. Phytopathol.* 26: 379407.
57. Weller, D. M., et al. (1983). *Phytopathol.* 73: 463469.
58. Wong, P. T. W., et al. (1996) *Plant Pathology* 45: 285–293.
59. Wu, et al., (1995) *The Plant Cell* 7: 1357–1368.a)

The invention claimed is:

1. An isolated biocontrol agent for the treatment of a fungal infection in a plant or animal, said agent comprising a mutant of *Pseudomonas* strain AN5 having all of identifying characteristics of *Pseudomonas* strain AN5 rif (AGAL Accession No. NM 00/09624) including the following characteristics:

(i) it produces more sugar acid per cell than *Pseudomonas* strain AN5 when cultured in the presence of a carbon source comprising an aldose;

(ii) it is capable of colonizing the infection site of a fungal pathogen of a plant; and (iii) by virtue of (i) and (ii), it has increased ability to reduce or prevent the growth of a fungus compared to *Pseudomonas* strain AN5 as determined in a standard bioassay for growth of the fungus.

2. The biocontrol agent according to claim 1 wherein the sugar acid is selected from the group consisting of mannonic acid, gluconic acid, and galacturonic acid.

3. The biocontrol agent according to claim 2 wherein the sugar acid is gluconic acid.

4. The biocontrol agent according to claim 1 wherein the fungal pathogen is selected from the group consisting of: *Alternaria* spp.; *Armillaria mellae*; *Arthrobotrys oligosporus*; *Boletus granulatus*; *Botrytis fabae*; *Botritis cinerea*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; and *Verticillium dahliae*.

5. The biocontrol agent according to claim 4 wherein the fungal pathogen is *G. graminis* (take-all fungus).

6. The biocontrol agent according to claim 4 wherein the fungal pathogen is *Botrytis fabae*.

7. A method of treatment of a fungal infection in a plant comprising applying the biocontrol agent of claim 1 to the plant under conditions sufficient for the biocontrol agent to produce an anti-fungal effective amount of a sugar acid sufficient to prevent growth of a fungal pathogen of the plant.

8. The method according to claim 7 wherein the fungal pathogen is selected from the group consisting of: *Alternaria* spp.; *Armillaria mellae*; *Arthrobotrys oligosporus*; *Boletus granulatus*; *Botrytis fabae*; *Botritis cinerea*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; and *Verticillium dahliae*.

9. The method according to claim 8 wherein the fungal pathogen is *G. graminis* (take-all fungus).

10. The method according to claim 8 wherein the fungal pathogen is *Botrytis fabae*.

11. The method according to claim 7 wherein the sugar acid is selected from the group consisting of mannonic acid, gluconic acid, and galacturonic acid.

12. The method according to claim 11 wherein the sugar acid is gluconic acid.

13. The method of claim 7 wherein the biocontrol agent comprises mutant *Pseudomonas* strain AN5rif (AGAL Accession No. NM 00/09624).

14. A method of increasing the post-harvest storage of a product from a non-aquatic plant comprising applying to said product the biocontrol agent according to claim 1 under conditions sufficient for the biocontrol agent to produce an anti-fungal effective amount of a sugar acid sufficient to prevent growth of a fungal pathogen on said product.

15. The method according to claim 14 wherein the fungal pathogen is selected from the group consisting of: *Alternaria* spp.; *Armillaria mellae*; *Arthrobotrys oligosporus*; *Boletus granulatus*; *Botrytis fabae*; *Botritis cinerea*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; and *Verticillium dahliae*.

16. The method according to claim 15 wherein the fungal pathogen is *G. graminis* (take-all fungus).

17. The method according to claim 15 wherein the fungal pathogen is *Botrytis fabae*.

18. The method according to claim 14 wherein the sugar acid is selected from the group consisting of mannonic acid, gluconic acid, and galacturonic acid.

19. The method according to claim 18 wherein the sugar acid is gluconic acid.

20. The method of claim 14 wherein the biocontrol agent comprises mutant *Pseudomonas* strain AN5rif (AGAL Accession No. NM 00/09624).

21. A phytoprotective composition for the treatment of a fungal infection of a plant comprising the biocontrol agent according to claim 1 in combination with a phytopathologically-acceptable diluent or wetting agent.

22. The biocontrol agent according to claim 1 wherein the mutant of *Pseudomonas* strain AN5 is a naturally-occurring mutant having antibiotic resistance.

23. The biocontrol agent of claim 22 wherein the antibiotic resistance confers on the mutant an ability to grow on rifampicin.

24. The method of claim 7 wherein the biocontrol agent comprises a naturally-occurring mutant of *Pseudomonas* strain AN5 having antibiotic resistance.

25. The method of claim 24 wherein the antibiotic resistance confers on the mutant an ability to grow on rifampicin.

26. The method of claim 14 wherein the biocontrol agent comprises a naturally-occurring mutant of *Pseudomonas* strain AN5 having antibiotic resistance.

27. The method of claim 26 wherein the antibiotic resistance confers on the mutant an ability to grow on rifampicin.

* * * * *

SEQUENCE LISTING

<160> NUMBER OF SEQ ID NOS: 6

<210> SEQ ID NO 1
<211> LENGTH: 757
<212> TYPE: DNA
<213> ORGANISM: Pseudomonas sp.

<400> SEQUENCE: 1

| gctgacagca | ccacgccggc | cagcaccgtg | tgcccgcgtc | gcattttcct | gccgaccgcc | 60 |
| gacactcgcc | tgatcgccct | caatgccgca | ccggcaagat | gtgcgaagac | ttcggtgaca | 120 |
| aaggccaggt | cgacctgagc | gccaacatcg | gtggtttcac | cgcgggcggt | tactactcca | 180 |
| cctcgcctcc | ggccgttacc | cagaacctgg | tggtgatcgg | cggccacgtc | accgacaacg | 240 |
| tttccaccga | cgaacccagc | ggcgtcatcc | gcgcctacga | cgtgcacacc | ggcaagttgg | 300 |
| tgtggaactg | ggacagcggc | aagccggacg | acaccacgcc | gatcgccgag | ggccagactt | 360 |
| acacccgcaa | ttcgccgaac | atgtggtcca | tgttcagcgt | cgatgaaaaa | cttggcatgc | 420 |
| tctacctgcc | aatgggcaac | cagacccccg | accagttcgg | tggctgcgta | ccccggaatc | 480 |
| ggaaaaatac | tccgccggcc | tgaccgcgct | ggacatcgcc | accggcaagg | tgcgctggta | 540 |
| cttcagttca | cccaccacga | cctgtgggac | atggacgtcg | gcggtcaacc | gaccctgatg | 600 |
| gacatgaaga | ccgccgacgg | cgtgaaaccg | gccgtactgg | cctcgacaaa | caagggcaag | 660 |
| catctacgtg | ctggaccgca | gcaacggcca | gccgatcatt | ccgatcaagg | aaatccccgg | 720 |
| tgcccgcaag | gtgccggtgg | aaggcgaac | aacacct | | | 757 |

<210> SEQ ID NO 2
<211> LENGTH: 508
<212> TYPE: DNA
<213> ORGANISM: Pseudomonas sp.
<220> FEATURE:
<221> NAME/KEY: misc_feature
<222> LOCATION: 403
<223> OTHER INFORMATION: n = A,T,C or G

<400> SEQUENCE: 2

| tactgtgccg | cgcctgggcc | cgcaggctgc | cgttgcgaaa | acctgcgcaa | ttggcgcaaa | 60 |
| gcagttccat | tgaggaaaac | cgcgcccagc | ggcggaacct | agaatctgca | ccaacatggc | 120 |
| cgctccatct | gcaaaccgaa | ataaaaaacg | ccccgggtga | ccgaggcgtt | tgctgcgcat | 180 |
| tcaaccgact | gcagcaatca | acggctggcg | aagtacatgt | tgacttcgaa | accgatacgc | 240 |
| aggtcgatat | atgcgggttt | ggaccaggac | atggaaatac | tcctttggtt | ggggtgggac | 300 |
| ggttgagatc | tatacatata | gtccacctcc | gttcggagat | gttcagatgc | ttaggctgct | 360 |
| atggtactaa | attaaacaaa | atcgcacgcc | tcgattctcc | ganaaaagct | cattgcagac | 420 |
| gctggaatga | tcatttcggc | atgtgccaat | gttcatcccg | gcaaacacc | gttgctcagg | 480 |
| caataccggc | caccttcggc | gtcgatca | | | | 508 |

<210> SEQ ID NO 3
<211> LENGTH: 660
<212> TYPE: DNA
<213> ORGANISM: Pseudomonas sp.

<400> SEQUENCE: 3

| ttaattcgta | ggccatgctc | atcgcatcga | gcatgctcca | gagaatgtcc | agcttgaact | 60 |
| ggagaatctc | cagcatgtgc | tcctggcccg | cgcgggtggt | gtaatgctgc | aaggtaatcg | 120 |

-continued

```
ccaggccatg ctccacgtca cggcgggcct gaccgaggcg ggtgcggaag tattcataac      180
cggccggatc gatccacggg tagtgctgtg gccaactgtc caggcgcgac tgatggatct      240
gcggcgcgaa cagctcggtc agcgagctac tggcggcttc ctgccaactg gcccggcgag      300
cgaagttgac gtaggcatcc acggcgaatc gcacccctgg cagcaccaat tcctgggagc      360
gcagttgatc gggatccaac cccacggcct ggcccaaccg cagccaggcc tcgatgccgc      420
cgtcttcgcc gggtgcgccg tcatggtcga gcaggcgctg gatccactcg cgacggatct      480
cccgatccgg gcagttggcc aggatcgcgg catccttcag cggaatgttc acctgatagt      540
aaaagcggtt ggcgacccag ccctggattt gctcgcgagt ggcacggcct tcatacatcg      600
ccacgtgata cggatgatgg atgtggtaat acgcgccctt ggcttcgcag ggcccgtttc      660
```

<210> SEQ ID NO 4
<211> LENGTH: 315
<212> TYPE: DNA
<213> ORGANISM: Pseudomonas sp.

<400> SEQUENCE: 4

```
taaggatgca caaaaccaaa acccctcgct ggcgccccgg ctatcgcttc cagtacgaac       60
cggcgcagaa aggtcatgtg ttgctctatc ctgaaggcat gatcaagctc aacgacagcg      120
ctgcgctgat cggcggcctg atcgacggtg aacgggatgt cgcagccatc atcggcgagc      180
tggccaagca gtttcccgac gtgcccgaac tcggtgacga catcgagcag ttcatggagg      240
tcgcccgtgc agagcattgg atcgaacttg cctgaccagc cagcgatcgg cttgccgctg      300
tggttgctgg cggag                                                      315
```

<210> SEQ ID NO 5
<211> LENGTH: 810
<212> TYPE: DNA
<213> ORGANISM: Pseudomonas sp.

<400> SEQUENCE: 5

```
tgcaggtggc gagctcgacg aagtcggcct caagggcaat gcacagctcg atgatgcggt       60
cgatcttgtc gatgttgtgc cgatgggtaa cgaagttgag caccatcggg tagccgtggg      120
ccttcactgc ccgggccatt tccagcttct gtgcgaaggc tttcttcgag ccggccagca      180
ggttgttcac ctgttcgtcg ctggcctgga agctgatctg gatatgatcg aggccggcct      240
tcttgaagtc gctgatttc tgttcggtca aaccgatgcc ggaggtgatc aggttggtgt      300
agaaacccaa cttgcgcgcc tcgccgatca gttcggcgag gtcctggcgc accagcggtt      360
cgccaccgga aaagcccagc tgcgcggcgc ccatttccct ggcttcgcga aagaccttga      420
accactgctc ggtgctcagc tccttgccct gctcggcgaa gtccagcggg ttggaacagt      480
aggggcattg cagcgggcaa cgataggtca gctccgccag caaccacagc ggcaagccga      540
tcgctggctg gtcaggcaag ttcgatccaa tgctctgcac gggcgacctc catgaactgc      600
tcgatgtcgt caccgagttc ggcacgtcgg gaaactggtt ggccagctcg ccgatgatgg      660
ctgcgacata ccgttaccgt cgatcaggcc cgccgatcaa cgcaacgctt gcgttgaact      720
tgatcatgcc tttcaggaaa aaaacaaaca catgaccttt gtgcgcccgg ttcgtacttg      780
gaaagcgata agccggggcc gccaaccgaa                                       810
```

<210> SEQ ID NO 6
<211> LENGTH: 354
<212> TYPE: DNA
<213> ORGANISM: Pseudomonas sp.

-continued

```
<400> SEQUENCE: 6
gttactaaat taaacaaaat cgcacgcctc gattctccga gaaagctcat tgcagacgct        60
gtaatgatca tttcggcatg tgccaatgtt catccgggca aacaccgttg ctcaggcaat       120
accggccacc ttcggcgtcg atcaggcgtc gggtggcatc gagcaattgc ttgcgattca       180
atcctgcgat cgcatcgcaa agttgctcaa ggtaatccga cgggcggccg gccagtttac       240
cctgccaaag caattcggcc gttgggcgca gggcaaggtg tcgcttgtga aactgggagg       300
cgaagtgccc gttgctgggt cgagcaaggt cgaatcgtcg acctgtcgga tcag            354
```